(12) United States Patent
Georgiou et al.

(10) Patent No.: US 10,772,913 B2
(45) Date of Patent: *Sep. 15, 2020

(54) ADMINISTRATION OF KYNURENINE DEPLETING ENZYMES FOR TUMOR THERAPY

(71) Applicant: BOARD OF REGENTS, THE UNIVERSITY OF TEXAS SYSTEM, Austin, TX (US)

(72) Inventors: George Georgiou, Austin, TX (US); Everett Stone, Austin, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/373,588

(22) Filed: Apr. 2, 2019

(65) Prior Publication Data

US 2020/0054674 A1 Feb. 20, 2020

Related U.S. Application Data

(62) Division of application No. 15/351,060, filed on Nov. 14, 2016, now abandoned, which is a division of application No. 14/473,040, filed on Aug. 29, 2014, now Pat. No. 9,808,486.

(60) Provisional application No. 61/986,366, filed on Apr. 30, 2014, provisional application No. 61/872,132, filed on Aug. 30, 2013.

(51) Int. Cl.
| | |
|---|---|
| *C12N 9/14* | (2006.01) |
| *A61K 35/17* | (2015.01) |
| *A61K 38/46* | (2006.01) |
| *A61K 38/00* | (2006.01) |

(52) U.S. Cl.
CPC .............. *A61K 35/17* (2013.01); *A61K 38/46* (2013.01); *C12N 9/14* (2013.01); *C12Y 307/01003* (2013.01); *A61K 38/00* (2013.01)

(58) Field of Classification Search
USPC ........................................................ 435/148
See application file for complete search history.

(56) References Cited

U.S. PATENT DOCUMENTS

| | | |
|---|---|---|
| 7,109,304 B2 | 9/2006 | Hansen et al. |
| 7,714,139 B2 | 5/2010 | Prendergast et al. |
| 8,377,976 B2 | 2/2013 | Combs et al. |
| 8,465,743 B2 | 6/2013 | Rosenberg |
| 9,808,486 B2 | 11/2017 | Georgiou et al. |
| 9,975,959 B2 | 5/2018 | Georgiou et al. |
| 2009/0304666 A1 | 12/2009 | Harrison |
| 2015/0064154 A1 | 3/2015 | Georgiou |
| 2016/0058845 A1 | 3/2016 | Georgiou et al. |
| 2017/0056449 A1 | 3/2017 | Georgiou |

FOREIGN PATENT DOCUMENTS

| | | |
|---|---|---|
| CN | 1442487 | 9/2003 |
| JP | 2006-521378 | 9/2006 |
| JP | 2008-237022 | 10/2008 |
| JP | 2010-504346 | 2/2010 |
| JP | 2006-521378 | 11/2016 |
| WO | WO 2007/004692 | 1/2007 |
| WO | WO 2012/031744 | 3/2012 |
| WO | WO 2012/079000 | 6/2012 |
| WO | WO 2012/099441 | 7/2012 |
| WO | WO 2013/034685 | 3/2013 |
| WO | WO 2013/059593 | 4/2013 |
| WO | WO 2015/031771 | 3/2015 |
| WO | WO 2016/033488 | 3/2016 |
| WO | WO 2017/151860 | 9/2017 |

OTHER PUBLICATIONS

Extended European Search Report issued in European Application No. 17760774.4, dated Jul. 22, 2019.
International Search Report and Written Opinion issued in PCT Application No. PCT/US2019/027623, dated Aug. 22, 2019.
Office Communication issued in Japanese Application No. 2017-511675, dated Jun. 27, 2019. (English Translation).
Rabinkov et al., "Alliinase: structural peculiarities and applying for targeted therapy: SW02. W10-4". *FEBS J.*, 280.1, 2013.
"KYNU_Human," UniProt Submission Q16719, dated Jul. 24, 2013.
"Kynureninase (EC 3.7.1.3)—human", GenBank accession No. G02652, 1999.
"SIDS2vsH1YAV1," UniProt 201609, dated Mar. 21, 2012.
Adams et al. "The kynurenine pathway in brain tumor pathogenesis." *Cancer Research* 72.22 (2012): 5649-5657.
Alberati-Giani et al., "Isolation and expression of a cDNA clone encoding human kynureninase," *Eur J Biochem.*, 239: 460-468, 1996.
Chen and Guillemin, "Kynurenine pathway metabolites in humans: disease and healthy states," *Int. J. Tryptophan Res.*, 2:1-19, 2009.
Curran et al., "PD-1 and CTLA-4 combination blockade expands infiltrating T cells and reduces regulatory T and myeloid cells within B16 melanoma tumors," *Proc. Natl. Acad. Sci. U S A*, 107:4275-4280, 2010.
De Jong et al., "Serum tryptophan and kynurenine concentrations as parameters for indoleamine 2,3-dioxygenase activity in patients with endometrial, ovarian, and vulvar cancer," *Int. J. Gynecol. Cancer*, 21(7):1320-1327, 2011.
Della Chiesa et al., "The tryptophan catabolite L-kynurenine inhibits the surface expression of NKp46- and NKG2D-activating receptors and regulates NK-cell function," *Blood*, 108(13):4118-4125, 2006.

(Continued)

*Primary Examiner* — Sheridan Swope
(74) *Attorney, Agent, or Firm* — Parker Highlander PLLC

(57) ABSTRACT

Methods and compositions related to the use of a protein with kynureninase activity are described. For example, in certain aspects there may be disclosed a modified kynureninase capable of degrading kynurenine. Furthermore, certain aspects of the invention provide compositions and methods for the treatment of cancer with kynurenine depletion using the disclosed proteins or nucleic acids.

19 Claims, 10 Drawing Sheets
Specification includes a Sequence Listing.

(56) References Cited

OTHER PUBLICATIONS

Disis et al., "Use of tumor-responsive T cells as cancer treatment", *Lancet*, 373:673-683, 2009.
Duval et al., "Adoptive transfer of allogenic cytotoxic T lymphocytes equipped with a HLA-A2 restricted MART-1 T-cell receptor: a phase I trial in metastatic melanoma", *Clin. Cancer Res.*, 12:1229-1236, 2006.
Extended European Search Report issued in corresponding European Application No. 18204264, dated Apr. 25, 2019.
Extended European Search Report issued in European Patent Application No. 14840339.7, dated Mar. 28, 2017.
Gailani et al., "Studies on tryptophan metabolism in patients with bladder cancer," *Cancer Research.*, 33: 1071-1077, 1973.
Godin-Ethier et al., "Indoleamine 2, 3-Dioxygenase Expression in Human Cancers: Clinical and Immunologic Perspectives," *Clinical Cancer Research*, 17(22):6985-6991, 2011.
Holmgaard et al., "Indoleamine 2, 3-dioxygenase is a critical resistance mechanism in antitumor T cell immunotherapy targeting CTLA-4," *The Journal of Experimental Medicine*, 210:1389-1402, 2013.
Hoyos et al., "Genetic modification of human T lymphocytes for the treatment of hematological malignancies", *Haematologica*, 97(11):1622-1631, 2012.
International Preliminary Report on Patentability issued in International Application No. PCT/US2014/053437, dated Mar. 10, 2016.
International Search Report and Written Opinion issued in International Application No. PCT/US2014/053437, dated Mar. 10, 2015.
International Preliminary Report on Patentability issued in International Application No. PCT/US2015/047475, dated Mar. 9, 2017.
International Search Report and Written Opinion issued in International Application No. PCT/US2015/047475, dated Feb. 2, 2016.
Kaper et al., "Nanosensor detection of an immunoregulatory tryptophan influx/kynurenine efflux cycle," *PLoS Biology*, 5(10):e257, 2007.
Lima et al., "Crystal Structure of *Homo sapiens* Kynureninase," *Biochemistry*, 46(10):2735-2744, 2007.
Lima et al., "Crystal structure of the *Homo sapiens* kynureninase-3-hydroxyhippuric acid inhibitor complex: insights into the molecular basis of kynureninase substrate specificity," *J. Med. Chem.*, 52(2): 389-396, 2009.
Lipowska-Bhalla et al., "Targeted immunotherapy of cancer with CAR T cells: achievements and challenges," *Cancer Immunology Immunotherapy*, 61(7):953-962, 2012.
Lob et al., "Inhibitors of indoleamine-2,3-dioxygenase for cancer therapy: can we see the wood for the trees?" *Nat. Rev. Cancer*, 9(6):445-452, 2009.
Mandi and Vecsei, "The kynurenine system and immunoregulation," *J. Neural Transm.*, 119(2):197-209, 2012.
Mezrich et al., "An interaction between kynurenine and the aryl hydrocarbon receptor can generate regulatory T cells," *The Journal of Immunology*, 185(6):3190-3198, 2010.
Office Communication issued in Chinese Application No. 201480053899.1, dated Feb. 15, 2019. (English Translation).
Office Communication issued in corresponding Japanese Application No. 2016-537898, dated Sep. 20, 2017. (English Translation).
Office Communication issued in Japanese Application No. 2018-042760, dated Jan. 16, 2019. (English Translation).
Office Communication Issued in U.S. Appl. No. 14/473,040, dated Nov. 23, 2016.
Office Communication issued in U.S. Appl. No. 14/839,293, dated Jan. 6, 2017.
Office Communication issued in U.S. Appl. No. 15/351,060, dated Dec. 12, 2016.
Office Communication issued in U.S. Appl. No. 14/839,293, dated Apr. 14, 2017.
Office Communication issued in U.S. Appl. No. 14/473,040, dated Jul. 3, 2017.
Office Communication issued in U.S. Appl. No. 14/473,040, dated Jul. 6, 2016.
Office Communication issued in U.S. Appl. No. 15/351,060, dated Mar. 9, 2018.
Office Communication issued in U.S. Appl. No. 15/351,060, dated Jun. 26, 2017.
Opitz et al., "An endogenous tumour-promoting ligand of the human aryl hydrocarbon receptor," *Nature*, 478(7368):197-203, 2011.
Opitz et al., "The Indoleamine-2, 3-Dioxygenase (IDO) Inhibitor 1-Methyl-D-tryptophan Upregulates IDO1 in Human Cancer Cells," *PLoS One*, 6(5):e19823, 2011.
Phillips, "Structure and mechanism of kynurinase", *Arch. Biochem. Biophys.*, 544:69-74, 2014.
Phillips, "Structure, mechanism, and substrate specificity of kynureninase", *Biochimica et Biophysica Acta*, 1814: 1481-1488, 2011.
Pilotte et al., "Reversal of tumoral immune resistance by inhibition of tryptophan 2,3-dioxygenase," *Proc. Natl. Acad. Sci. U S A*, 109(7):2497-2502, 2012.
Platten et al., "Cancer Immunotherapy by Targeting IDO1/TDO and Their Downstream Effect", *Front. Immunol.*, 5:673, 2015.
Prendergast, "Cancer: Why tumours eat tryptophan," *Nature*, 478(7368):192-194, 2011.
Response filed in U.S. Appl. No. 14/839,293, dated Mar. 6, 2017.
Rutella et al., "Targeting indoleamine 2,3-dioxygenase (IDO) to counteract tumour-induced immune dysfunction: from biochemistry to clinical development," *Endocr. Metab. Immune Disord. Drug Targets*, 9(2):151-177, 2009.
Schottler et al., "Protein engineering of the restriction endonuclease EcoRV—structure-guided design of enzyme variants that recognize the base pairs flanking the recognition site", *eur. J. Biochem.*, 258(1):184-191, 1998.
Shin et al., "Modulation of natural killer cell antitumor activity by the aryl hydrocarbon receptor," *Proc. Natl. Acad. Sci. U S A*, 110(30):12391-12396, 2013.
Simpson et al., "Fc-dependent depletion of tumor-infiltrating regulatory T cells co-defines the efficacy of anti-CTLA-4 therapy against melanoma," *J. Exp. Med.*, 210(9): 1695-1710, 2013.
Song et al., "L-Kynurenine-induced apoptosis in human NK cells is mediated by reactive oxygen species," *International Immunopharmacology*, 11(8):932-938, 2011.
Stone et al., "Abstract LB-226: Depletion of kynurenine using an engineered therapeutic enzyme potently inhibits cancer immune checkpoints both as a monotherapy and in combination with anti-PD-1," Proceedings of the AACR 106$^{th}$ Annual Meeting, Philadelphia, PA, Apr. 18-22, 2015, Cancer *Research*, 75(15 Supplement):LB-226-LB-226, Aug. 2015.
Supplementary European Search Report issued in European Patent Application No. 15834988.6, dated Jan. 16, 2018.
Toma et al., "Cloning and recombinant expression of rat and human kynureninase," *FEBS Letters.*, 408(1): 5-10, 1997.
UniProt_201609 Acc#H1YAV1 Lucas et al., Mar. 21, 2012. Alignment with SEQ ID No. 33.
Veronese et al., "Peptide and protein PEGylation: a review of problems and solutions," *Biomaterials*, 22(5): 405-417, 2001.
Walsh et al., "Purification and biochemical characterization of some of the properties of recombinant human kynurinase", *Eur. J. Biochem.*, 269:2069-2074, 2002.
Yao et al., "Serum metabolic profiling and features of papillary thyroid carcinoma and nodular goiter," *Mol. Biosyst.*, 7(9):2608-2614, 2011.
Yoshikawa et al., "Serum concentration of L-kynurenine predicts the clinical outcome of patients with diffuse large B-cell lymphoma treated with R-CHOP," *Eur. J. Haematol.*, 84(4):304-309, 2010.

ADMINISTRATION OF KYNURENINE DEPLETING ENZYMES FOR TUMOR THERAPY

The present application is a divisional of U.S. application Ser. No. 15/351,060, filed Nov. 14, 2016, which is a divisional of U.S. application Ser. No. 14/473,040, filed Aug. 29, 2014, now U.S. Pat. No. 9,808,486, which claims the priority benefit of U.S. provisional application Nos. 61/872,132, filed Aug. 30, 2013 and 61/986,366, filed Apr. 30, 2014, the entire contents of each of which are incorporated herein by reference.

The invention was made with government support under Grant No. R01 CA154754 awarded by the National Institutes of Health. The government has certain rights in the invention.

BACKGROUND OF THE INVENTION

1. Field of the Invention

The invention generally relates to compositions and methods for the treatment of cancer with enzymes that deplete L-kynurenine or L-3-hydroxykynurenine. More particularly, it concerns the engineering, pharmacological optimization and use of bacterial and mammalian enzymes with L-kynurenine degrading activity suitable for human therapy.

2. Description of Related Art

Overexpression of indolamine-2,3-dioxygenase isoforms (IDO1 or IDO2) by cancer cells or reprogramming of cancer infiltrating leukocytes to express either of these enzymes has been shown to have a profound effect on attenuating adaptive immune responses to cancer. IDO1 and IDO2 as well as the enzyme tryptophan 2,3-dioxygenase (TDO), whose expression by stromal cells may be induced by some tumors, catalyze the rate limiting step in tryptophan (Trp) catabolism to L-kynurenine (KYN) (Godin-Ethier et al., 2011). Tumors exchange a cytosolic KYN molecule for an extracellular Trp molecule using a LAT1-like amino acid exchanger (Kaper et al., 2007), which has the dual effect on immune cells of locally elevating levels of KYN while locally depleting Trp levels. Neighboring immune cells internalize KYN, where it is an activating ligand for the aryl hydrocarbon receptor (AHR) resulting in the expression of numerous cytokines and chemokines that lead to tumor tolerance through immune cell differentiation and/or induction of apoptosis (Della Chiesa et al., 2006; Opitz et al., 2011; Song et al., 2011). Additionally, other KYN-related compounds formed from kynurenine, most notably kynurenic acid also exert an immunosuppressive effect by serving as agonists of the orphan GPCR GPCR35. Inhibition of KYN formation (and thus inhibition of the formation of KYN metabolism byproducts, including kynurenic acid, 3-hydroxyl kynurenine and quinolinic acid, via the inhibition of IDO1 or TDO has received a significant amount of attention as a cancer target (Chen and Guillemin, 2009; Rutella et al., 2009; Prendergast, 2011). Substrate analog inhibitors, such as 1-DL-methyltryptophan, for IDO1 have been developed and have shown initial promise in overcoming cancer induced tumor tolerance thus restoring the ability of the native immune system to fight tumors (Lob et al., 2009). However, KYN is also produced by tryptophan 2,3-dioxygenase (TDO), which is also frequently expressed in tumors and this enzyme is not inhibited by 1-DL-methyltryptophan (Pilotte et al., 2012). There are also additional concerns with the D-isomer of 1-DL-methyltryptophan (1-D-MT) currently in phase 1 and 2 clinical trials. Paradoxically, 1-D-MT can upregulate IDO1 expression, actually increasing KYN levels and inducing immunosuppression in certain cancers (Opitz et al., 2011).

Controlling tumor production of KYN is the focus of much research and has the potential to treat, among others, cancers such as breast cancer, ovarian, glioblastoma, and pancreatic carcinoma. KYN is known to suppresses proliferation as well as induce apoptosis in T cells and NK cells (Opitz et al., 2011; Mandi and Vacsei, 2012) enabling tumors to evade detection and destruction by a patient's immune system. KYN is a potent ligand of the aryl hydrocarbon receptor (AHR) whose activation in T cells induces differentiation into CD25+FoxP3+ T regulatory cells (Tregs) (Mezrich et al., 2010). KYN has also been shown to prevent cytokine mediated up-regulation of specific receptors (NKp46 and NKG2D) required for NK mediated cell killing tumor cell lines (Della Chiesa et al., 2006), an action that is also likely mediated by its agonistic effect on AHR (Shin et al., 2013). There is also clinical evidence linking elevated serum KYN levels and decreased survival in multiple types of cancer. In healthy patients, KYN levels in serum are in the range of 0.5 to 1 µM. In patients with cancer types that produce KYN, such as diffuse large B-cell lymphoma, serum KYN levels were measured to be as much as 10 times higher (Yoshikawa et al., 2010; de Jong et al., 2011; Yao et al., 2011) and were prognostic for survival among lymphoma patients receiving the same treatment regimen; those with serum levels below 1.5 µM exhibited a 3 year survival rate of 89%, compared to only 58% survival for those with KYN levels above 1.5 µM. This difference in survival was attributed to the immune suppressing effects of KYN (Yoshikawa et al., 2010). The use of small molecule IDO inhibitors, such as 1-D-MT, has demonstrated the utility of controlling KYN levels in restoring immune function, but the off target effects of IDO1 up-regulation by 1-D-MT and lack of inhibition for TDO and the IDO1 isoform are of concern.

The present invention discloses the use enzymes for the specific depletion of KYN and its metabolites in tumors and/or in the blood. KYN depleting enzymes are used to lower KYN concentrations for the treatment of tumors expressing IDO1, IDO2, or TDO thus preventing tumor-mediated tolerogenic effects and instead mediating tumor-ablating pro-inflammatory responses. Notably, the use of enzymes for the depletion of KYN and KYN metabolic byproducts circumvents the problems associated with small molecule inhibitors of IDO isoforms and TDO discussed above and further completely circumvents off target effects that are very commonly accompany small molecule drugs and lead to unpredicted toxicities and side effects.

SUMMARY OF THE INVENTION

Aspects of the present invention overcome a major deficiency in the art by providing enzymes that comprise bacterial and mammalian polypeptide sequences capable of degrading L-kynurenine and 3-hydroxy-L-kynurenine and displaying favorable pharmacokinetics in serum as desired for cancer therapy. In some aspects, the kynureninase enzyme may have greater catalytic activity towards kynurenine than 3' OH-kynurenine. A kynureninase from a bacterial species may be used. Such an enzyme may have an amino acid sequence selected from the group consisting of SEQ ID NOs: 7 and 13-52 or a modified version thereof. In particular, the therapeutic may be derived from the

*Pseudomonas fluorescens* enzyme, kynureninase (Pf-KYNU). Alternatively, a kynureninase from *Saccharomyces cerevisiae* or *Neurospora crassa* may be used. The therapeutic may be derived from the *Mucilaginibacter paludis* kynureninase enzyme. Further, to prevent adverse effects due to the immunogenicity of heterologous kynureninases, the *Homo sapiens* enzyme or other primate kynureninases displaying >95% sequence identity to the human enzyme may be used. For example, a novel enzyme may have an amino acid sequence selected from the group consisting of SEQ ID NOs: 7-9.

In other aspects, there may be a polypeptide comprising either a native or modified human or primate kynureninase capable of degrading KYN and having activity towards the degradation of 3-hydroxykynurenine or kynurenic acid. In some embodiments, the polypeptide may be capable of degrading KYN under physiological conditions. For example, the polypeptide may have a catalytic efficiency for KYN ($k_{cat}/K_M$) of at least or about 0.01, 0.05, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, $10^4$, $10^5$, $10^6$ $M^{-1}s^{-1}$ or any range derivable therein.

A modified polypeptide as discussed above may be characterized as having a certain percentage of identity as compared to an unmodified polypeptide (e.g., a native polypeptide) or to any polypeptide sequence disclosed herein. For example, the unmodified polypeptide may comprise at least, or up to, about 150, 200, 250, 300, 350, 400 residues (or any range derivable therein) of a native kynureninase. The percentage identity may be about, at most or at least 40%, 50%, 55%, 60%, 65%, 70%, 75%, 80%, 85%, 90%, 95%, 96%, 97%, 98%, 99% or 100% (or any range derivable therein) between the modified and unmodified polypeptides, or between any two sequences in comparison. It is also contemplated that percentage of identity discussed above may relate to a particular modified region of a polypeptide as compared to an unmodified region of a polypeptide. For instance, a polypeptide may contain a modified or mutant substrate recognition site of a kynureninase that can be characterized based on the identity of the amino acid sequence of the modified or mutant substrate recognition site of the kynureninase to that of an unmodified or mutant kynureninase from the same species or across the species. A modified or mutant human polypeptide characterized, for example, as having at least 90% identity to an unmodified kynureninase means that at least 90% of the amino acids in that modified or mutant human polypeptide are identical to the amino acids in the unmodified polypeptide.

Such an unmodified polypeptide may be a native kynureninase, particularly a human isoform or other primate isoforms. For example, the native human kynureninase may have the sequence of SEQ ID NO: 8. Non-limiting examples of other native primate kynureninase include *Pongo abelii* kynureninase (Genbank ID: XP_002812508.1; SEQ ID NO: 10), *Macaca fascicularis* kynureninase (Genbank ID: EHH54849.1; SEQ ID NO: 11), and *Pan troglodytes* kynureninase (Genbank ID: XP_003309314.1; SEQ ID NO: 12). Exemplary native polypeptides include a sequence having about, at most or at least 50%, 55%, 60%, 65%, 70%, 75%, 80%, 85%, 90%, 95%, 96%, 97%, 98%, 99% or 100% identity (or any range derivable therein) of SEQ ID NO: 8 or 10-12 or a fragment thereof. For example, the native polypeptide may comprise at least or up to about 10, 20, 30, 40, 50, 60, 70, 80, 90, 100, 150, 200, 250, 300, 350, 400, 415 residues (or any range derivable therein) of the sequence of SEQ ID NO: 8 or 10-12.

In some embodiments, the native kynureninase may be modified by one or more other modifications, such as chemical modifications, substitutions, insertions, deletions, and/or truncations. For example, the modifications may be at a substrate recognitions site of the native enzyme. In a particular embodiment, the native kynureninase may be modified by substitutions. For example, the number of substitutions may be one, two, three, four or more. In further embodiments, the native kynureninase may be modified in the substrate recognition site or any location that may affect substrate specificity.

In one embodiment, an isolated, modified human kynureninase enzyme is provided, wherein the modified enzyme has at least one substitution relative to native human kynureninase (see SEQ ID NO: 8), and wherein the at least one substitution includes a Met or Leu substitution for a Phe normally found at position 306 of native human kynureninase. Thus, in one aspect, an isolated, modified human kynureninase enzyme is provided that comprises a Phe306Met substitution. In another aspect, an isolated, modified human kynureninase enzyme is provided that comprises a Phe306Leu substitution.

In some aspects, the present invention also contemplates polypeptides comprising a kynureninase linked to a heterologous amino acid sequence. For example, the kynureninase may be linked to the heterologous amino acid sequence as a fusion protein. In a particular embodiment, the kynureninase may be linked to amino acid sequences, such as an IgG Fc, albumin, an albumin binding protein, or an XTEN polypeptide for increasing the in vivo half-life.

To increase serum stability, the kynureninase may be linked to one or more polyether molecules. In a particular embodiment, the polyether may be polyethylene glycol (PEG). The polypeptide may be linked (e.g., covalently) to PEG via specific amino acid residues, such as lysine or cysteine. For therapeutic administration, such a polypeptide comprising the kynureninase may be dispersed in a pharmaceutically acceptable carrier.

In some aspects, a nucleic acid encoding such a kynureninase is contemplated. In some embodiments, the nucleic acid has been codon optimized for expression in bacteria. In particular embodiments, the bacteria is *E. coli*. In other aspects, the nucleic acid has been codon optimized for expression in fungus (e.g., yeast), insects, or mammals. The present invention further contemplates vectors, such as expression vectors, containing such nucleic acids. In particular embodiments, the nucleic acid encoding the kynureninase is operably linked to a promoter, including but not limited to heterologous promoters. In one embodiment, a kynureninase may be delivered to a target cell by a vector (e.g., a gene therapy vector). Such viruses may have been modified by recombinant DNA technology to enable the expression of the kynureninase-encoding nucleic acid in the target cell. These vectors may be derived from vectors of non-viral (e.g., plasmids) or viral (e.g., adenovirus, adeno-associated virus, retrovirus, lentivirus, herpes virus, or vaccinia virus) origin. Non-viral vectors are preferably complexed with agents to facilitate the entry of the DNA across the cellular membrane. Examples of such non-viral vector complexes include the formulation with polycationic agents which facilitate the condensation of the DNA and lipid-based delivery systems. An example of a lipid-based delivery system would include liposome based delivery of nucleic acids.

In still further aspects, the present invention further contemplates host cells comprising such vectors. The host cells may be bacteria (e.g., *E. coli*), fungal cells (e.g., yeast), insect cells, or mammalian cells.

In some embodiments, the vectors are introduced into host cells for expressing the kynureninase. The proteins may be expressed in any suitable manner. In one embodiment, the proteins are expressed in a host cell such that the protein is glycosylated. In another embodiment, the proteins are expressed in a host cell such that the protein is aglycosylated.

Certain aspects of the present invention also contemplate methods of treatment by the administration of the kynureninase peptide, the nucleic acid encoding the kynureninase in a gene therapy vector, or the formulation of the present invention, and in particular methods of treating tumor cells or subjects with cancer. The subject may be any animal, such as a mouse. For example, the subject may be a mammal, particularly a primate, and more particularly a human patient. In some embodiments, the method may comprise selecting a patient with cancer.

In some embodiments, the cancer is any cancer that is sensitive to kynurenine depletion. In one embodiment, the present invention contemplates a method of treating a tumor cell or a cancer patient comprising administering a formulation comprising such a polypeptide. In some embodiments, the administration occurs under conditions such that at least a portion of the cells of the cancer are killed. In another embodiment, the formulation comprises such a kynureninase with kynurenine-degrading activity at physiological conditions and further comprising an attached polyethylene glycol chain. In some embodiment, the formulation is a pharmaceutical formulation comprising any of the above discussed kynureninases and pharmaceutically acceptable excipients. Such pharmaceutically acceptable excipients are well known to those of skill in the art. All of the above kynureninases may be contemplated as useful for human therapy.

In a further embodiment, there may also be provided a method of treating a tumor cell comprising administering a formulation comprising a non-bacterial (mammalian, e.g., primate or mouse) kynureninase that has kynurenine-degrading activity or a nucleic acid encoding thereof.

The administration or treatment may be directed to the nutrient source for the cells, and not necessarily the cells themselves. Therefore, in an in vivo application, treating a tumor cell includes contacting the nutrient medium for a population of tumor cells with the kynureninase. In this embodiment, the medium can be blood, lymphatic fluid, spinal fluid and the like bodily fluid where kynurenine depletion is desired.

In accordance with certain aspects of the present invention, such a formulation containing the kynureninase can be administered intravenously, intradermally, intraarterially, intraperitoneally, intralesionally, intracranially, intraarticularly, intraprostaticaly, intrapleurally, intrasynovially, intratracheally, intranasally, intravitreally, intravaginally, intrarectally, intratumorally, intramuscularly, subcutaneously, subconjunctival, intravesicularlly, mucosally, intrapericardially, intraumbilically, intraocularly, orally, topically, by inhalation, infusion, continuous infusion, localized perfusion, via a catheter, via a lavage, in lipid compositions (e.g., liposomes), or by other method or any combination of the forgoing as would be known to one of ordinary skill in the art.

In a further embodiment, the method may also comprise administering at least a second anticancer therapy to the subject. The second anticancer therapy may be a surgical therapy, chemotherapy, radiation therapy, cryotherapy, hormone therapy, immunotherapy or cytokine therapy. In certain aspects, the second anticancer therapy may be an anti-PD-1, anti-CTLA-4, or anti-PD-L1 antibody.

In some embodiment, a cell comprising a chimeric antigen receptor (CAR) and a kynureninase enzyme are contemplated for use in treating a subject with cancer. In some aspects, the cell may be transfected with a DNA encoding the CAR and the kynureninase and, in some cases, a transposase.

The CAR may target any cancer-cell antigen of interest, including, for example, HER2, CD19, CD20, and GD2. The antigen binding regions or domain can comprise a fragment of the $V_H$ and $V_L$ chains of a single-chain variable fragment (scFv) derived from a particular human monoclonal antibody, such as those described in U.S. Pat. No. 7,109,304, which is incorporated herein by reference in its entirety. The fragment can also be any number of different antigen binding domains of a human antigen-specific antibody. In a more specific embodiment, the fragment is an antigen-specific scFv encoded by a sequence that is optimized for human codon usage for expression in human cells. For additional examples of CARs, see, for example, WO 2012/031744, WO 2012/079000, WO 2013/059593, and U.S. Pat. No. 8,465,743, all of which are incorporated herein by reference in their entireties.

The kynureninase may be any kynureninase disclosed herein. Methods of transfecting of cells are well known in the art, but in certain aspects, highly efficient transfections methods such as electroporation are employed. For example, nucleic acids may be introduced into cells using a nucleofection apparatus. Preferably, the transfection step does not involve infecting or transducing the cells with virus, which can cause genotoxicity and/or lead to an immune response to cells containing viral sequences in a treated subject.

A wide range of CAR constructs and expression vectors for the same are known in the art and are further detailed herein. For example, in some aspects, the CAR expression vector is a DNA expression vector such as a plasmid, linear expression vector or an episome. In some aspects, the vector comprises additional sequences, such as sequence that facilitates expression of the CAR, such a promoter, enhancer, poly-A signal, and/or one or more introns. In preferred aspects, the CAR coding sequence is flanked by transposon sequences, such that the presence of a transposase allows the coding sequence to integrate into the genome of the transfected cell.

In certain aspects, cells are further transfected with a transposase that facilitates integration of a CAR coding sequence into the genome of the transfected cells. In some aspects, the transposase is provided as DNA expression vector. However, in preferred aspects, the transposase is provided as an expressible RNA or a protein such that long-term expression of the transposase does not occur in the transgenic cells. Any transposase system may be used in accordance with the embodiments. In other aspects, cells may be infected with a lentivirus to facilitate integration of the CAR coding sequence and the kynureninase coding sequence into the genome of the cell.

In one embodiment, a composition comprising a kynureninase or a nucleic acid encoding a kynureninase is provided for use in the treatment of a tumor in a subject. In another embodiment, the use of a kynureninase or a nucleic acid encoding a kynureninase in the manufacture of a medicament for the treatment of a tumor is provided. Said kynureninase may be any kynureninase of the embodiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the terms "encode" or "encoding," with reference to a nucleic acid, are used to make the invention readily understandable by the skilled artisan; however, these terms may be used interchangeably with "comprise" or "comprising," respectively.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A—The population of circulating CD4+ regulatory T-cell is significantly smaller in the group treated with active PEG-Pf-KYNU. FIG. 5B—The population of tumor infiltrating CD8+ T-cells shows significantly higher expression of granzyme B and interferon γ.

FIG. 9B—Additive effects were observed with PD1 (antibody)/PEG-Pf-KYNU combination treatment eliminating 60% of tumors and PD1 (antibody)/PEG-Mu-KYNU combination eliminating 20% of tumors compared to 0% tumor elimination with PD1 (antibody) alone. FIG. 9C—Corresponding Kaplan-Meier plot.

FIG. 10B—Corresponding Kaplan-Meier plot depicting a median survival time of 25 days for PEG-Mu-KYNU (---), and median survival time of 22 days for heat-inactivated PEG-Mu-KYNU (■) (arrows indicate treatment days).

DESCRIPTION OF ILLUSTRATIVE EMBODIMENTS

Figure 1:
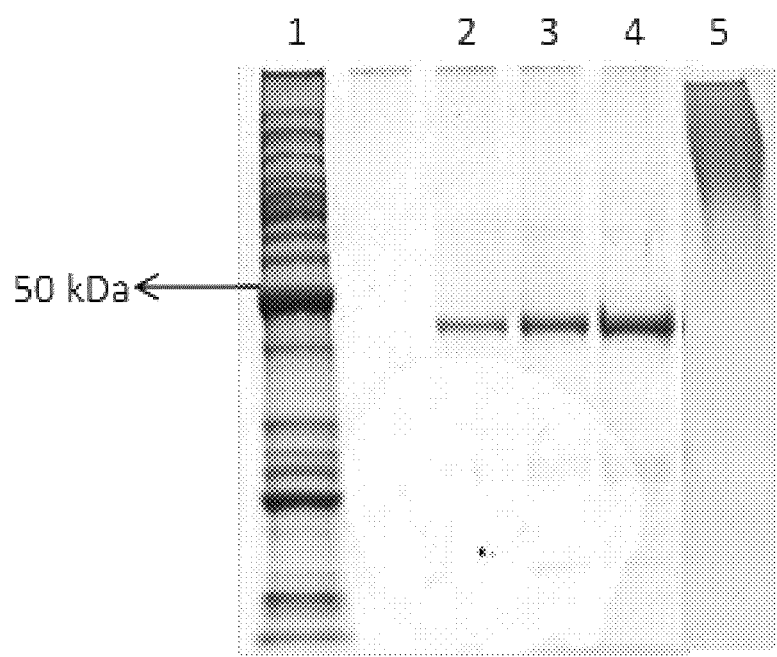
FIG. 1—SDS-PAGE of (lane 1) PRECISION PLUS PROTEIN™ MW standard (BioRad) (lanes 2-4) increasing concentrations of Pf-KYNU and (lane 5) PEG 5,000 MW modified Pf-KYNU.

Kynurenine is a metabolite of the amino acid tryptophan generated via the action of either indolamine-2,3-dioxygenase (IDO) or tryptophan-2,3-dioxygenase (TDO). Kynurenine exerts multiple effects on cell physiology, one of the most important of which is modulation of T cell responses. Many tumor cells regulate the synthesis of IDO and/or TDO to elevate the local concentration of kynurenine, which is accompanied with depletion of tryptophan. High levels of kynurenine serve as a powerful way to inhibit the function of tumor infiltrating T cells that would otherwise attack the tumor.

The present invention provides methods for the use of kynurenine degrading enzymes as a means for depleting local kynurenine levels in the tumor microenvironment as well as in the serum and thus prevent tumor-mediated suppression of T-cell action. Kynurenine hydrolyzing enzymes (kynureninases) convert kynurenine to alanine and anthranilic acid, the latter of which is not known to affect T-cell function. The inventors generated a pharmaceutical preparation of kynureninase enzyme to enable the enzyme to persist for prolonged times under physiological conditions. The inventors then showed that intratumoral administration of the enzyme results in dramatic retardation of growth of an aggressive tumor in mice.

I. DEFINITIONS

As used herein the terms "protein" and "polypeptide" refer to compounds comprising amino acids joined via peptide bonds and are used interchangeably.

As used herein, the term "fusion protein" refers to a chimeric protein containing proteins or protein fragments operably linked in a non-native way.

As used herein, the term "half-life" (½-life) refers to the time that would be required for the concentration of a polypeptide thereof to fall by half in vitro or in vivo, for example, after injection in a mammal.

The terms "in operable combination," "in operable order," and "operably linked" refer to a linkage wherein the components so described are in a relationship permitting them to function in their intended manner, for example, a linkage of nucleic acid sequences in such a manner that a nucleic acid molecule capable of directing the transcription of a given gene and/or the synthesis of desired protein molecule, or a linkage of amino acid sequences in such a manner so that a fusion protein is produced.

The term "linker" is meant to refer to a compound or moiety that acts as a molecular bridge to operably link two different molecules, wherein one portion of the linker is operably linked to a first molecule, and wherein another portion of the linker is operably linked to a second molecule.

The term "PEGylated" refers to conjugation with polyethylene glycol (PEG), which has been widely used as a drug carrier, given its high degree of biocompatibility and ease of modification. PEG can be coupled (e.g., covalently linked) to active agents through the hydroxy groups at the end of the PEG chain via chemical methods; however, PEG itself is limited to at most two active agents per molecule. In a different approach, copolymers of PEG and amino acids have been explored as novel biomaterial that would retain the biocompatibility of PEG, but that would have the added advantage of numerous attachment points per molecule (thus providing greater drug loading), and that can be synthetically designed to suit a variety of applications.

The term "gene" refers to a DNA sequence that comprises control and coding sequences necessary for the production of a polypeptide or precursor thereof. The polypeptide can be encoded by a full-length coding sequence or by any portion of the coding sequence so as the desired enzymatic activity is retained.

The term "native" refers to the typical form of a gene, a gene product, or a characteristic of that gene or gene product when isolated from a naturally occurring source. A native form is that which is most frequently observed in a natural population and is thus arbitrarily designated the normal or wild-type form. In contrast, the term "modified," "variant," or "mutant" refers to a gene or gene product that displays modification in sequence and functional properties (i.e., altered characteristics) when compared to the native gene or gene product.

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for an RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

The term "therapeutically effective amount" as used herein refers to an amount of cells and/or therapeutic composition (such as a therapeutic polynucleotide and/or therapeutic polypeptide) that is employed in methods to achieve a therapeutic effect. The term "therapeutic benefit" or "therapeutically effective" as used throughout this application refers to anything that promotes or enhances the well-being of the subject with respect to the medical treatment of this condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, or prevention of metastasis. Treatment of cancer may also refer to prolonging survival of a subject with cancer.

The term "$K_M$" as used herein refers to the Michaelis-Menten constant for an enzyme and is defined as the concentration of the specific substrate at which a given enzyme yields one-half its maximum velocity in an enzyme catalyzed reaction. The term "$k_{cat}$" as used herein refers to the turnover number or the number of substrate molecules each enzyme site converts to product per unit time, and in which the enzyme is working at maximum efficiency. The term "$k_{cat}/K_M$" as used herein is the specificity constant, which is a measure of how efficiently an enzyme converts a substrate into product.

The term "chimeric antigen receptors (CARs)," as used herein, may refer to artificial T-cell receptors, chimeric T-cell receptors, or chimeric immunoreceptors, for example, and encompass engineered receptors that graft an artificial specificity onto a particular immune effector cell. CARs may be employed to impart the specificity of a monoclonal antibody onto a T cell, thereby allowing a large number of specific T cells to be generated, for example, for use in adoptive cell therapy. In specific embodiments, CARs direct specificity of the cell to a tumor associated antigen, for example. In some embodiments, CARs comprise an intracellular activation domain, a transmembrane domain, and an extracellular domain comprising a tumor associated antigen binding region. In particular aspects, CARs comprise fusions of single-chain variable fragments (scFv) derived from monoclonal antibodies (such as those described in U.S. Pat. No. 7,109,304, which is incorporated herein by reference in its entirety), fused to CD3-zeta transmembrane and endodomains. The specificity of other CAR designs may be derived from ligands of receptors (e.g., peptides) or from pattern-recognition receptors, such as Dectins. In particular embodiments, one can target malignant B cells by redirecting the specificity of T cells by using a CAR specific for the B-lineage molecule, CD19. In certain cases, the spacing of the antigen-recognition domain can be modified to reduce activation-induced cell death. In certain cases, CARs comprise domains for additional co-stimulatory signaling, such as CD3-zeta, FcR, CD27, CD28, CD137, DAP10, and/or OX40. In some cases, molecules can be co-expressed with the CAR, including co-stimulatory molecules, reporter genes for imaging (e.g., for positron emission tomography), gene products that conditionally ablate the T cells upon addition of a pro-drug, homing receptors, chemokines, chemokine receptors, cytokines, and cytokine receptors.

"Treatment" and "treating" refer to administration or application of a therapeutic agent to a subject or performance of a procedure or modality on a subject for the purpose of obtaining a therapeutic benefit of a disease or health-related condition. For example, a treatment may include administration of a pharmaceutically effective amount of a kynureninase.

"Subject" and "patient" refer to either a human or non-human, such as primates, mammals, and vertebrates. In particular embodiments, the subject is a human.

II. KYNURENINASE POLYPEPTIDES

Some embodiments concern modified proteins and polypeptides. Particular embodiments concern a modified protein or polypeptide that exhibits at least one functional activity that is comparable to the unmodified version, preferably, the kynurenine degrading activity or the 3'-hydroxy-kynurenine degrading activity. In further aspects, the protein or polypeptide may be further modified to increase serum stability. Thus, when the present application refers to the function or activity of "modified protein" or a "modified polypeptide," one of ordinary skill in the art would understand that this includes, for example, a protein or polypeptide that possesses an additional advantage over the unmodified protein or polypeptide, such as kynurenine degrading activity or 3'-hydroxy-kynurenine degrading activity. In certain embodiments, the unmodified protein or polypeptide is a native kynureninase, preferably a human kynureninase or the *Pseudomonas fluorescens* kynureninase. It is specifically contemplated that embodiments concerning a "modified protein" may be implemented with respect to a "modified polypeptide," and vice versa.

Determination of activity may be achieved using assays familiar to those of skill in the art, particularly with respect to the protein's activity, and may include for comparison purposes, the use of native and/or recombinant versions of either the modified or unmodified protein or polypeptide.

In certain embodiments, a modified polypeptide, such as a modified kynureninase, may be identified based on its increase in kynurenine and/or 3'-hydroxy-kynurenine degrading activity. For example, substrate recognition sites of the unmodified polypeptide may be identified. This identification may be based on structural analysis or homology analysis. A population of mutants involving modifications of such substrate recognition sites may be generated. In a further embodiment, mutants with increased kynurenine degrading activity may be selected from the mutant population. Selection of desired mutants may include methods, such as detection of byproducts or products from kynurenine degradation.

Modified proteins may possess deletions and/or substitutions of amino acids; thus, a protein with a deletion, a protein with a substitution, and a protein with a deletion and a substitution are modified proteins. In some embodiments, these modified proteins may further include insertions or added amino acids, such as with fusion proteins or proteins with linkers, for example. A "modified deleted protein" lacks one or more residues of the native protein, but may possess the specificity and/or activity of the native protein. A "modified deleted protein" may also have reduced immunogenicity or antigenicity. An example of a modified deleted protein is one that has an amino acid residue deleted from at least one antigenic region that is, a region of the protein determined to be antigenic in a particular organism, such as the type of organism that may be administered the modified protein.

Substitution or replacement variants typically contain the exchange of one amino acid for another at one or more sites within the protein and may be designed to modulate one or more properties of the polypeptide, particularly its effector functions and/or bioavailability. Substitutions may or may not be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine, or methionine; serine to threonine; threonine to serine; tryptophan to tyrosine; tyrosine to tryptophan or phenylalanine; and valine to isoleucine or leucine.

In addition to a deletion or substitution, a modified protein may possess an insertion of residues, which typically involves the addition of at least one residue in the polypeptide. This may include the insertion of a targeting peptide or polypeptide or simply a single residue. Terminal additions, called fusion proteins, are discussed below.

The term "biologically functional equivalent" is well understood in the art and is further defined in detail herein. Accordingly, sequences that have between about 70% and about 80%, or between about 81% and about 90%, or even between about 91% and about 99% of amino acids that are identical or functionally equivalent to the amino acids of a control polypeptide are included, provided the biological activity of the protein is maintained. A modified protein may be biologically functionally equivalent to its native counterpart in certain aspects.

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

III. ENZYMATIC KYNURENINE DEGRADATION FOR THERAPY

In certain aspects, the polypeptides may be used for the treatment of diseases, including cancers that are sensitive to kynurenine depletion, with enzymes that deplete kynurenine, to prevent tumor-mediated tolerogenic effects and instead mediate tumor-ablating pro-inflammatory responses. In certain aspects, kynureninases are contemplated for use in treating tumors expressing IDO1, IDO2, and/or TDO.

Certain aspects of the present invention provide a modified kynureninase for treating diseases, such as tumors. Particularly, the modified polypeptide may have human polypeptide sequences and thus may prevent allergic reactions in human patients, allow repeated dosing, and increase the therapeutic efficacy.

Tumors for which the present treatment methods are useful include any malignant cell type, such as those found in a solid tumor or a hematological tumor. Exemplary solid tumors can include, but are not limited to, a tumor of an organ selected from the group consisting of pancreas, colon, cecum, stomach, brain, head, neck, ovary, kidney, larynx, sarcoma, lung, bladder, melanoma, prostate, and breast. Exemplary hematological tumors include tumors of the bone marrow, T or B cell malignancies, leukemias, lymphomas, blastomas, myelomas, and the like. Further examples of cancers that may be treated using the methods provided herein include, but are not limited to, carcinoma, lymphoma, blastoma, sarcoma, leukemia, squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer and gastrointestinal stromal cancer), pancreatic cancer, glioblastoma, cervical cancer, ovarian cancer, liver cancer, bladder cancer, breast cancer, colon cancer, colorectal cancer, endometrial or uterine carcinoma, salivary gland carcinoma, kidney or renal cancer, prostate cancer, vulval cancer, thyroid cancer, various types of head and neck cancer, melanoma, superficial spreading melanoma, lentigo malignant melanoma, acral lentiginous melanomas, nodular melanomas, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's macroglobulinemia), chronic lymphocytic leukemia (CLL), acute lymphoblastic leukemia (ALL), Hairy cell leukemia, multiple myeloma, acute myeloid leukemia (AML) and chronic myeloblastic leukemia.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epitheloid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The kynureninase may be used herein as an antitumor agent in a variety of modalities for depleting kynurenine and/or 3'-hydroxy-kynurenine from tumor tissue, or the circulation of a mammal with cancer, or for depletion of kynurenine where its depletion is considered desirable.

Depletion can be conducted in vivo in the circulation of a mammal, in vitro in cases where kynurenine and 3'-hydroxy-kynurenine depletion in tissue culture or other biological mediums is desired, and in ex vivo procedures where biological fluids, cells, or tissues are manipulated outside the body and subsequently returned to the body of the patient mammal. Depletion of kynurenine from circulation, culture media, biological fluids, or cells is conducted to reduce the amount of kynurenine accessible to the material being treated, and therefore comprises contacting the material to be depleted with a kynurenine-depleting amount of the kynureninase under kynurenine-depleting conditions as to degrade the ambient kynurenine in the material being contacted.

The depletion may be directed to the nutrient source for the cells, and not necessarily the cells themselves. Therefore, in an in vivo application, treating a tumor cell includes contacting the nutrient medium for a population of tumor cells with the kynureninase. In this embodiment, the medium may be blood, lymphatic fluid, spinal fluid and the like bodily fluid where kynurenine depletion is desired.

Kynurenine- and 3'-hydroxy-kynurenine-depleting efficiency can vary widely depending upon the application, and typically depends upon the amount of kynurenine present in the material, the desired rate of depletion, and the tolerance of the material for exposure to kynureninase. Kynurenine and kynurenine metabolite levels in a material, and therefore rates of kynurenine and kynurenine metabolite depletion from the material, can readily be monitored by a variety of chemical and biochemical methods well known in the art. Exemplary kynurenine-depleting amounts are described further herein, and can range from 0.001 to 100 units (U) of kynureninase, preferably about 0.01 to 10 U, and more preferably about 0.1 to 5 U kyureninase per milliliter (mL) of material to be treated. Typical dosages can be administered based on body weight, and are in the range of about 5-1000 U/kilogram (kg)/day, preferably about 5-100 U/kg/day, more preferably about 10-50 U/kg/day, and more preferably about 20-40 U/kg/day.

Kynurenine-depleting conditions are buffer and temperature conditions compatible with the biological activity of a kynureninase, and include moderate temperature, salt, and pH conditions compatible with the enzyme, for example, physiological conditions. Exemplary conditions include about 4-40° C., ionic strength equivalent to about 0.05 to 0.2 M NaCl, and a pH of about 5 to 9, while physiological conditions are included.

In a particular embodiment, the invention contemplates methods of using a kynureninase as an antitumor agent, and therefore comprises contacting a population of tumor cells with a therapeutically effective amount of kynureninase for a time period sufficient to inhibit tumor cell growth.

In one embodiment, the contacting in vivo is accomplished by administering, by intravenous intraperitoneal, or intratumoral injection, a therapeutically effective amount of a physiologically tolerable composition comprising an kynureninase of this invention to a patient, thereby depleting the kynurenine source of the tumor cells present in the patient.

A therapeutically effective amount of a kynureninase is a predetermined amount calculated to achieve the desired effect, i.e., to deplete kynurenine in the tumor tissue or in a patient's circulation, and thereby mediate a tumor-ablating pro-inflammatory response. Thus, the dosage ranges for the administration of kynureninase of the invention are those large enough to produce the desired effect in which the symptoms of tumor cell division and cell cycling are reduced. The dosage should not be so large as to cause adverse side effects, such as hyperviscosity syndromes, pulmonary edema, congestive heart failure, neurological effects, and the like. Generally, the dosage will vary with age of, condition of, sex of, and extent of the disease in the patient and can be determined by one of skill in the art. The dosage can be adjusted by the individual physician in the event of any complication.

The kynureninase can be administered parenterally by injection or by gradual infusion over time. The kynureninase can be administered intravenously, intraperitoneally, orally, intramuscularly, subcutaneously, intracavity, transdermally, dermally, can be delivered by peristaltic means, can be injected directly into the tissue containing the tumor cells, or can be administered by a pump connected to a catheter that may contain a potential biosensor for kynurenine.

The therapeutic compositions containing kynureninase are conventionally administered intravenously, as by injection of a unit dose, for example. The term "unit dose" when used in reference to a therapeutic composition refers to physically discrete units suitable as unitary dosage for the subject, each unit containing a predetermined quantity of active material calculated to produce the desired therapeutic effect in association with the required diluent, i.e., carrier, or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for initial administration and booster shots are also contemplated and are typified by an initial administration followed by repeated doses at one or more hour intervals by a subsequent injection or other administration. Exemplary multiple administrations are described herein and are particularly preferred to maintain continuously high serum and tissue levels of kynureninase and conversely low serum and tissue levels of kynurenine. Alternatively, continuous intravenous infusion sufficient to maintain concentrations in the blood in the ranges specified for in vivo therapies are contemplated.

IV. CONJUGATES

Compositions and methods of the present invention involve modified kynureninases, such as by forming conjugates with heterologous peptide segments or polymers, such as polyethylene glycol. In further aspects, the kynureninases may be linked to PEG to increase the hydrodynamic radius of the enzyme and hence increase the serum persistence. In certain aspects, the disclosed polypeptide may be conjugated to any targeting agent, such as a ligand having the ability to specifically and stably bind to an external receptor or binding site on a tumor cell (U.S. Patent Publ. 2009/0304666).

A. Fusion Proteins

Certain embodiments of the present invention concern fusion proteins. These molecules may have a native or modified kynureninase linked at the N- or C-terminus to a heterologous domain. For example, fusions may also employ leader sequences from other species to permit the recombinant expression of a protein in a heterologous host. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the kynureninase may be linked to a peptide that increases the in vivo half-life, such as an XTEN polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

B. Linkers

In certain embodiments, the kynureninase may be chemically conjugated using bifunctional cross-linking reagents or fused at the protein level with peptide linkers.

Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the kynureninase, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become especially popular because of their commercial availability, ease of synthesis, and the mild reaction conditions under which they can be applied.

A majority of heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine kynureninase, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used. Conventional methods to purify the fusion proteins from inclusion bodies may be useful, such as using weak detergents, such as sodium N-lauroyl-sarcosine (SLS).

C. PEGylation

In certain aspects of the invention, methods and compositions related to PEGylation of kynureninase are disclosed. For example, the kynureninase may be PEGylated in accordance with the methods disclosed herein.

PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

V. PROTEINS AND PEPTIDES

In certain embodiments, the present invention concerns novel compositions comprising at least one protein or peptide, such as a kynureninase. These peptides may be comprised in a fusion protein or conjugated to an agent as described supra.

As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide," and "peptide" are used interchangeably herein.

As used herein, an "amino acid residue" refers to any naturally occurring amino acid, any amino acid derivative, or any amino acid mimic known in the art. In certain embodiments, the residues of the protein or peptide are sequential, without any non-amino acids interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid.

Proteins or peptides may be made by any technique known to those of skill in the art, including the expression of proteins, polypeptides, or peptides through standard molecular biological techniques, the isolation of proteins or peptides from natural sources, or the chemical synthesis of proteins or peptides. The nucleotide and protein, polypeptide, and peptide sequences corresponding to various genes have been previously disclosed, and may be found at computerized databases known to those of ordinary skill in the art. One such database is the National Center for Biotechnology Information's Genbank and GenPept databases (available on the world wide web at ncbi.nlm.nih.gov/). The coding regions for known genes may be amplified and/or expressed using the techniques disclosed herein or as would be known to those of ordinary skill in the art. Alternatively, various commercial preparations of proteins, polypeptides, and peptides are known to those of skill in the art.

VI. NUCLEIC ACIDS AND VECTORS

In certain aspects of the invention, nucleic acid sequences encoding a kynureninase or a fusion protein containing a kynureninase may be disclosed. Depending on which expression system is used, nucleic acid sequences can be selected based on conventional methods. For example, if the kynureninase is derived from human kynureninase and contains multiple codons that are rarely utilized in *E. coli*, then that may interfere with expression. Therefore, the respective genes or variants thereof may be codon optimized for *E. coli* expression. Various vectors may be also used to express the protein of interest. Exemplary vectors include, but are not limited, plasmid vectors, viral vectors, transposon, or liposome-based vectors.

VII. HOST CELLS

Host cells may be any that may be transformed to allow the expression and secretion of kynureninase and conjugates thereof. The host cells may be bacteria, mammalian cells, yeast, or filamentous fungi. Various bacteria include *Escherichia* and *Bacillus*. Yeasts belonging to the genera *Saccharomyces, Kluyveromyces, Hansenula,* or *Pichia* would find use as an appropriate host cell. Various species of filamentous fungi may be used as expression hosts, including the following genera: *Aspergillus, Trichoderma, Neurospora, Penicillium, Cephalosporium, Achlya, Podospora, Endothia, Mucor, Cochliobolus,* and *Pyricularia*.

Examples of usable host organisms include bacteria, e.g., *Escherichia coli* MC1061, derivatives of *Bacillus subtilis* BRB1 (Sibakov et al., 1984), *Staphylococcus aureus* SAI123 (Lordanescu, 1975) or *Streptococcus lividans* (Hopwood et al., 1985); yeasts, e.g., *Saccharomyces cerevisiae* AH 22 (Mellor et al., 1983) or *Schizosaccharomyces pombe*; and filamentous fungi, e.g., *Aspergillus nidulans, Aspergillus awamori* (Ward, 1989), or *Trichoderma reesei* (Penttila et al., 1987; Harkki et al., 1989).

Examples of mammalian host cells include Chinese hamster ovary cells (CHO-K1; ATCC CCL61), rat pituitary cells (GH1; ATCC CCL82), HeLa S3 cells (ATCC CCL2.2), rat hepatoma cells (H-4-II-E; ATCCCRL 1548), SV40-transformed monkey kidney cells (COS-1; ATCC CRL 1650), and murine embryonic cells (NIH-3T3; ATCC CRL 1658). The foregoing being illustrative but not limitative of the many possible host organisms known in the art. In principle, all hosts capable of secretion can be used whether prokaryotic or eukaryotic.

Mammalian host cells expressing the kynureninase and/or their fusion proteins are cultured under conditions typically employed to culture the parental cell line. Generally, cells are cultured in a standard medium containing physiological salts and nutrients, such as standard RPMI, MEM, IMEM, or DMEM, typically supplemented with 5%-10% serum, such as fetal bovine serum. Culture conditions are also standard, e.g., cultures are incubated at 37° C. in stationary or roller cultures until desired levels of the proteins are achieved.

VIII. PROTEIN PURIFICATION

Protein purification techniques are well known to those of skill in the art. These techniques involve, at one level, the homogenization and crude fractionation of the cells, tissue, or organ to polypeptide and non-polypeptide fractions. The protein or polypeptide of interest may be further purified using chromatographic and electrophoretic techniques to achieve partial or complete purification (or purification to homogeneity) unless otherwise specified. Analytical methods particularly suited to the preparation of a pure peptide are ion-exchange chromatography, gel exclusion chromatography, polyacrylamide gel electrophoresis, affinity chromatography, immunoaffinity chromatography, and isoelectric focusing. A particularly efficient method of purifying peptides is fast-performance liquid chromatography (FPLC) or even high-performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various techniques suitable for use in protein purification are well known to those of skill in the art. These include, for example, precipitation with ammonium sulphate, PEG, antibodies and the like, or by heat denaturation, followed by centrifugation; chromatography steps, such as ion exchange, gel filtration, reverse phase, hydroxyapatite, and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

There is no general requirement that the protein or peptide will always be provided in its most purified state. Indeed, it is contemplated that less substantially purified products may have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

In certain embodiments a protein or peptide may be isolated or purified, for example, a kynureninase, a fusion protein containing a kynureninase, or a modified kynureninase post PEGylation. For example, a His tag or an affinity epitope may be comprised in such a kynureninase to facilitate purification. Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that does not adsorb molecules to any significant extent and that has a broad range of chemical, physical, and thermal stability. The ligand should be coupled in such a way as to not affect its binding properties. The ligand should also provide relatively tight binding. It should be possible to elute the substance without destroying the sample or the ligand.

Size exclusion chromatography (SEC) is a chromatographic method in which molecules in solution are separated based on their size, or in more technical terms, their hydrodynamic volume. It is usually applied to large molecules or macromolecular complexes, such as proteins and industrial polymers. Typically, when an aqueous solution is used to transport the sample through the column, the technique is known as gel filtration chromatography, versus the name gel permeation chromatography, which is used when an organic solvent is used as a mobile phase.

The underlying principle of SEC is that particles of different sizes will elute (filter) through a stationary phase at different rates. This results in the separation of a solution of particles based on size. Provided that all the particles are loaded simultaneously or near simultaneously, particles of the same size should elute together. Each size exclusion column has a range of molecular weights that can be separated. The exclusion limit defines the molecular weight at the upper end of this range and is where molecules are too large to be trapped in the stationary phase. The permeation limit defines the molecular weight at the lower end of the range of separation and is where molecules of a small enough size can penetrate into the pores of the stationary phase completely and all molecules below this molecular mass are so small that they elute as a single band.

High-performance liquid chromatography (or high-pressure liquid chromatography, HPLC) is a form of column chromatography used frequently in biochemistry and analytical chemistry to separate, identify, and quantify compounds. HPLC utilizes a column that holds chromatographic packing material (stationary phase), a pump that moves the mobile phase(s) through the column, and a detector that shows the retention times of the molecules. Retention time varies depending on the interactions between the stationary phase, the molecules being analyzed, and the solvent(s) used.

IX. PHARMACEUTICAL COMPOSITIONS

It is contemplated that the novel kynureninase can be administered systemically or locally to inhibit tumor cell growth and, most preferably, to kill cancer cells in cancer patients with locally advanced or metastatic cancers. They can be administered intravenously, intrathecally, and/or intraperitoneally. They can be administered alone or in combination with anti-proliferative drugs. In one embodiment, they are administered to reduce the cancer load in the patient prior to surgery or other procedures. Alternatively, they can be administered after surgery to ensure that any remaining cancer (e.g., cancer that the surgery failed to eliminate) does not survive.

It is not intended that the present invention be limited by the particular nature of the therapeutic preparation. For example, such compositions can be provided in formulations together with physiologically tolerable liquid, gel, or solid carriers, diluents, and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual subjects.

Such compositions are typically prepared as liquid solutions or suspensions, as injectables. Suitable diluents and excipients are, for example, water, saline, dextrose, glycerol, or the like, and combinations thereof. In addition, if desired, the compositions may contain minor amounts of auxiliary substances, such as wetting or emulsifying agents, stabilizing agents, or pH buffering agents.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more kynureninase or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one kyureninase isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intradermally, transdermally, intrathecally, intraarterially, intraperitoneally, intranasally, intravaginally, intrarectally, intramuscularly, subcutaneously, mucosally, orally, topically, locally, by inhalation (e.g., aerosol inhalation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of a the composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates, such as dextrose, mannose, galactose, fructose, lactose, sucrose, maltose, sorbitol, mannitol, etc.

In further embodiments, the present invention may concern the use of a pharmaceutical lipid vehicle composition that includes kynureninases, one or more lipids, and an aqueous solvent. As used herein, the term "lipid" will be defined to include any of a broad range of substances that is characteristically insoluble in water and extractable with an organic solvent. This broad class of compounds is well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether- and ester-linked fatty acids, polymerizable lipids, and combinations thereof. Of course, compounds other than those specifically described herein that are understood by one of skill in the art as lipids are also encompassed by the compositions and methods.

One of ordinary skill in the art would be familiar with the range of techniques that can be employed for dispersing a composition in a lipid vehicle. For example, the kynureninase or a fusion protein thereof may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition administered to an animal patient can be determined by physical and physiological factors, such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared in such a way that a suitable dosage will be obtained in any given unit dose of the compound. Factors, such as solubility, bioavailability, biological half-life, route of administration, product shelf life, as well as other pharmacological considerations, will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 milligram/kg/body weight or more per administration, and any range derivable therein. In non-limiting examples of a derivable range from the numbers listed herein, a range of about 5 milligram/kg/body weight to about 100 milligram/kg/body weight, about 5 microgram/kg/body weight to about 500 milligram/kg/body weight, etc., can be administered, based on the numbers described above.

X. COMBINATION TREATMENTS

In certain embodiments, the compositions and methods of the present embodiments involve administration of a kynureninase in combination with a second or additional therapy. Such therapy can be applied in the treatment of any disease that is associated with kynurenine dependency. For example, the disease may be cancer.

The methods and compositions, including combination therapies, enhance the therapeutic or protective effect, and/or increase the therapeutic effect of another anti-cancer or anti-hyperproliferative therapy. Therapeutic and prophylactic methods and compositions can be provided in a combined amount effective to achieve the desired effect, such as the killing of a cancer cell and/or the inhibition of cellular hyperproliferation. This process may involve administering a kynureninase and a second therapy. The second therapy may or may not have a direct cytotoxic effect. For example, the second therapy may be an agent that upregulates the immune system without having a direct cytotoxic effect. A tissue, tumor, or cell can be exposed to one or more compositions or pharmacological formulation(s) comprising one or more of the agents (e.g., a kynureninase or an anti-cancer agent), or by exposing the tissue, tumor, and/or cell with two or more distinct compositions or formulations, wherein one composition provides 1) a kynureninase, 2) an anti-cancer agent, or 3) both a kynureninase and an anti-cancer agent. Also, it is contemplated that such a combination therapy can be used in conjunction with chemotherapy, radiotherapy, surgical therapy, or immunotherapy.

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing, for example, both agents are delivered to a cell in a combined amount effective to kill the cell or prevent it from dividing.

A kynureninase may be administered before, during, after, or in various combinations relative to an anti-cancer treatment. The administrations may be in intervals ranging from concurrently to minutes to days to weeks. In embodiments where the kynureninase is provided to a patient separately from an anti-cancer agent, one would generally ensure that a significant period of time did not expire between the time of each delivery, such that the two compounds would still be able to exert an advantageously combined effect on the patient. In such instances, it is contemplated that one may provide a patient with the kynureninase and the anti-cancer therapy within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

In certain embodiments, a course of treatment will last 1-90 days or more (this such range includes intervening days). It is contemplated that one agent may be given on any day of day 1 to day 90 (this such range includes intervening days) or any combination thereof, and another agent is given on any day of day 1 to day 90 (this such range includes intervening days) or any combination thereof. Within a single day (24-hour period), the patient may be given one or multiple administrations of the agent(s). Moreover, after a course of treatment, it is contemplated that there is a period of time at which no anti-cancer treatment is administered. This time period may last 1-7 days, and/or 1-5 weeks, and/or 1-12 months or more (this such range includes intervening days), depending on the condition of the patient, such as their prognosis, strength, health, etc. It is expected that the treatment cycles would be repeated as necessary.

Various combinations may be employed. For the example below a kynureninase is "A" and an anti-cancer therapy is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclosphosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammaII and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that immunotherapies may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. Checkpoint inhibitors, such as, for example, ipilumimab, are another such example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739, 169; Hui and Hashimoto, 1998; Christodoulides et al., 1998); cytokine therapy, e.g., interferons α, β, and γ, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

XI. KITS

Certain aspects of the present invention may provide kits, such as therapeutic kits. For example, a kit may comprise one or more pharmaceutical composition as described herein and optionally instructions for their use. Kits may also comprise one or more devices for accomplishing administration of such compositions. For example, a subject kit may comprise a pharmaceutical composition and catheter for accomplishing direct intravenous injection of the composition into a cancerous tumor. In other embodiments, a subject kit may comprise pre-filled ampoules of a kynureninase, optionally formulated as a pharmaceutical, or lyophilized, for use with a delivery device.

Kits may comprise a container with a label. Suitable containers include, for example, bottles, vials, and test tubes. The containers may be formed from a variety of materials, such as glass or plastic. The container may hold a composition that includes a kynureninase that is effective for therapeutic or non-therapeutic applications, such as described above. The label on the container may indicate that the composition is used for a specific therapy or non-therapeutic application, and may also indicate directions for either in vivo or in vitro use, such as those described above. The kit of the invention will typically comprise the container described above and one or more other containers comprising materials desirable from a commercial and user standpoint, including buffers, diluents, filters, needles, syringes, and package inserts with instructions for use.

XII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Gene Construction, Expression, and Purification of Kynureninase from *Psuedomonas fluorescens*

A gene for expression of the kynureninase enzyme from *Pseudomonas fluorescens* (Pf-KYNU) was constructed by overlap extension polymerase chain reaction (PCR) of four codon optimized gene blocks designed using DNA-Works software (Hoover and Lubkowski, 2002). The full-length gene includes an N-terminal XbaI restriction enzyme site (nucleotides 1-6), an optimized ribosome binding site (RBS; nucleotides 29-55), a start codon (nucleotides 56-58), an N-terminal His$_6$ tag (nucleotides 59-91), an *E. coli* codon optimized Pf-KYNU gene (nucleotides 92-1336), a stop codon (nucleotides 1337-1342), and a C-terminal BamHI restriction enzyme site (nucleotides 1342-1347) (see, SEQ ID NO: 1). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an $OD_{600}$~1.0 was reached by adding IPTG (0.5 mM final concentration) with continued shaking overnight at 37° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 µg/mL DNase. Lysis was achieved by French press and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in a buffer composed of 50 mM sodium phosphate, 300 mM NaCl, and 0.1 mM PLP at pH 7.4. After loading the lysate onto the column, the resin was washed with 5 column volumes (CV) of 50 mM sodium phosphate, pH 7.4, 300 mM NaCl, and 0.1 mM PLP with 30 mM imidazole. Next, the flow rate was set to slowly wash the column overnight with 100 CV of endotoxin-free PBS (Corning) buffer with 0.1 mM PLP and 1% v/v TRITON® X114. This overnight wash removes lipopolysaccharide (LPS or endotoxin) that is a typical contaminant of bacterial expression systems. The washed enzyme was then eluted in 5 CV of endotoxin-free PBS with 0.1 mM PLP with 250 mM imidazole, and the resin was rinsed with a second 5 CV portion of endotoxin free PBS with 0.1 mM PLP. At this point, enzyme was buffer exchanged into fresh PBS to remove imidazole, 10% glycerol was added and aliquots were flash frozen in liquid nitrogen for storage at −80° C. Alternatively, enzyme was immediately buffer exchanged into freshly made, sterile 100 mM sodium phosphate, pH 8.4, to both remove imidazole and prepare it for PEGylation (see, Example 4). Enzyme purities were typically >95% based on SDS-PAGE analysis and typical yields averaged around 75 mg/L of culture. Protein quantities were assessed by measuring $Abs_{280\,nm}$ and using the calculated enzyme extinction coefficient of 63,745 $M^{-1}cm^{-1}$.

Example 2—Gene Construction, Expression, and Purification of Kynureninase from *Homo sapiens*

A gene for expression of the kynureninase enzyme from *Homo sapiens* (h-KYNU) was obtained by overlap extension polymerase chain reaction (PCR) of four codon optimized gene blocks designed using DNA-Works software (Hoover and Lubkowski, 2002). The full-length gene includes an N-terminal XbaI restriction enzyme site (nucleotides 1-6), an optimized RBS (nucleotides 28-60), a start codon (nucleotides 61-63), an N-terminal His$_6$ tag (nucleotides 64-96), an *E. coli* codon optimized h-KYNU gene (nucleotides 97-1488), a stop codon (nucleotides 1489-1491), and a C-terminal BamHI restriction enzyme site (nucleotides 1492-1497) (see, SEQ ID NO: 2). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an OD$_{600}$~1.0 was reached by adding IPTG (0.5 mM final concentration) with continued shaking overnight at 37° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 μg/mL DNase. Lysis was achieved by French press and the lysate was cleared of particulates by centrifuging at 20,000×g for 1 h at 4° C. The supernatant was then filtered through a 5 μm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 5 column volumes (CV) of 50 mM sodium phosphate, pH 7.4, 300 mM NaCl, and 0.1 mM PLP with 30 mM imidazole. Next, the flow rate was set to slowly wash the column overnight with 100 CV of endotoxin-free PBS (Corning) buffer with 0.1 mM PLP and 1% v/v TRITON® X114. This overnight wash removes lipopolysaccharide (LPS or endotoxin) that is a typical contaminant in bacterial expression of enzymes. The washed enzyme was then eluted in 5 CV of endotoxin free PBS with 0.1 mM PLP with 250 mM imidazole and the resin was rinsed with a second 5 CV portions of endotoxin free PBS with 0.1 mM PLP. At this point, enzyme was buffer exchanged into fresh PBS to remove imidazole, 10% glycerol was added and aliquots were flash frozen in liquid nitrogen for storage at −80° C. Alternatively, enzyme could be buffer exchanged into freshly made, sterile 100 mM sodium phosphate, pH 8.4, to both remove imidazole and prepare it for PEGylation (see, Example 4). Enzyme purities were typically >95% as assessed by SDS-PAGE analysis and typical yields averaged around 20 mg/L of liquid culture. Protein quantities were assessed by measuring Abs$_{280\ nm}$ and using the calculated enzyme extinction coefficient of 76,040 M$^{-1}$cm$^{-1}$.

Example 3—Gene Construction, Expression, and Purification of Kynureninase from *Mus musculus*

A gene for expression of the kynureninase enzyme from *Mus musculus* (m-KYNU) was obtained by overlap extension polymerase chain reaction (PCR) of three codon optimized gene blocks designed using DNA-Works software (Hoover et al., 2002). The full-length gene included an N-terminal XbaI restriction enzyme site (nucleotides 1-6), an optimized RBS (nucleotides 29-58), a start codon (nucleotides 59-61), an N-terminal His$_6$ tag (nucleotides 62-94), an *E. coli* codon optimized m-KYNU gene (nucleotides 95-1483), a stop codon (nucleotides 1484-1486), and a C-terminal BamHI restriction enzyme site (nucleotides 1487-1492) (see, SEQ ID NO: 3). The aforementioned restriction enzyme sites were used to clone the assembled gene into a pET-28a+ vector (Novagen). This construct was then used to transform BL21 (DE3) *E. coli* for expression. Cells were grown at 37° C. shaking at 210 rpm in Terrific Broth (TB) media with 50 mg/L of kanamycin. Expression was induced when an OD$_{600}$~1.0 was reached by adding 0.5 mM IPTG and continued overnight at 37° C. Cells were harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 μg/mL DNase. Lysis was achieved by French press and the lysate cleared of particulates by centrifuging at 20,000×g for 1 h at 4° C. The supernatant was filtered through a 5 μm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 5 column volumes (CV) of 50 mM sodium phosphate, pH 7.4, 300 mM NaCl, and 0.1 mM PLP with 30 mM imidazole. Next the flow rate was set to slowly wash overnight with 100 CV of endotoxin-free PBS (Corning) buffer with 0.1 mM PLP and 1% v/v TRITON® X114. This overnight wash removeD lipopolysaccharide (LPS or endotoxin) that is a typical contaminant in bacterial expression of enzymes. The washed enzyme was eluted in 5 CV of endotoxin-free PBS with 0.1 mM PLP with 250 mM imidazole and the resin rinsed with a second 5 CV portion of endotoxin-free PBS with 0.1 mM PLP. At this point, enzyme was buffer exchanged into fresh PBS to remove imidazole, 10% glycerol added and aliquots flash frozen in liquid nitrogen for storage at −80° C.

Example 4—Pharmacological Preparation of Kynureninase from *Pseudomonas fluorescens*

To improve the circulation time of the enzyme in vivo, the hydrodynamic radius of KYNU enzymes was increased by functionalizing surface reactive groups in the protein by conjugation to PEG. In one embodiment, Pf-KYNU was functionalized by reaction of surface lysine residues with Methoxyl PEG Succinimidyl Carbonate 5000 MW (NANOCS). The purified, endotoxin-free enzyme was thoroughly buffer exchanged into freshly prepared 100 mM sodium phosphate, pH 8.4, and concentrated to 10 mg/mL. The resulting solution was added directly to a 100:1 molar excess of solid PEG reagent and allowed to react at room temperature for 1 h (FIG. 1). Un-reacted PEG was removed from solution by thorough buffer exchange into fresh, endotoxin-free PBS in a 100 kDa cut off centrifugal filtration device (AMICON®). The apparent molecular mass of the enzyme was then checked on a size exclusion HPLC column (Phenomenex) in PBS. A MW standard solution from Bio-Rad was used to generate a standard curve and enzyme retention times compared to those of the protein standards. Based on the standard curve, the non-PEGylated enzyme has an apparent mass of 40 kDa, which is close to that of the mass of one monomer of Pf-KYNU. The PEGylated version of the enzyme was seen to have an apparent mass of 1,300 kDa, i.e. substantially larger than the unmodified enzyme. Endotoxin levels were quantified using the Chromo-LAL kinetic chromogenic endotoxin testing kit (Associates of Cape Cod, Inc.). Enzyme washed in the manner described above typically resulted in endotoxin levels 0.19±0.07 EU/mg of purified Pf-KYNU.

Example 5—Pharmacological Preparation of Kynureninase from *Homo sapiens*

To improve circulatory residence time of the human enzyme in vivo, the hydrodynamic radius of h-KYNU was increased by functionalizing surface reactive groups in the protein by conjugation to PEG. In one embodiment, h-KYNU was functionalized by reaction of surface lysine residues with Methoxyl PEG Succinimidyl Carbonate 5000 MW (NANOCS). The purified, endotoxin-free enzyme was thoroughly buffer exchanged into freshly prepared 100 mM sodium phosphate, pH 8.4, and concentrated to 10 mg/mL. The resulting solution was added directly to a 100:1 molar excess of solid PEG reagent and allowed to react at room temperature for 1 h. Un-reacted PEG was removed from solution by thorough buffer exchange into fresh, endotoxin-free PBS in a 100 kDa cut off centrifugal filtration device (AMICON®). The apparent molecular mass of the enzyme was determined using a size exclusion HPLC column (Phenomenex) equilibrated with PBS and retention times compared to a MW standard solution (BioRad). Endotoxin levels were quantified using the Chromo-LAL kinetic chromogenic endotoxin testing kit (Associates of Cape Cod, Inc.).

Example 6—Assay for Measuring Kinetic Parameters of Kynureninase

The kinetic parameters of Pf-KYNU and h-KYNU, as well as of their PEGylated versions as described in Examples 4 and 5, were quantified by a spectrophotometric assay, in which the decay in the maximum absorbance of the enzyme substrate, L-kynurenine, was monitored as a function of time. L-kynurenine solutions were prepared in a PBS buffer, pH 7.4, to result in final concentrations ranging from 8 µM to 250 µM. L-Kynurenine has an extinction coefficient of 4,500 $M^{-1}cm^{-1}$ with a $\lambda_{max}$ at 365 nm while the products of the kynureninase reaction, L-anthranilic acid and L-alanine, do not appreciably absorb at 365 nm. Reactions were initiated by adding and rapidly mixing enzyme solutions (~20 nM final) with the substrate solutions and monitoring the loss of substrate KYN at 25° C. by measuring $Abs_{365\ nm}$ over time. The resulting data was processed and fitted to the Michaelis-Menten equation for determining kinetic constants. The kinetics of PEGylated Pf-KYNU enzyme was measured in an identical manner. For the non-PEGylated enzyme, $k_{cat}/K_M=1.0\times10^5\ M^{-1}s^{-1}$, and for the PEGylated form, $k_{cat}/K_M=1.3\times10^5\ M^{-1}s^{-1}$. Kinetic parameters for the hydrolysis of 3-hydroxy-L-kynurenic acid were also determined as described here.

Example 7—In Vitro Stability of Kynureninase

Figure 2:
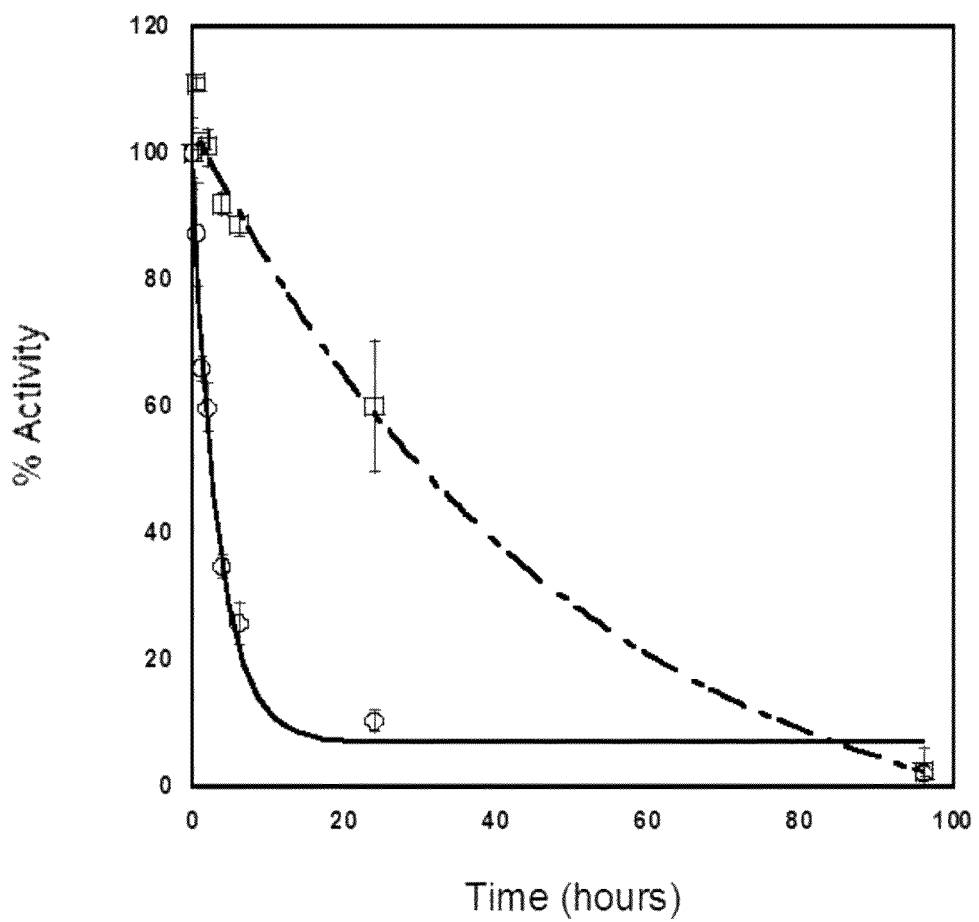
FIG. 2—Stability of Pf-KYNU in (open square) PBS and (open circle) pooled human serum.

To measure the in vitro stability of Pf-KYNU, the enzyme was added to either PBS buffer or pooled human serum to a final concentration of 10 µM and incubated at 37° C. Portions of 10 µL each were taken out at time points and added to 990 µL of a 250 µM solution of L-kynurenine/PBS. The initial rate of reaction was monitored by measuring the decay of absorbance at 365 nm over time as described in Example 3. Enzyme stability was determined by comparing the initial rate of L-kynurenine catalysis at each time point and comparing it to the rate at time=0. The resulting data was plotted as % activity vs. time and fitted to an exponential equation to determine the half-life ($T_{1/2}$). The Pf-KYNU enzyme was found to have a $T_{1/2}=34.3$ hours in PBS and a $T_{1/2}=2.4$ hours in pooled human serum (FIG. 2).

Example 8—Assay for Quantifying Kynurenine and Tryptophan Levels In Vivo

In vivo levels of L-kynurenine, tryptophan, kynureninic acid, 3-hydroxy-L-kynurenine and L-anthranlilic acid (one of the products of kynureninase catalysis) were quantified and monitored by HPLC. Upon necropsy of the mice, samples of blood, the tumor, the spleen, and the liver were removed. Blood samples were centrifuged to separate whole blood from serum. Tissue samples were first homogenized, and then centrifuged to remove the solid portion. To each liquid portion was added a 1:10 v/v portion of 100% trichloroacetic acid to precipitate macromolecules. Solids were again removed by centrifuging and the supernatants were passed through a 0.45 µm syringe filter. The treated supernatants were applied directly to a HPLC (Shimadzu) and separated on a standard analytical C-18 column using a gradient starting from 0% solution B to 100% solution B where solution A is $H_2O+0.1\%$ trifluoroacetic acid and solution B is acetonitrile+0.1% trifluoroacetic acid. The full absorbance range from 190 nm to 900 nm was continually collected to monitor all possible molecules and fluorescence spectroscopy (Ex=365 nm, Em=480 nm) was simultaneously collected to specifically monitor kynurenine levels. Concentrations and retention times were determined using standard solutions made from the pure molecules (Sigma).

Example 9—Efficacy of PEG-Pf-KYNU in the Autologous B16 Mouse Melanoma Model

Figure 3:
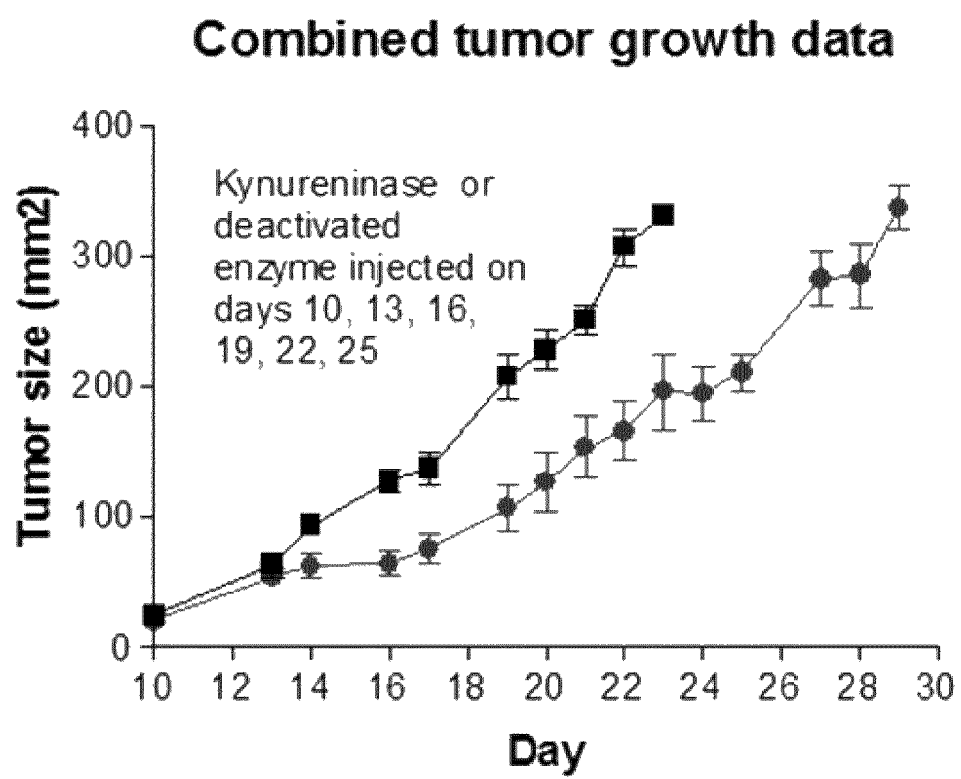
FIG. 3—Efficacy of PEG-Pf-KYNU in an autologous B16 mouse melanoma model as measured by tumor growth rates. (Solid square) Heat inactivated PEG-Pf-KYNU. (Solid circle) Active PEG-Pf-KYNU.
Figure 4:
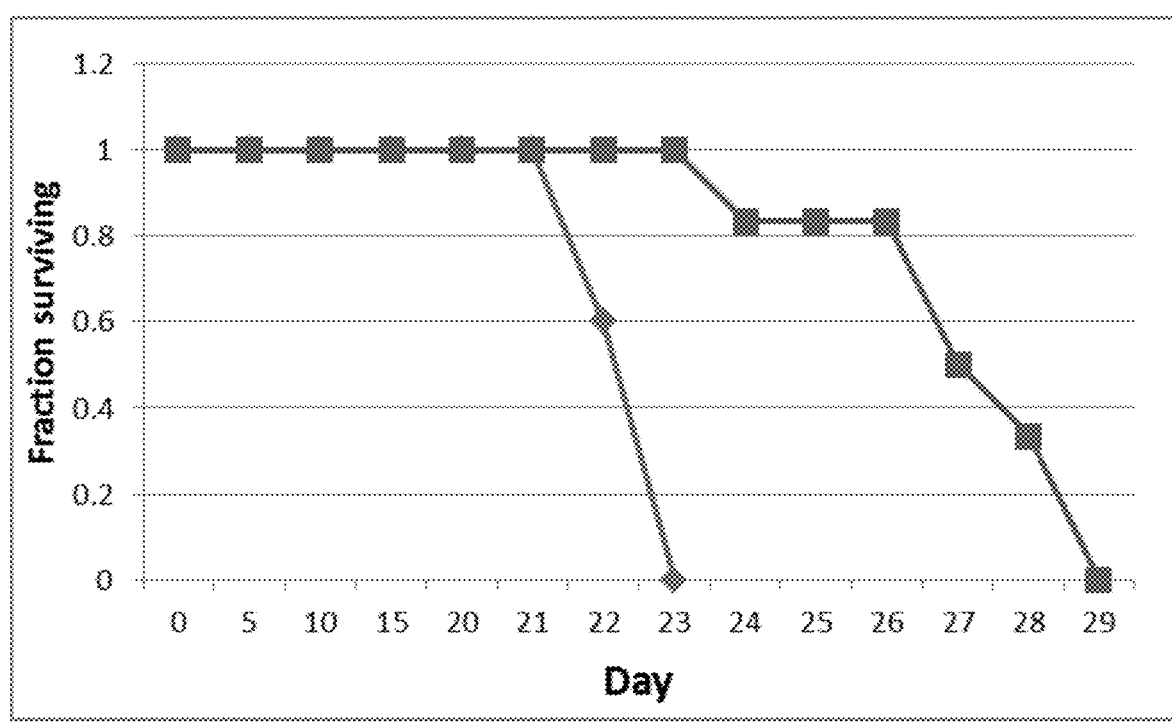
FIG. 4 Efficacy of PEG-Pf-KYNU in an autologous B16 mouse melanoma model as measured by survival. (Solid diamond) Heat inactivated PEG-Pf-KYNU. (Solid square) Active PEG-Pf-KYNU.
Figures 5A, 5B:
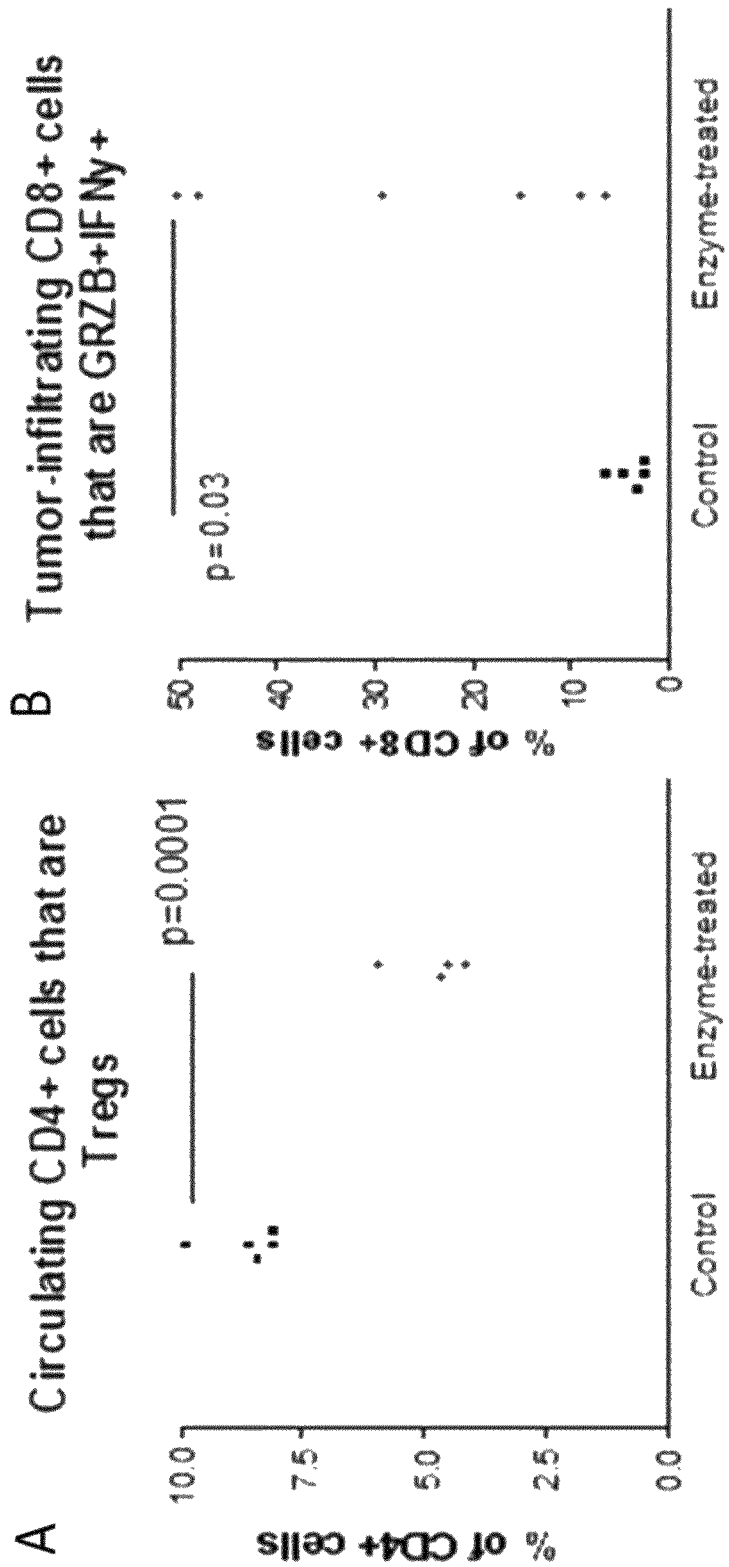
FIGS. 5A-5B—Mice treated with heat-inactivated PEG-Pf-KYNU. (•) Mice treated with active PEG-Pf-KYNU.

B6-WT mice (n=20) were each inoculated with $2.5\times10^5$ B16 murine melanoma cells by subcutaneous flank injection. After allowing tumors to establish for 10 days (tumor mean=20 mm²) the mice were split into two groups of n=10 each. The control group was then treated with 20 mg/kg of heat inactivated PEG-Pf-KYNU by intra-tumoral injection every three days until tumors reached 350 mm² in size. The experimental group was treated in an identical manner except with 20 mg/kg of active PEG-Pf-KYNU by intra-tumoral injection every three days until tumors reached an endpoint of 350 mm² in size. The growth rates of B16 melanoma tumors was significantly retarded in the treatment group administered active PEG-Pf-KYNU compared to the identically treated heat-inactivated PEG-Pf-KYNU group (FIG. 3) resulting in a significant life-span extension (FIG. 4). Lymphocytes isolated from control and experimental treatment groups were assessed with panels of antibodies (i.e., anti-CD45, CD4, Nk1.1, CD25, FoxP3, CD8, granzyme B, IFNγ, CTLA4, CD11c, CD11b, F4/80, GR-1, and Ly6-C) which revealed that the population of circulating CD4+ CD25+ FoxP3+ regulatory T-cells was significantly lower in the group treated with active PEG-Pf-KYNU (4.8±0.8% vs. 8.6±0.8%). In addition, the population of tumor infiltrating CD8+ T-cells expressing granzyme B and interferon γ was significantly higher in mice treated with active enzyme (26±19% vs. 4±2%) (FIGS. 5A-B).

Example 10—Kynureninase-scFv Fusion Proteins for Tumor Targeting

In some aspects, the present invention also contemplates polypeptides comprising the modified bacterial or mammalian kynureninase linked to a heterologous amino acid sequence. For example, the native or modified kynureninase may be linked to a single-chain variable fragment (scFv) antibody that binds specific cell surface tumor antigens. In this embodiment an scFv-kynureninase fusion protein with the scFv portion of the protein having specific affinity for a known tumor antigen, preferably a tumor specific antigen that internalizes at a slower rate, e.g., MUC-1, would allow the kynureninase portion of the fusion protein to be delivered to the tumor cell and degrade KYN. One example would be a scFv-kynureninase fusion protein where the scFv portion targets and binds to the human epidermal growth factor receptor 2 (HER2) that is upregulated in certain types of breast cancer.

In this embodiment a native or modified kynureninase-anti-HER2-scFV fusion protein would act to target and concentrate kynureninase directly to the tumor surface and act to degrade tumor-produced KYN.

Example 11—Kynureninase-Anti-CTLA4-scFv Fusion Proteins

In some aspects, the present invention also contemplates polypeptides comprising the modified bacterial or mammalian kynureninase linked to a heterologous amino acid sequence. For example, the native or modified kynureninase may be linked to a single-chain variable fragment (scFv) antibody that binds the Cytotoxic T-Lymphocyte Antigen 4 (CTLA-4) receptor, Programmed Cell Death 1 (PD-1), or Programmed Cell Death Ligand 1 (PD-L1). A blockade of CTLA-4, PD-1, or PD-L1 by an antagonizing antibody or antibody fragment allows the inhibitory T-cell signal to be reversed allowing CD28 to stimulate T-cell activation. In this embodiment a native or modified kynureninase-anti-CTLA4-, anti-PD-1-, or anti-PD-L1-scFv fusion protein would act to remove both inhibitory protein:protein interaction signaling and inhibitory kynurenine signaling. This embodiment of a native or modified kynureninase-scFv fusion protein would be expected to potently upregulate T-cell activation and promote robust anti-tumoral responses.

Example 12—Chimeric Antigen Receptor Constructs for Delivery of Kynureninase to T Cells In some aspects, the present invention also contemplates a lentiviral vector suitable for transfection of T cells with chimeric antigen receptor (CAR) constructs such that a modified bacterial or mammalian kynureninase would be co-expressed in addition to the CAR construct. CAR constructs are proteins containing an extracellular antigen binding domain fused to a transmembrane and cytoplasmic signaling domain from a CD3-ζ chain and often a CD28 molecule (Ahmed et al., 2010). The antigen binding domain may be an scFv designed to bind an antigen expressed by a tumor cell with examples being HER2 expressed by glioblastoma or osteosarcoma, CD19 or CD20 expressed by various B-cell malignancies, or GD2 expressed by neuroblastoma (Lipowska-Bhalla et al., 2012) or any other relevant target. In this embodiment the lentiviral vector, delivering an appropriate CAR construct to a T cell, would in addition co-express a native or modified bacterial or mammalian kynureninase in the cytosol. The T cell containing this CAR/kynureninase construct would have the dual ability to 1) bind to specific tumor cells and 2) to degrade KYN, preventing KYN induction of a regulatory phenotype and or apoptosis. In another embodiment a T cell would express a CAR construct that binds a CD19+ or CD20+ diffuse large B-cell lymphoma while co-expressing a kynureninase to degrade the high concentrations of KYN often produced by this tumor type (Yoshikawa et al., 2010; de Jong et al., 2011; Yao et al., 2011).

Example 13—Genetic Selection for Kynureninase Activity

The amino acid L-tryptophan (L-Trp) is synthesized from the pentose derived precursor, chorismate, by expression of the trp biosynthetic genes. In bacteria such as *E. coli* the trp biosynthetic genes are organized in an operon composed of five genes; trpE, trpD, trpC, trpB, and trpA. The TrpE and TrpD proteins are components of the anthranilate synthase complex that catalyzes the first step in the conversion of chorismate and L-glutamine to anthranilic acid and L-glutamate. Anthranilic acid is then subsequently converted to L-Trp by the action of TrpC, TrpA, and TrpB. Cells lacking a functional anthranilate synthase gene are auxotrophic for L-Trp and cannot grow in minimal media without tryptophan. The inventors postulated that since kynurenine can be transported into the cytosol of many organisms, cells expressing recombinant L-kynureninase enzymes displaying a sufficiently high catalytic activity should be able to convert cytosolic L-kynurenine to anthranilic acid and the latter then enables the synthesis of L-Trp. By contrast, cells that do not express the enzyme or express variants with low catalytic activity should display either no growth or very slow growth, respectively, on minimal media with L-kynurenine.

Figure 6:
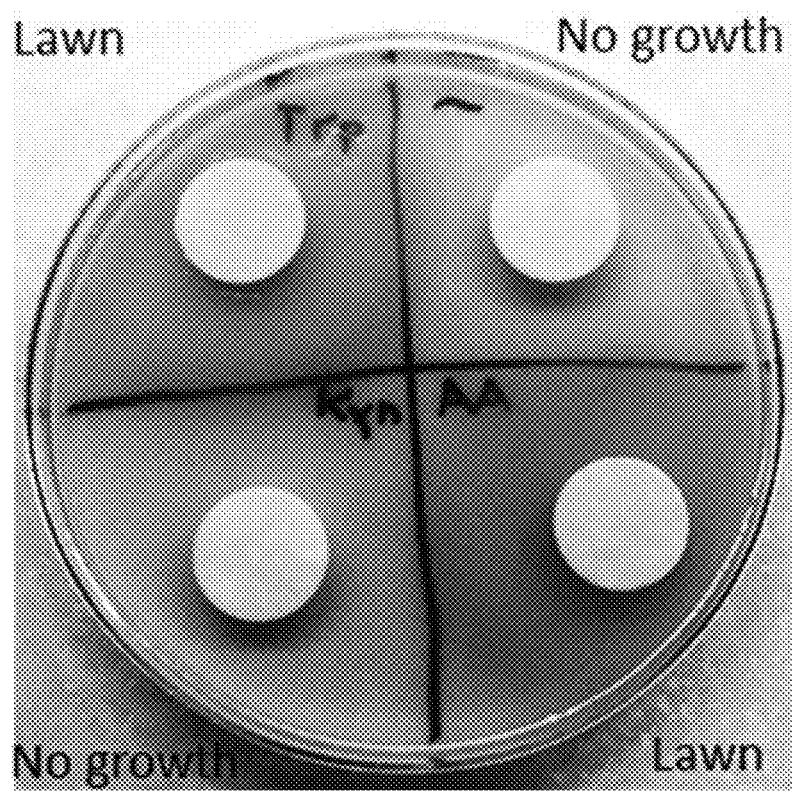
FIG. 6—Genetic selection for kynureninase activity in *E. coli*. *E. coli*-ΔtrpE cells plated on M9 minimal media plates with filter paper disks soaked in L-Trp (Trp), buffer (-), anthranilic acid (AA), or L-Kyn (Kyn).

*E. coli* trpE and trpD deletion mutants were obtained from Genetic Resources at Yale CGSC. Strain genotypes were (F-, Δ(araD-araB)567, ΔlacZ4787(::rrnB-3), λ-, ΔtrpE772::kan, rph-1, Δ(rhaD-rhaB)568, hsdR514) and (F-, Δ(araD-araB)567, ΔlacZ4787(::rrnB-3), λ-, λtrpD771::kan, rph-1, Δ(rhaD-rhaB)568, hsdR514), respectively. Cells were plated on M9 minimal media plates. Filter paper disks soaked in either L-Trp, L-Kyn, anthranilic acid, or buffer were then placed on the plates followed by incubation at 37° C. *E. coli*-ΔtrpD cells only grew in the presence of L-Trp, however *E. coli*-ΔtrpE could also grow in the presence of anthranilic acid but not buffer or L-Kyn, demonstrating that trpC, trpA, and trpB were expressed, allowing rescue of the L-Trp auxotrophy with anthranilic acid as an intermediate metabolite (FIG. 6). Furthermore, *E. coli*-ΔtrpE cells transformed with a plasmid harboring the Pf-KYNU gene grew robustly on M9 minimal media plates in the presence of L-Kyn.

Example 14—Gene Construction, Expression and Purification of Bacterial Kynureninases Displaying High Catalytic Activity Towards Kynurenine and Identity to the Human Kynureninase Similar to other eukaryotic kynureninases the *Homo sapiens* enzyme is highly selective towards the hydrolysis of 3'-OH kynurenine and has about 1,000-fold lower catalytic activity towards kynurenine. Because of its poor catalytic activity towards kynurenine, the human enzyme is not suitable for therapeutic purposes. Administration of PEGylated Pf-KYNU (Example 9), Mu-KYNU (Example 22 and Example 23), or Cp-KYNU (Example 17) (all of which display high catalytic activity towards kynurenine instead of 3'-OH kynurenine) resulted in tumor growth retardation as shown in Example 9 (FIG. 3). However, administration of PEGylated human kynureninase at similar or higher dosing had no effect on the growth of B16 melanoma tumors (n=4). However, as shown in Example 20, engineering of h-KYNU can improve the L-kynurenine degrading activity of the human enzyme. Such engineered h-KYNU variants may result in tumor growth retardation as seen with PEGylated Pf-KYNU (Example 9), Mu-KYNU (Example 22 and Example 23), and Cp-KYNU (Example 17).

The Pf-KYNU displays low sequence identity to its human counterpart (24% amino acid identity). Due to its low sequence identity to the human protein, Pf-KYNU may elicit adverse immune responses in patients as well as the production of neutralizing antibodies. Therefore it is important to discover kynureninase enzymes that display high catalytic activity and selectivity towards kynurenine and have a higher degree of amino acid identity to the *Homo sapiens* kynureninase. The inventors identified a number of bacterial enzymes that display >38% amino acid identity to the *Homo sapiens* kynureninase and also high kynurenine hydrolysis activity. The sequences of these enzymes are provided as SEQ ID NOs: 13-52. The percent identities of these enzymes as compared to *Homo sapiens* kynureninase are provided in Table 1. As a representative example, a gene for expression of the kynureninase enzyme from *Mucilaginibacter paludis* (Mu-KYNU) (SEQ ID NO: 33) was constructed by overlap extension polymerase chain reaction (PCR) of two codon optimized gene blocks designed using the DNA-Works software (Hoover and Lubkowski, 2002). The full-length gene includes an N-terminal NcoI restriction enzyme site, an optimized RBS, an N-terminal His$_6$ tag, E. coli codon optimized Mu-KYNU gene, a stop codon and a C-terminal EcoRI restriction enzyme site. The aforementioned restriction enzyme sites were used to clone the assembled gene into a pET-28a+ vector (Novagen). This construct was then used to transform BL21 (DE3) E. coli for expression. Cells were grown at 37° C. with shaking at 210 rpm in Terrific Broth (TB) media with 50 mg/L of kanamycin. Expression was induced when an OD$_{600}$~1.0 was reached by adding IPTG (0.5 mM final concentration) with continued shaking overnight at 37° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 µg/mL DNase. Lysis was achieved by French press and the lysate was cleared of particulates by centrifuging at 20,000×g for 1 h at 4° C. The supernatant was then filtered through a 5 µm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 5 column volumes (CV) of 50 mM sodium phosphate, pH 7.4, 300 mM NaCl, and 0.1 mM PLP with 30 mM imidazole. The washed enzyme was then eluted in 5 CV of PBS with 0.1 mM PLP with 250 mM imidazole. At this point, enzyme was buffer exchanged into fresh PBS to remove imidazole, 10% glycerol was added and aliquots were flash frozen in liquid nitrogen for storage at −80° C. Enzyme purities were typically >95% based on SDS-PAGE analysis and typical yields averaged around 75 mg/L of culture. Protein quantities were assessed by measuring Abs$_{280\ nm}$ and using the calculated enzyme extinction coefficient of 78,185 M$^{-1}$cm$^{-1}$.

TABLE 1

Percent identities of eubacterial kynureninase enzymes as compared to Homo sapiens kynureninase.

| Species | SEQ ID NO | % Identity |
|---|---|---|
| Arenitalea lutea | 13 | 44.1 |
| Belliella baltica DSM 15883 | 14 | 43.3 |
| Bizionia argentinensis | 15 | 42.9 |
| Candidatus Entotheonella sp. TSY2 | 16 | 44.9 |
| Candidatus Koribacter versatilis Ellin345 | 17 | 43.3 |
| Cecembia lonarensis | 18 | 45.1 |
| Chlamydia pecorum PV3056/3 | 19 | 38.2 |
| Chlamydophila caviae GPIC | 20 | 40.8 |
| Corallococcus coralloides DSM 2259 | 21 | 43 |
| Cyclobacterium marinum DSM 74 | 22 | 44.5 |
| Cystobacter fuscus | 23 | 43.5 |
| Echinicola vietnamensis DSM 17526 | 24 | 44.5 |
| Flavobacteria bacterium BBFL7 | 25 | 43.4 |
| Flexibacter litoralis DSM 6794 | 26 | 47.5 |
| Formosa sp. AK20 | 27 | 45.7 |
| Fulvivirga imtechensis | 28 | 47.1 |
| Kangiella aquimarina | 29 | 44.1 |
| Kangiella koreensis DSM 16069 | 30 | 44.3 |
| Lacinutrix sp. 5H-3-7-4 | 31 | 44.2 |
| Mariniradius saccharolyticus | 32 | 44.5 |
| Mucilaginibacter paludis | 33 | 43.9 |
| Myroides odoratimimus | 34 | 42.2 |
| Myxococcus fulvus HW-1 | 35 | 44.5 |
| Myxococcus stipitatus DSM 14675 | 36 | 44.4 |
| Myxococcus xanthus DK 1622 | 37 | 45.1 |
| Nafulsella turpanensis | 38 | 48.2 |
| Niastella koreensis GR20-10 | 39 | 44.8 |
| Nonlabens dokdonensis DSW-6 | 40 | 44 |
| Pedobacter agri | 41 | 44.1 |
| Pedobacter sp. BAL39 | 42 | 42.1 |
| Pedobacter sp. V48 | 43 | 44.1 |
| Rhodonellum psychrophilum | 44 | 45.4 |
| Salinispora arenicola | 45 | 39.1 |
| Saprospira grandis str. Lewin | 46 | 43.2 |
| Stigmatella aurantiaca DW4/3-1 | 47 | 42.5 |
| Xanthomonas axonopodis | 48 | 42 |
| Psychroflexus gondwanensis | 49 | 44 |
| Lewinella cohaerens | 50 | 45.6 |
| Lewinella persica | 51 | 44.9 |
| Pontibacter roseus | 52 | 44.8 |

Example 15—Kinetic Parameters of Mucilaginibacter paludis Kynureninase (Mu-KYNU)

The kinetic parameters of Mu-KYNU were quantified by a spectrophotometric assay, in which the decay in the maximum absorbance of the enzyme substrate, L-kynurenine, was monitored as a function of time. L-Kynurenine solutions were prepared in a PBS buffer, pH 7.4, to result in final concentrations ranging from 16 µM to 500 µM. L-Kynurenine has an extinction coefficient of 4,500 M$^{-1}$cm$^{-1}$ with a $\lambda_{max}$ at 365 nm while the products of the kynureninase reaction, L-anthranilic acid and L-alanine, do not appreciably absorb at 365 nm. Reactions were initiated by adding and rapidly mixing enzyme solutions (~20 nM final concentration) with the substrate solutions and monitoring the loss of substrate at 25° C. by measuring Abs$_{365\ nm}$ over time. The resulting data were processed and fitted to the Michaelis-Menten equation for determining kinetic constants. Mu-KYNU was determined to have a $k_{cat}/K_M$=1.2×10$^5$ M$^{-1}$s$^{-1}$.

Example 16—In Vitro Stability of Mucilaginibacter paludis Kynureninase (Mu-KYNU)

Figure 7:
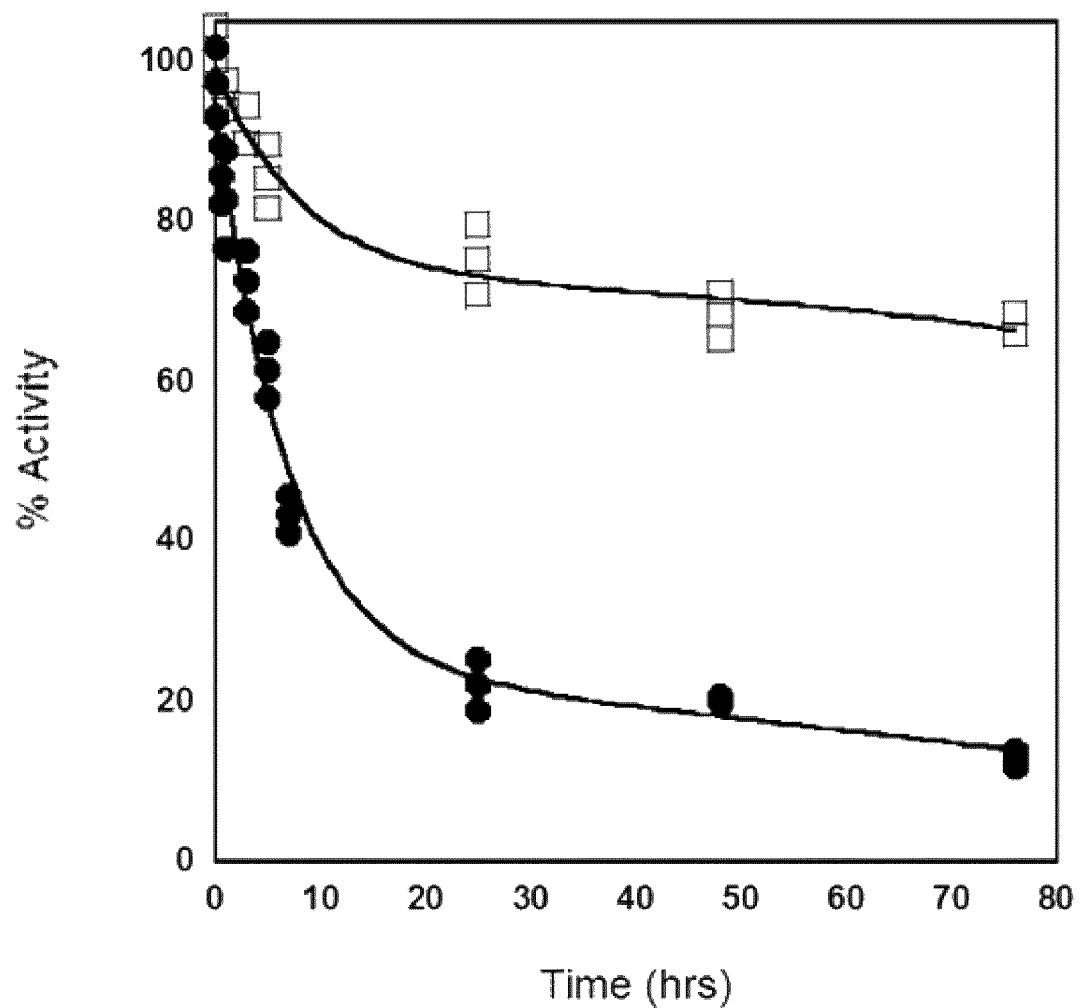
FIG. 7—In vitro stability of *Mucilaginibacter paludis* kynureninase (Mu-KYNU). Activity as a function of time of Mu-KYNU (open square) in PBS at 37° C. with a $^1T_{1/2}$=6 h with an amplitude of 74% remaining activity and a subsequent $^2T_{1/2}$=150 h, and (solid circle) in pooled human serum at 37° C. with a $^1T_{1/2}$=5 h with an amplitude of 30% remaining activity and a subsequent $^2T_{1/2}$=73 h.

To measure the in vitro stability of Mu-KYNU, the enzyme was added to either PBS buffer or pooled human serum to a final concentration of 10 µM and incubated at 37° C. Portions of 10 µL each were taken out at time points and added to 990 µL of a 250 µM solution of L-kynurenine/PBS. The initial rate of reaction was monitored by measuring the decay of absorbance at 365 nm over time as described in Example 3. Enzyme stability was determined by comparing the initial rate of L-kynurenine catalysis at each time point and comparing it to the rate at time=0. The resulting data were plotted as percent activity vs. time and fitted to a bi-phasic decay model (Stone et al., 2010) to determine the half-lives (T$_{1/2}$). The activity of Mu-KYNU enzyme in PBS was found have a $^1$T$_{1/2}$=6 h with an amplitude of 74% remaining activity and a subsequent $^2$T$_{1/2}$=150 h (FIG. 7). The stability of Mu-KYNU enzyme in pooled human serum was determined to have a $^1$T$_{1/2}$=5 h with an amplitude of 30% remaining activity and a subsequent $^2$T$_{1/2}$=73 h (FIG. 7).

Example 17—Gene Construction, Expression, and Purification of Kynureninase from Chlamydophila pecorum A gene for expression of the kynureninase enzyme from Chlamydophila pecorum (Cp-KYNU) was synthesized using *E. coli*-codon optimized gene blocks. The full-length gene includes an N-terminal NcoI restriction enzyme site (nucleotides 1-6), a start codon (nucleotides 3-5), an N-terminal His$_6$ tag (nucleotides 6-35), an *E. coli* codon optimized Cp-KYNU gene (nucleotides 36-1295), a stop codon (nucleotides 1296-1298), and a C-terminal EcoRI restriction enzyme site (nucleotides 1299-1304) (SEQ ID NO: 53). The aforementioned restriction enzyme sites were used to clone the assembled gene into a pET-28a+ vector (Novagen). This construct was then used to transform BL21 (DE3) *E. coli* for expression. Cells were grown at 37° C. with shaking at 210 rpm in Terrific Broth (TB) media with 50 mg/L of kanamycin. Expression was induced when an OD$_{600}$~1.0 was reached by adding IPTG (0.5 mM final concentration) with continued shaking overnight at 16° C. Cells were then harvested by centrifugation and re-suspended in lysis buffer consisting of 50 mM sodium phosphate, pH 7.4, 300 mM NaCl, 0.5 mM pyridoxyl phosphate (PLP), 1 mM phenylmethylsulfonylfluoride, and 1 μg/mL DNase. Lysis was achieved by French press and the lysate was cleared of particulates by centrifuging at 20,000×g for 1 h at 4° C. The supernatant was then filtered through a 5 μm syringe filter and applied to a Ni-NTA/agarose column (Qiagen) pre-equilibrated in 50 mM sodium phosphate, pH 7.4, 300 mM NaCl, and 0.1 mM PLP buffer. After loading the lysate onto the column, the resin was washed with 10 column volumes (CV) of 50 mM sodium phosphate, pH 7.4, 300 mM NaCl, and 0.1 mM PLP with 30 mM imidazole. The washed enzyme was then eluted with 5 CV of PBS containing 0.1 mM PLP and 250 mM imidazole. The eluted enzyme was buffer exchanged into fresh PBS to remove imidazole, 10% glycerol was added, and aliquots were flash frozen in liquid nitrogen for storage at −80° C.

Example 18—Kinetic Parameters of *Chlamydophila pecorum* Kynureninase (Cp-KYNU)

The kinetic parameters of Cp-KYNU (SEQ ID NO: 57) were quantified by a spectrophotometric assay, in which the decay in the maximum absorbance of the enzyme substrate, L-kynurenine, was monitored as a function of time. L-Kynurenine solutions were prepared in PBS buffer, pH 7.4, to result in final concentrations ranging from 16 μM to 500 μM. L-Kynurenine has an extinction coefficient of 4,500 M$^{-1}$cm$^{-1}$ with a $\lambda_{max}$ at 365 nm while the products of the kynureninase reaction, anthranilate and L-alanine, do not appreciably absorb at 365 nm. Reactions were initiated by adding and rapidly mixing enzyme solutions (200 nM final concentrations) with the substrate solutions and monitoring the loss of substrate at 25° C. by measuring Abs$_{365\ nm}$ over time. The resulting data were processed and fitted to the Michaelis-Menten equation for determining kinetic constants. Cp-KYNU was determined to have a $k_{cat}/K_M = 3 \times 10^4$ M$^{-1}$s$^{-1}$.

Example 19—Pharmacological Preparation of Kynureninase from *Mucilaginibacter paludis*

To improve the circulation time of the enzyme in vivo, the hydrodynamic radius of Mu-KYNU was increased by functionalizing surface reactive groups in the protein by conjugation to PEG. In one embodiment, Mu-KYNU was PEGylated by reaction of surface lysine residues with Methoxyl PEG Succinimidyl Carbonate 5000 MW (NANOCS). The purified Mu-KYNU, was determined to contain very low endotoxin levels (<20 EU/mg) as described below. It was thoroughly buffer exchanged into freshly prepared 100 mM sodium phosphate buffer, pH 8.4, and concentrated to greater than 1 mg/mL. The resultant solution was added directly to a 100:1 molar excess of solid PEG reagent and allowed to react at room temperature for 1 h with stirring. Un-reacted PEG was removed from solution by thorough buffer exchange into fresh, endotoxin-free PBS in a 100 kDa cutoff centrifugal filtration device (Amicon). The apparent molecular mass of the enzyme was then checked on a size exclusion HPLC column (Phenomenex) in PBS using a MW standard solution from BioRad to generate a standard curve, and enzyme retention times were compared to those of the protein standards. Endotoxin levels were quantified using the Chromo-LAL kinetic chromogenic endotoxin testing kit (Associates of Cape Cod, Inc.).

Example 20—Enhanced L-Kynurenine Degradation in an Engineered Human Kynureninase Variant The h-KYNU enzyme is highly selective towards the hydrolysis of 3'-OH kynurenine and has about 1,000 fold lower catalytic activity towards L-kynurenine. Because of its poor catalytic activity towards L-kynurenine, the wild-type human enzyme is not suitable for therapeutic purposes. To engineer improved L-kynurenine degrading activity into h-KYNU, a saturation mutagenesis library was constructed by overlap extension polymerase chain reaction (PCR) using the h-KYNU gene and a pair of oligonucleotides designed to introduce mutations of the codon corresponding to amino acid F306. F306 is located within the active site of h-KYNU where it appears to play a role in substrate binding. The F306 saturation library was screened for activity using the microtiter plate kynureninase assay of Example 6. More than a dozen clones displayed significantly higher activity than wild-type h-KYNU and were selected for further analysis. Sequencing of these clones revealed that two amino acid substitutions at position F306 resulted in increased L-kynurenine degrading activity, namely h-KYNU-F306M (SEQ ID NO: 55) and h-KYNU-F306L (SEQ ID NO: 56). These variants were then purified to homogeneity and a detailed kinetic analysis revealed a 2-fold and 5-fold increase in $k_{cat}/K_M$ for L-kynurenine for h-KYNU-F306M and h-KYNU-F306L, respectively, as compared to wild-type h-KYNU.

Figure 8:
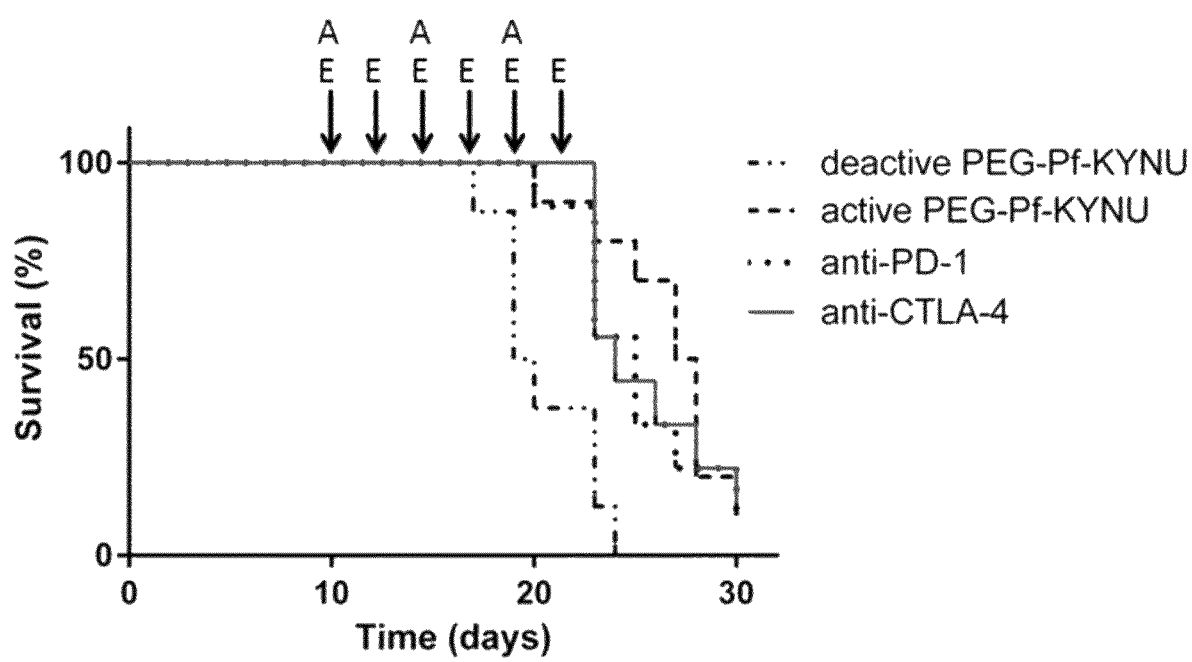
FIG. 8—Kaplan-Meier plot of B16 allografts in C57BL/6J treated with either PEG-Pf-KYNU (--●), deactivated PEG-Pf-KYNU (-●●), anti-PD1 (●●●), or anti-CTLA-4 (■). Arrows indicate treatment days, (A) indicates treatment with antibody, (E) indicates treatment with enzyme.

Example 21—Comparison of Pf-KYNU, Anti-PD1, and Anti-CTLA-4 Therapies in the Autologous B16 Mouse Melanoma Model The PEGylated *Pseudomonas fluorescence* kynureninase (PEG-Pf-KYNU) was evaluated in the B16 melanoma mouse model in a side-by-side comparison with the anti-PD1 (clone RMP1-14, BioXCell # BE0146) or anti-CTLA-4 (clone UC10-4F10-11, BioXCell # BE0032) immune checkpoint inhibitor antibodies. Fifty thousand B16 cells were implanted in the flank of C57BL/6J mice (Day 0, n=8 mice each group). Once palpable tumors developed (Day 10), the animals were treated with either 250 μg anti-PD1, 100 μg anti-CTLA-4 (200 μg 1$^{st}$ dose as per Holmgaard et al. (2013)), or 500 μg of PEG-Pf-KYNU at the times shown (FIG. 8). Heat-inactivated PEG-Pf-KYNU was used as a control. Administration of PEG-Pf-KYNU resulted in significant tumor growth retardation and extended survival in a manner indistinguishable from that observed with the anti-PD1 or anti-CTLA-4 checkpoint inhibitor antibodies (FIG. 8) for PEG-Pf-KYNU vs. inactivated enzyme or PBS only.

Figures 9A, 9B, 9C:
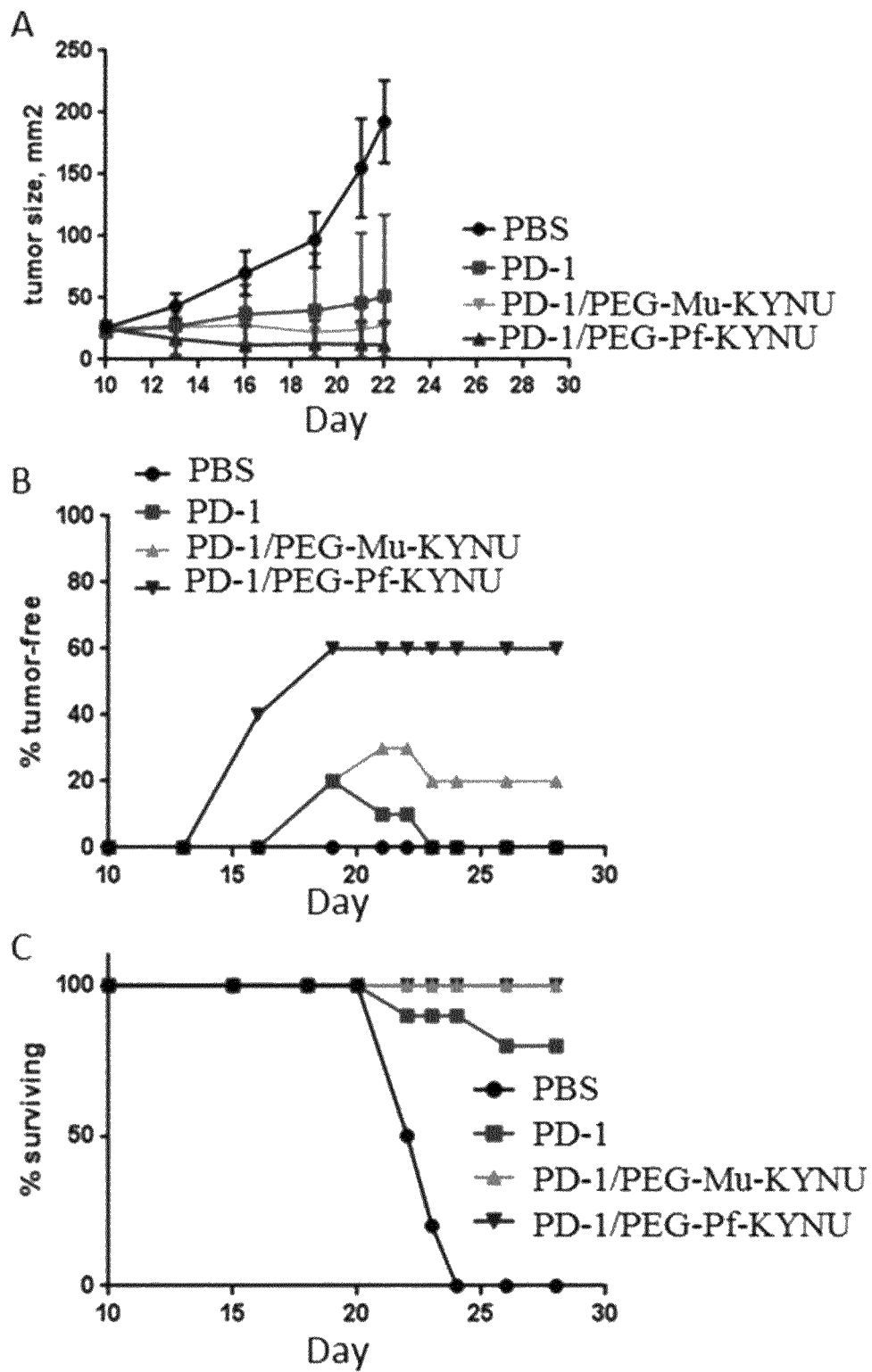
FIGS. 9A-9C—FIG. 9A—C57BL/6J bearing B16 tumor allografts treated with PBS (circle) (control), Programmed Cell Death Protein 1, or PD1 (antibody) alone (square), anti PD1PD1 (antibody)/PEG-Mu-KYNU (upside-down triangle), or anti PD1PD1 (antibody)/PEG-Pf-KYNU (right-side up triangle).

Example 22—Efficacy of Mu-KYNU or Pf-KYNU and Anti-PD1 Combination Therapy in the Autologous B16 Mouse Melanoma Model The PEGylated enzymes (PEG-Pf-KYNU and PEG-Mu-KYNU) were evaluated in B16 melanoma allografts in combination with the anti-PD1 immune checkpoint inhibitor antibody (Curran et al., 2010). Four groups of C57BL/6J mice (10 per group) were implanted with 50,000 B16 cells (Day 0) and tumors were allowed to develop. Once palpable tumors developed (Day 10), the animals were treated with 250 µg anti-PD1 by IP injection (clone RMP1-14, BioXCell # BE0146) on days 10, 13, and 16 either with or without 500 PEG-Pf-KYNU or 500 µg PEG-Mu-KYNU s.c. near the tumor site. Mice received a total of six doses of KYNU between days 10 and 25. One group was given PBS injections i.p. as a control for PD-1. Tumor growth was drastically impaired or even reversed in all treatment arms compared to PBS control (FIG. 9A). Importantly, additive effects were observed with anti-PD1 in combination with KYNU resulting in complete remission of 60% of the tumors with PEG-Pf-KYNU/anti-PD1 treatment and 20% of the tumors with PEG-Mu-KYNU/anti-PD1 treatment (FIG. 9B). Corresponding Kaplan-Meier plots are provided in FIG. 9C.

Figures 10A, 10B:
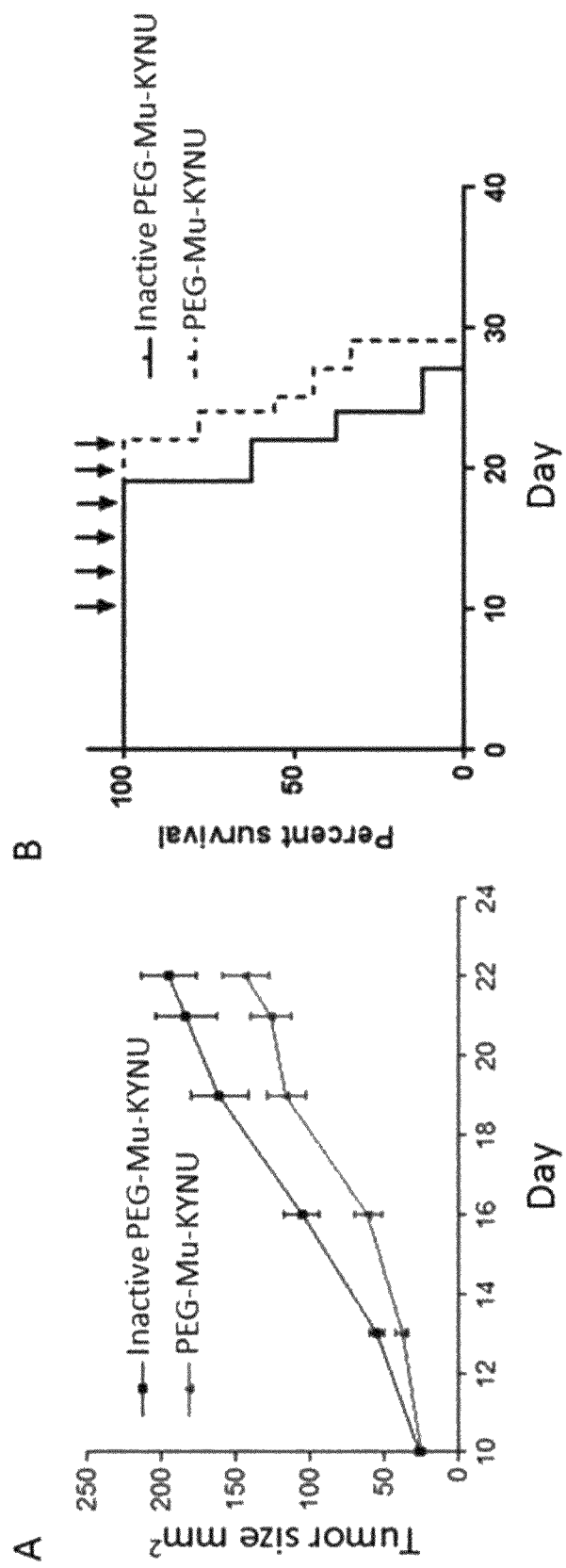
FIGS. 10A-10B—FIG. 10A—C57BL/6J bearing B16 tumor allografts treated with heat-inactivated PEG-Mu-KYNU (■) or active PEG-Mu-KYNU (▲).

Example 23—Efficacy of PEG-Mu-KYNU Therapies in the Autologous B16 Mouse Melanoma Model The PEGylated *Mucilaginibacter paludis* kynureninase (PEG-Mu-KYNU) was evaluated in the B16 melanoma mouse model. Allografts were initiated by implanting 50,000 B16 cells in the flanks of C57BL/6J mice (Day 0, n=9 mice per group). Once palpable tumors developed (Day 10), the animals were treated with 500 µg of PEG-Mu-KYNU by subcutaneous injection near the tumor site every three days for a total of 6 doses. An identical treatment regimen with heat-inactivated PEG-Mu-KYNU was used as a control. Administration of PEG-Mu-KYNU resulted in tumor growth retardation (FIG. 10A) with an extended median survival time of 25 days compared to 22 days for the heat-inactivated PEG-Mu-KYNU control (FIG. 10B).

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,870,287
U.S. Pat. No. 5,739,169
U.S. Pat. No. 5,760,395
U.S. Pat. No. 5,801,005
U.S. Pat. No. 5,824,311
U.S. Pat. No. 5,830,880
U.S. Pat. No. 5,846,945
U.S. Pat. No. 5,889,155
U.S. Pat. No. 7,109,304
U.S. Pat. No. 8,465,743
U.S. Pat. Publn. 2009/0304666
WO 2012/031744
WO 2012/079000
WO 2013/059593

Ahmed et al., HER2-specific T cells target primary glioblastoma stem cells and induce regression of autologous experimental tumors. *Clinical Cancer Research*, 16(2): 474-485, 2010.

Austin-Ward and Villaseca, *Revista Medica de Chile*, 126 (7):838-845, 1998.

Ausubel et al., Current Protocols in Molecular Biology, Greene Publishing Associates and Wiley Interscience, N.Y., 1994.

Bukowski et al., *Clinical Cancer Res.*, 4(10):2337-2347, 1998.

Chen and Guillemin, Kynurenine pathway metabolites in humans: disease and healthy States. *Int J Tryptophan Res*, 2:1-19, 2009.

Christodoulides et al., *Microbiology*, 144(Pt 11):3027-3037, 1998.

Curran et al., PD-1 and CTLA-4 combination blockade expands infiltrating T cells and reduces regulatory T and myeloid cells within B16 melanoma tumors. *Proceedings of the National Academy of Sciences*, 107:4275-4280, 2010.

Davidson et al., *J. Immunother.*, 21(5):389-398, 1998.

de Jong et al., Serum tryptophan and kynurenine concentrations as parameters for indoleamine 2,3-dioxygenase activity in patients with endometrial, ovarian, and vulvar cancer. *Int J Gynecol Cancer*, 21(7):1320-1327, 2011.

Della Chiesa et al., The tryptophan catabolite L-kynurenine inhibits the surface expression of NKp46- and NKG2D-activating receptors and regulates NK-cell function. *Blood*, 108(13):4118-4125, 2006.

Godin-Ethier et al., Indoleamine 2, 3-Dioxygenase Expression in Human Cancers: Clinical and Immunologic Perspectives. *Clinical Cancer Research*, 17(22):6985-6991, 2011.

Hanibuchi et al., *Int. J. Cancer*, 78(4):480-485, 1998.
Harkki et al., *BioTechnology*, 7:596-603, 1989.
Hellstrand et al., *Acta Oncologica*, 37(4):347-353, 1998.
Hollander, *Front. Immun.*, 3:3, 2012.

Holmgaard et al., Indoleamine 2, 3-dioxygenase is a critical resistance mechanism in antitumor T cell immunotherapy targeting CTLA-4. *The Journal of Experimental Medicine*, 210:1389-1402, 2013.

Hoover and Lubkowski, DNAWorks: an automated method for designing oligonucleotides for PCR-based gene synthesis. *Nucleic Acids Research*, 30(10):e43-e43, 2002.

Hopwood et al., In: *Genetic Manipulation of Streptomyces*, A Laboratory Manual, The John Innes Foundation, Norwich, Conn., 1985.

Hui and Hashimoto, *Infection Immun.*, 66(11):5329-5336, 1998.

Ito et al., *J. Biochem.*, 79:1263, 1976.

Kaper et al., Nanosensor detection of an immunoregulatory tryptophan influx/kynurenine efflux cycle. *PLoS Biology*, 5(10):e257, 2007.

Lipowska-Bhalla et al., Targeted immunotherapy of cancer with CAR T cells: achievements and challenges. *Cancer Immunology Immunotherapy*, 61(7):953-962, 2012.

Lob et al., Inhibitors of indoleamine-2,3-dioxygenase for cancer therapy: can we see the wood for the trees? *Nat Rev Cancer*, 9(6):445-452, 2009.

Lordanescu, *J. Bacteriol*, 12:597 601, 1975.

Mandi and Vecsei, The kynurenine system and immuno-regulation. *J Neural Transm*, 119(2):197-209, 2012.

Maniatis, et al., Molecular Cloning, A Laboratory Manual, Cold Spring Harbor Press, Cold Spring Harbor, N.Y., 1988.

Mellor et al., *Gene*, 24:1-14, 1983.

Mezrich et al., An interaction between kynurenine and the aryl hydrocarbon receptor can generate regulatory T cells. *The Journal of Immunology*, 185(6):3190-3198, 2010.

Opitz et al., The Indoleamine-2, 3-Dioxygenase (IDO) Inhibitor 1-Methyl-D-tryptophan Upregulates IDO1 in Human Cancer Cells. *PLoS One*, 6(5):e19823, 2011.

Opitz et al., An endogenous tumour-promoting ligand of the human aryl hydrocarbon receptor. *Nature*, 478(7368):197-203, 2011.

Penttila et al., *Gene*, 61:155-164, 1987.

Pilotte et al., Reversal of tumoral immune resistance by inhibition of tryptophan 2,3-dioxygenase. *Proc Natl Acad Sci USA*, 109(7):2497-2502, 2012.

Prendergast, Cancer: Why tumours eat tryptophan. *Nature*, 478(7368):192-194, 2011.

Qin et al., *Proc. Natl. Acad. Sci. USA*, 95(24):14411-14416, 1998.

Remington's Pharmaceutical Sciences, 18th Ed. Mack Printing Company, 1289-1329, 1990.

Rutella et al., Targeting indoleamine 2,3-dioxygenase (IDO) to counteract tumour-induced immune dysfunction: from biochemistry to clinical development. *Endocr Metab Immune Disord Drug Targets*, 9(2):151-177, 2009.

Schellenberger et al., *Nature Biotech.*, 27:1186-1190, 2009.

Shin et al., Modulation of natural killer cell antitumor activity by the aryl hydrocarbon receptor. *Proc Natl Acad Sci USA*, 110(30):12391-12396, 2013.

Sibakov et al., *Eur. J. Biochem.*, 145:567 572, 1984.

Song et al., L-Kynurenine-induced apoptosis in human NK cells is mediated by reactive oxygen species. *International Immunopharmacology*, 11(8):932-938, 2011.

Stone et al., Replacing $Mn^{2+}$ with $Co^{2+}$ in human arginase I enhances cytotoxicity toward L-arginine auxotrophic cancer cell lines. *ACS Chemical Biology*, 5:333-342, 2010.

Ward, Proc, Embo-Alko Workshop on Molecular Biology of Filamentous Fungi, Helsinki, 119-128, 1989.

Wawrzynczak and Thorpe, In: *Immunoconjugates, Antibody Conuugates In Radioimaging And Therapy Of Cancer*, Vogel (Ed.), NY, Oxford University Press, 28, 1987.

Yao et al., Serum metabolic profiling and features of papillary thyroid carcinoma and nodular goiter. *Mol Biosyst*, 7(9):2608-2614, 2011.

Yoshikawa et al., Serum concentration of L-kynurenine predicts the clinical outcome of patients with diffuse large B-cell lymphoma treated with R-CHOP. *Eur J Haematol*, 84(4):304-309, 2010.

What is claimed is:

1. An isolated polypeptide comprising a kynureninase enzyme having an amino acid sequence that is at least 90% identical to SEQ ID NO: 8, and having one or more substitutions relative to SEQ ID NO: 8, wherein the one or more substitutions comprise a substitution of the Phe found at position 306 of SEQ ID NO: 8, wherein the enzyme is formulated in a pharmaceutically acceptable carrier.

2. The enzyme of claim 1, wherein the enzyme has an amino acid sequence that is at least 95% identical to SEQ ID NO: 8.

3. The enzyme of claim 1, wherein the at least one substitution comprises Phe306Met.

4. The enzyme of claim 1, wherein the at least one substitution comprises Phe306Leu.

5. The enzyme of claim 1, further comprising a heterologous peptide segment.

6. The enzyme of claim 5, wherein the heterologous peptide segment is an XTEN peptide, an IgG Fc, an albumin, or an albumin binding peptide.

7. The enzyme of claim 1, wherein the enzyme is coupled to polyethylene glycol (PEG).

8. The enzyme of claim 7, wherein the enzyme is coupled to PEG by way of one or more Lys or Cys residues.

9. The enzyme of claim 1, wherein the kynureninase has greater catalytic activity towards kynurenine than 3'-OH kynurenine.

10. The enzyme of claim 1, wherein the kynureninase has a $k_{cat}/K_M$ for kynurenine of at least 0.5 $M^{-1}/s^{-1}$.

11. A nucleic acid encoding the enzyme of claim 1.

12. The nucleic acid of claim 11, wherein the nucleic acid is codon optimized for expression in bacteria, fungus, insects, or mammals.

13. An expression vector comprising the nucleic acid of claim 11.

14. A host cell comprising the nucleic acid of claim 11.

15. The host cell of claim 14, wherein the host cell is a bacterial cell, a fungal cell, an insect cell, or a mammalian cell.

16. A pharmaceutical composition comprising the expression vector of claim 13.

17. The pharmaceutical composition of claim 16, wherein the enzyme has an amino acid sequence that is at least 95% identical to SEQ ID NO: 8.

18. The pharmaceutical composition of claim 16, wherein the kynureninase has greater catalytic activity towards kynurenine than 3'-OH kynurenine.

19. The pharmaceutical composition of claim 16, wherein the kynureninase has a $k_{cat}/K_M$ for kynurenine of at least 0.5 $M^{-1}/s^{-1}$.

* * * * *

UNITED STATES PATENT AND TRADEMARK OFFICE
CERTIFICATE OF CORRECTION

PATENT NO. : 10,772,913 B2
APPLICATION NO. : 16/373588
DATED : September 15, 2020
INVENTOR(S) : George Georgiou and Everett Stone It is certified that error appears in the above-identified patent and that said Letters Patent is hereby corrected as shown below:

On the Title Page

Item (56) References Cited - Other Publications, insert --Office Communication issued in U.S. Appl. No. 14/839,293, dated Oct. 19, 2017.--.

Signed and Sealed this
Twenty-seventh Day of July, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 57

<210> SEQ ID NO 1
<211> LENGTH: 1347
<212> TYPE: DNA
<213> ORGANISM: Artificial Sequence
<220> FEATURE:
<223> OTHER INFORMATION: Synthetic polynucleotide

<400> SEQUENCE: 1
tctagaaata attttgttta actttaagga aaacattaaa ataaggaggt agcaaatggg      60
cggtcatcat caccaccatc atgggagcgg caccaccgc aacgattgcc tggcgctgga     120
tgcgcaggat agcctggcac cgctgcgtca gcagtttgcg ctgccggaag gtgttattta     180
tctggatggc aacagcctgg gtgcgcgtcc ggttgcggcg ctggcgcgtg cgcaggcggt     240
gattgcggaa gaatggggca acggcctgat tcgcagctgg aacagcgcgg gctggcgcga     300
tctgagcgaa cgcctgggca accgcctggc gaccctgatt ggcgcgcgcg atggcgaagt     360
ggtggtgacc gataccacca gcattaacct gtttaaagtg ctgagcgcgg cgctgcgcgt     420
gcaggcgacc cgcagcccgg aacgccgcgt gattgtgacc gaaaccagca actttccgac     480
cgatctgtat attgcggaag gcctggcgga tatgctgcag cagggctata ccctgcgcct     540
ggtggatagc ccggaagaac tgccgcaggc gattgatcag gataccgcgg tggtgatgct     600
gacccatgtg aactataaaa ccggctatat gcatgatatg caggcgctga ccgcgctgag     660
ccatgaatgc ggcgcgctgg cgatttggga tctggcgcat agcgcgggcg cggtgccggt     720
ggatctgcat caggcgggcg cggattatgc gattggctgc acctataaat atctgaacgg     780
cggcccgggc agccaggcgt ttgtgtgggt gagcccgcag ctgtgcgatc tggtgccgca     840
gccgctgtct ggttggtttg gccatagccg ccagtttgcg atggaaccgc gctatgaacc     900
```

```
gagcaacggc attgcgcgct atctgtgcgg cacccagccg attaccagcc tggcgatggt        960
ggaatgcggc ctggatgtgt tgcgcagac cgatatggcg agcctgcgcc gcaaaagcct       1020
ggcgctgacc gatctgttta ttgaactggt ggaacagcgc tgcgcggcgc atgaactgac       1080
cctggtgacc ccgcgcgaac atgcgaaacg cggcagccat gtgagctttg aacatccgga       1140
aggctatgcg gtgattcagg cgctgattga tcgcggcgtg attggcgatt atcgcgaacc       1200
gcgcattatg cgctttggct ttaccccgct gtataccacc tttaccgaag tgtgggatgc       1260
ggtgcagatt ctgggcgaaa ttctggatcg caaaacctgg gcgcaggcgc agtttcaggt       1320
gcgccatagc gtgacctagt aggatcc                                          1347

<210> SEQ ID NO 2
<211> LENGTH: 1497
<212> TYPE: DNA
<213> ORGANISM: Artificial Sequence
<220> FEATURE:
<223> OTHER INFORMATION: Synthetic polynucleotide

<400> SEQUENCE: 2
tctagaaata attttgttta actttaagga caaatcagga cacagttaag gaggtaaaat         60
atgggcggtc atcatcacca ccatcatggg agcggcgaac cgagctccct tgaacttccg        120
gccgataccg tgcaacggat agcggcggaa ttgaaatgtc acccgaccga cgaacgcgtc        180
gcgttacatc tggatgagga agacaagctg cgtcacttcc gcgagtgctt ttacattccg        240
aaaattcagg atctgccgcc agtggacttg agcctggtca acaaagacga gaacgccatc        300
tacttcctgg gcaatagcct gggcctgcaa ccaaagatgg tgaaaaccta tcttgaggag        360
gagcttgaca atgggcgaa gatcgcggcc tacggccatg aagtcggcaa cgtccctgg         420 attaccggcg atgagtcaat cgttggcttg atgaaggata tcgtcggcgc gaacgagaaa        480
gaaattgcgc tgatgaacgc gctgaccgtg aatctgcatc tgctgatgct gtcattcttt        540
aagcccaccc cgaagcgcta caaaatcctg ctggaagcga aagcgtttcc cagcgatcat        600
tatgcgatag aaagccagct gcaactgcac ggcctgaata tcgaggagag catgcgtatg        660
ataaaaccgc gcgaaggtga ggagaccctg cggattgagg catcctggaa ggtgatcgag        720
aaggagggcg acagtatcgc ggtgatactt ttcagcggcg tgcatttcta cacgggccaa        780
cacttcaata tcccggccat taccaaagcc ggccaggcga aagggtgcta tgtaggcttt        840
gatctggcgc atgcagtggg caacgtcgaa ctgtatcttc atgattgggg cgttgatttt        900
gcgtgctggt gcagctataa gtatctgaat gccggggccg gtgggattgc gggagccttt        960
attcatgaga acacgcgca taccattaaa ccggcgctgg ttggctggtt tgggcacgaa       1020
ctgagcaccc gcttcaagat ggataacaaa ctgcaattga ttccgggcgt gtgcggcttt       1080
cgtattagca accccccgat tctgctggtc tgcagcctgc acgcgtctct ggagattttc       1140
aagcaggcga ccatgaaagc gctgcgtaag aaaagtgtgc ttctgacggg ctacctggag       1200
tacctgataa agcacaacta cggcaaggat aaggcggcca cgaagaagcc ggttgtgaac       1260
attatcaccc cgtctcatgt ggaagaacgt ggctgccaac tgacgataac gttcagcgtg       1320
ccaaacaagg acgtgttcca agagctggag aagcgtggcg tggtgtgtga taacgtaat        1380 ccgaatggca ttcgtgtggc gcctgtgccg ctgtacaaca gcttccacga cgtgtataag       1440
ttcaccaacc tgctgacgag cattctggac agtgcggaaa ccaaaaacta gggatcc          1497

<210> SEQ ID NO 3
```

<211> LENGTH: 1492
<212> TYPE: DNA
<213> ORGANISM: Artificial Sequence
<220> FEATURE:
<223> OTHER INFORMATION: Synthetic polynucleotide

<400> SEQUENCE: 3

```
tctagaaata attttgttta actttaagaa cacggtcggg aatataagga ggtaaaatat      60
gggcggtcat catcaccacc atcatgggag cggcgagccg agcccgctgg aactgccggt     120
tgacgcggta cgtcgtattg cggcagaact gaactgtgac ccgaccgatg aacgtgtggc     180
gctgcgtctc gacgaagagg acaagctctc tcacttccgt aactgcttct atatccctaa     240
aatgcgtgac ctgccgagca tcgatctgtc tctggtttct gaagacgacg acgcgattta     300
cttcctgggt aactctctgg gtctgcagcc aaaaatggtt cgtacctacc tggaggaaga     360
gctggacaaa tgggcgaaaa tgggtgccta cggccatgat gtgggcaaac gcccgtggat     420
cgtcggcgac gaaagcattg tgtctctcat aaggacattg ttggtgcac acgagaaaga      480
aattgcgctg atgaatgctc tgaccatcaa cctgcacctg ctgctcctgt ctttcttcaa     540
gccgaccccg aagcgtcata aaatcctgct cgaggctaaa gcgttcccgt ctgatcacta     600
cgcgatcgaa tctcaaatcc aactgcacgg tctggacgtt gagaagtcta tgcgtatggt     660
taagccgcgt gaaggcgagg agaccctccg tatggaagac atcctcgaag ttatcgaaga     720
agaaggtgac tctatcgcag ttattctgtt ctctggcctg cacttttaca ccggtcaact     780
gttcaatatc ccggcaatca ccaaagcggg ccacgcgaaa ggttgcttcg ttggtttcga     840
cctgcccat gcgttggta acgtggagct gcgcctccac gactgggtg ttgactttgc        900
gtgctggtgc tcttacaaat acctgaactc tggtgcgggt ggtctcgcgg gtgcgttcgt     960
ccacgaaaaa cacgcgcaca ccgttaaacc ggcgctggtt ggctggttcg gccacgacct    1020
ctctacgcgt ttcaacatgg acaacaaact ccagctgatc ccaggcgcca acggtttccg    1080
tatctctaac ccgccgatcc tcctggtttg ctctctgcac gcgtctctcg aggttttcca    1140
gcaggcgacc atgaccgccc tgcgccgtaa atctattctc ctgacgggtt atctggaata    1200
catgctgaag cactaccact ctaaagacaa cacggaaaac aaaggtccga tcgttaacat    1260
catcaccccg tctcgtgcgg aagaacgtgg ctgccaactg accctgacct tctctattcc    1320
gaaaaaatct gttttcaaag aactggagaa acgtggtgtt gtttgcgaca aacgtgaacc    1380
ggacggtatc cgcgttgctc cggtcccgct gtacaactct ttccatgacg tttataagtt    1440
cattcgtctg ctcacctcca tcctggactc tagcgaacgc tcctaaggat cc            1492
```

<210> SEQ ID NO 4
<211> LENGTH: 1251
<212> TYPE: DNA
<213> ORGANISM: Pseudomonas fluorescens

<400> SEQUENCE: 4

```
atgaccaccc gcaacgattg cctggcgctg gatgcgcagg atagcctggc accgctgcgt      60
cagcagtttg cgctgccgga aggtgttatt tatctggatg gcaacagcct gggtgcgcgt     120
ccggttgcgg cgctggcgcg tgcgcaggcg gtgattgcgg aagaatgggg caacggcctg     180
attcgcagct ggaacagcgc gggctggcgc gatctgagcg aacgcctggg caaccgcctg     240
gcgaccctga ttggcgcgcg cgatggcgaa tggtggtga ccgataccac cagcattaac       300
ctgtttaaag tgctgagcgc ggcgctgcgc gtgcaggcga cccgcagccc ggaacgccgc     360
gtgattgtga ccgaaaccag caactttccg accgatctgt atattgcgga aggcctggcg     420
```

| | |
|---|---|
| gatatgctgc agcagggcta taccctgcgc ctggtggata gcccggaaga actgccgcag | 480 |
| gcgattgatc aggataccgc ggtggtgatg ctgacccatg tgaactataa aaccggctat | 540 |
| atgcatgata tgcaggcgct gaccgcgctg agccatgaat gcggcgcgct ggcgatttgg | 600 |
| gatctggcgc atagcgcggg cgcggtgccg gtggatctgc atcaggcggg cgcggattat | 660 |
| gcgattggct gcacctataa atatctgaac ggcggcccgg gcagccaggc gtttgtgtgg | 720 |
| gtgagcccgc agctgtgcga tctggtgccg cagccgctgt ctggttggtt tggccatagc | 780 |
| cgccagtttg cgatggaacc gcgctatgaa ccgagcaacg gcattgcgcg ctatctgtgc | 840 |
| ggcacccagc cgattaccag cctggcgatg gtggaatgcg gcctggatgt gtttgcgcag | 900 |
| accgatatgg cgagcctgcg ccgcaaaagc ctggcgctga ccgatctgtt tattgaactg | 960 |
| gtggaacagc gctgcgcggc gcatgaactg accctggtga ccccgcgcga acatgcgaaa | 1020 |
| cgcggcagcc atgtgagctt tgaacatccg gaaggctatg cggtgattca ggcgctgatt | 1080 |
| gatcgcggcg tgattggcga ttatcgcgaa ccgcgcatta tgcgctttgg ctttaccccg | 1140 |
| ctgtatacca ccttttaccga agtgtgggat gcggtgcaga ttctgggcga aattctggat | 1200 |
| cgcaaaacct gggcgcaggc gcagtttcag gtgcgccata gcgtgaccta g | 1251 |

<210> SEQ ID NO 5
<211> LENGTH: 1398
<212> TYPE: DNA
<213> ORGANISM: Homo sapiens

<400> SEQUENCE: 5

| | |
|---|---|
| atggaaccga gctcccttga acttccggcc gataccgtgc aacggatagc ggcggaattg | 60 |
| aaatgtcacc cgaccgacga acgcgtcgcg ttacatctgg atgaggaaga caagctgcgt | 120 |
| cacttccgcg agtgctttta cattccgaaa attcaggatc tgccgccagt ggacttgagc | 180 |
| ctggtcaaca aagacgagaa cgccatctac ttcctgggca atagcctggg cctgcaacca | 240 |
| aagatggtga aaacctatct tgaggaggag cttgacaaat gggcgaagat cgcggcctac | 300 |
| ggccatgaag tcggcaagcg tccctggatt accggcgatg agtcaatcgt tggcttgatg | 360 |
| aaggatatcg tcggcgcgaa cgagaaagaa attgcgctga tgaacgcgct gaccgtgaat | 420 |
| ctgcatctgc tgatgctgtc attctttaag cccaccccga gcgctacaa aatcctgctg | 480 |
| gaagcgaaag cgtttcccag cgatcattat gcgatagaaa gccagctgca actgcacggc | 540 |
| ctgaatatcg aggagagcat gcgtatgata aaaccgcgcg aaggtgagga cccctgcgg | 600 |
| attgaggaca tcctggaggt gatcgagaag gagggcgaca gtatcgcggt gatactttc | 660 |
| agcggcgtgc atttctacac gggccaacac ttcaatatcc cggccattac caaagccggc | 720 |
| caggcgaaag ggtgctatgt aggctttgat ctggcgcatg cagtgggcaa cgtcgaactg | 780 |
| tatcttcatg attgggggcgt tgattttgcg tgctggtgca gctataagta tctgaatgcc | 840 |
| ggggccggtg ggattgcggg agcctttatt catgagaaac acgcgcatac cattaaaccg | 900 |
| gcgctggttg gctggtttgg cacgaactg agcacccgct tcaagatgga taacaaactg | 960 |
| caattgattc cggcgtgtg cggctttcgt attagcaacc ccccgattct gctggtctgc | 1020 |
| agcctgcacg cgtctctgga gattttcaag caggcgacca tgaaagcgct gcgtaagaaa | 1080 |
| agtgtgcttc tgacgggcta cctggagtac ctgataaagc acaactacgg caaggataag | 1140 |
| gcggccacga agaagccggt tgtgaacatt atcaccccgt ctcatgtgga gaacgtggc | 1200 |
| tgccaactga cgataacgtt cagcgtgcca aacaaggacg tgttccaaga gctggagaag | 1260 |

-continued

```
cgtggcgtgg tgtgtgataa acgtaatccg aatggcattc gtgtggcgcc tgtgccgctg    1320
tacaacagct tccacgacgt gtataagttc accaacctgc tgacgagcat tctggacagt    1380
gcggaaacca aaaactag                                                   1398
```

<210> SEQ ID NO 6
<211> LENGTH: 1395
<212> TYPE: DNA
<213> ORGANISM: Mus musculus

<400> SEQUENCE: 6

```
atggagccga cccgctggaa actgccggtt gacgcggtac gtcgtattgc ggcagaactg      60
aactgtgacc cgaccgatga acgtgtggcg ctgcgtctcg acgaagagga caagctctct    120
cacttccgta actgcttcta tatccctaaa atgcgtgacc tgccgagcat cgatctgtct    180
ctggtttctg aagacgacga cgcgatttac ttcctgggta actctctggg tctgcagcca    240
aaaatggttc gtacctacct ggaggaagag ctggacaaat gggcgaaaat gggtgcctac    300
ggccatgatg tgggcaaacg cccgtggatc gtcggcgacg aaagcattgt gtctctcatg    360
aaggacattg ttggtgcaca cgagaaagaa attgcgctga tgaatgctct gaccatcaac    420
ctgcacctgc tgctcctgtc tttcttcaag ccgaccccga agcgtcataa aatcctgctc    480
gaggctaaag cgttcccgtc tgatcactac gcgatcgaat ctcaaatcca actgcacggt    540
ctggacgttg agaagtctat gcgtatggtt aagccgcgtg aaggcgagga ccctccgt      600 atggaagaca tcctcgaagt tatcgaagaa gaaggtgact ctatcgcagt tattctgttc    660
tctggcctgc acttttacac cggtcaactg ttcaatatcc cggcaatcac caaagcgggc    720
cacgcgaaag gttgcttcgt tggtttcgac ctggcccatg cggttggtaa cgtggagctg    780
cgcctccacg actggggtgt tgactttgcg tgctggtgct cttacaaata cctgaactct    840
ggtgcgggtg gtctcgcggg tgcgttcgtc cacgaaaaac acgcgcacac cgttaaaccg    900
gcgctggttg gctggttcgg ccacgacctc tctacgcgtt tcaacatgga caacaaactc    960
cagctgatcc caggcgccaa cggtttccgt atctctaacc cgccgatcct cctggtttgc   1020
tctctgcacg cgtctctcga ggttttccag caggcgacca tgaccgccct cgccgtaaa    1080 tctattctcc tgacgggtta tctggaatac atgctgaagc actaccactc taaagacaac   1140
acggaaaaca aggtccgat cgttaacatc atcaccccgt ctcgtgcgga gaacgtggc    1200 tgccaactga ccctgacctt ctctattccg aaaaaatctg tttttcaaga actggagaaa    1260
cgtggtgttg tttgcgacaa acgtgaaccg gacggtatcc gcgttgctcc ggtcccgctg    1320
tacaactctt tccatgacgt ttataagttc attcgtctgc tcacctccat cctggactct    1380
agcgaacgct cctaa                                                      1395
```

<210> SEQ ID NO 7
<211> LENGTH: 416
<212> TYPE: PRT
<213> ORGANISM: Pseudomonas fluorescens

<400> SEQUENCE: 7

Met Thr Thr Arg Asn Asp Cys Leu Ala Leu Asp Ala Gln Asp Ser Leu
1               5                   10                  15

Ala Pro Leu Arg Gln Gln Phe Ala Leu Pro Glu Gly Val Ile Tyr Leu
            20                  25                  30

Asp Gly Asn Ser Leu Gly Ala Arg Pro Val Ala Ala Leu Ala Arg Ala
        35                  40                  45

```
Gln Ala Val Ile Ala Glu Glu Trp Gly Asn Gly Leu Ile Arg Ser Trp
 50                  55                  60
Asn Ser Ala Gly Trp Arg Asp Leu Ser Glu Arg Leu Gly Asn Arg Leu
 65                  70                  75                  80
Ala Thr Leu Ile Gly Ala Arg Asp Gly Glu Val Val Thr Asp Thr
                 85                  90                  95
Thr Ser Ile Asn Leu Phe Lys Val Leu Ser Ala Ala Leu Arg Val Gln
                100                 105                 110
Ala Thr Arg Ser Pro Glu Arg Arg Val Ile Val Thr Glu Thr Ser Asn
                115                 120                 125
Phe Pro Thr Asp Leu Tyr Ile Ala Glu Gly Leu Ala Asp Met Leu Gln
130                 135                 140
Gln Gly Tyr Thr Leu Arg Leu Val Asp Ser Pro Glu Glu Leu Pro Gln
145                 150                 155                 160
Ala Ile Asp Gln Asp Thr Ala Val Val Met Leu Thr His Val Asn Tyr
                165                 170                 175
Lys Thr Gly Tyr Met His Asp Met Gln Ala Leu Thr Ala Leu Ser His
                180                 185                 190
Glu Cys Gly Ala Leu Ala Ile Trp Asp Leu Ala His Ser Ala Gly Ala
                195                 200                 205
Val Pro Val Asp Leu His Gln Ala Gly Ala Asp Tyr Ala Ile Gly Cys
210                 215                 220
Thr Tyr Lys Tyr Leu Asn Gly Gly Pro Gly Ser Gln Ala Phe Val Trp
225                 230                 235                 240
Val Ser Pro Gln Leu Cys Asp Leu Val Pro Gln Pro Leu Ser Gly Trp
                245                 250                 255
Phe Gly His Ser Arg Gln Phe Ala Met Glu Pro Arg Tyr Glu Pro Ser
                260                 265                 270
Asn Gly Ile Ala Arg Tyr Leu Cys Gly Thr Gln Pro Ile Thr Ser Leu
                275                 280                 285
Ala Met Val Glu Cys Gly Leu Asp Val Phe Ala Gln Thr Asp Met Ala
                290                 295                 300
Ser Leu Arg Arg Lys Ser Leu Ala Leu Thr Asp Leu Phe Ile Glu Leu
305                 310                 315                 320
Val Glu Gln Arg Cys Ala Ala His Glu Leu Thr Leu Val Thr Pro Arg
                325                 330                 335
Glu His Ala Lys Arg Gly Ser His Val Ser Phe Glu His Pro Glu Gly
                340                 345                 350
Tyr Ala Val Ile Gln Ala Leu Ile Asp Arg Gly Val Ile Gly Asp Tyr
                355                 360                 365
Arg Glu Pro Arg Ile Met Arg Phe Gly Phe Thr Pro Leu Tyr Thr Thr
370                 375                 380
Phe Thr Glu Val Trp Asp Ala Val Gln Ile Leu Gly Glu Ile Leu Asp
385                 390                 395                 400
Arg Lys Thr Trp Ala Gln Ala Gln Phe Gln Val Arg His Ser Val Thr
                405                 410                 415

<210> SEQ ID NO 8
<211> LENGTH: 465
<212> TYPE: PRT
<213> ORGANISM: Homo sapiens

<400> SEQUENCE: 8

Met Glu Pro Ser Ser Leu Glu Leu Pro Ala Asp Thr Val Gln Arg Ile
1               5                   10                  15
```

Ala Ala Glu Leu Lys Cys His Pro Thr Asp Glu Arg Val Ala Leu His
            20                  25                  30

Leu Asp Glu Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
 50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
                180                 185                 190

Arg Glu Gly Glu Glu Thr Leu Arg Ile Glu Asp Ile Leu Glu Val Ile
                195                 200                 205

Glu Lys Glu Gly Asp Ser Ile Ala Val Ile Leu Phe Ser Gly Val His
210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
            275                 280                 285

Phe Ile His Glu Lys His Ala His Thr Ile Lys Pro Ala Leu Val Gly
290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
            340                 345                 350

Thr Met Lys Ala Leu Arg Lys Lys Ser Val Leu Leu Thr Gly Tyr Leu
            355                 360                 365

Glu Tyr Leu Ile Lys His Asn Tyr Gly Lys Asp Lys Ala Ala Thr Lys
            370                 375                 380

Lys Pro Val Val Asn Ile Ile Thr Pro Ser His Val Glu Glu Arg Gly
385                 390                 395                 400

Cys Gln Leu Thr Ile Thr Phe Ser Val Pro Asn Lys Asp Val Phe Gln
                405                 410                 415

Glu Leu Glu Lys Arg Gly Val Val Cys Asp Lys Arg Asn Pro Asn Gly
                420                 425                 430

```
Ile Arg Val Ala Pro Val Pro Leu Tyr Asn Ser Phe His Asp Val Tyr
            435                 440                 445

Lys Phe Thr Asn Leu Leu Thr Ser Ile Leu Asp Ser Ala Glu Thr Lys
450                 455                 460

Asn
465

<210> SEQ ID NO 9
<211> LENGTH: 464
<212> TYPE: PRT
<213> ORGANISM: Mus musculus

<400> SEQUENCE: 9

Met Glu Pro Ser Pro Leu Glu Leu Pro Val Asp Ala Val Arg Arg Ile
1               5                   10                  15

Ala Ala Glu Leu Asn Cys Asp Pro Thr Asp Glu Arg Val Ala Leu Arg
            20                  25                  30

Leu Asp Glu Glu Asp Lys Leu Ser His Phe Arg Asn Cys Phe Tyr Ile
        35                  40                  45

Pro Lys Met Arg Asp Leu Pro Ser Ile Asp Leu Ser Leu Val Ser Glu
    50                  55                  60

Asp Asp Ala Ile Tyr Phe Leu Gly Asn Ser Leu Gly Leu Gln Pro
65                  70                  75                  80

Lys Met Val Arg Thr Tyr Leu Glu Glu Leu Asp Lys Trp Ala Lys
                85                  90                  95

Met Gly Ala Tyr Gly His Asp Val Gly Lys Arg Pro Trp Ile Val Gly
            100                 105                 110

Asp Glu Ser Ile Val Ser Leu Met Lys Asp Ile Val Gly Ala His Glu
        115                 120                 125

Lys Glu Ile Ala Leu Met Asn Ala Leu Thr Ile Asn Leu His Leu Leu
    130                 135                 140

Leu Leu Ser Phe Phe Lys Pro Thr Pro Lys Arg His Lys Ile Leu Leu
145                 150                 155                 160

Glu Ala Lys Ala Phe Pro Ser Asp His Tyr Ala Ile Glu Ser Gln Ile
                165                 170                 175

Gln Leu His Gly Leu Asp Val Glu Lys Ser Met Arg Met Val Lys Pro
            180                 185                 190

Arg Glu Gly Glu Glu Thr Leu Arg Met Glu Asp Ile Leu Glu Val Ile
        195                 200                 205

Glu Glu Glu Gly Asp Ser Ile Ala Val Ile Leu Phe Ser Gly Leu His
    210                 215                 220

Phe Tyr Thr Gly Gln Leu Phe Asn Ile Pro Ala Ile Thr Lys Ala Gly
225                 230                 235                 240

His Ala Lys Gly Cys Phe Val Gly Phe Asp Leu Ala His Ala Val Gly
                245                 250                 255

Asn Val Glu Leu Arg Leu His Asp Trp Gly Val Asp Phe Ala Cys Trp
            260                 265                 270

Cys Ser Tyr Lys Tyr Leu Asn Ser Gly Ala Gly Gly Leu Ala Gly Ala
        275                 280                 285

Phe Val His Glu Lys His Ala His Thr Val Lys Pro Ala Leu Val Gly
    290                 295                 300

Trp Phe Gly His Asp Leu Ser Thr Arg Phe Asn Met Asp Asn Lys Leu
305                 310                 315                 320

Gln Leu Ile Pro Gly Ala Asn Gly Phe Arg Ile Ser Asn Pro Pro Ile
                325                 330                 335
```

```
Leu Leu Val Cys Ser Leu His Ala Ser Leu Glu Val Phe Gln Gln Ala
            340                 345                 350

Thr Met Thr Ala Leu Arg Arg Lys Ser Ile Leu Leu Thr Gly Tyr Leu
        355                 360                 365

Glu Tyr Met Leu Lys His Tyr His Ser Lys Asp Asn Thr Glu Asn Lys
    370                 375                 380

Gly Pro Ile Val Asn Ile Ile Thr Pro Ser Arg Ala Glu Glu Arg Gly
385                 390                 395                 400

Cys Gln Leu Thr Leu Thr Phe Ser Ile Pro Lys Lys Ser Val Phe Lys
                405                 410                 415

Glu Leu Glu Lys Arg Gly Val Val Cys Asp Lys Arg Glu Pro Asp Gly
                420                 425                 430

Ile Arg Val Ala Pro Val Pro Leu Tyr Asn Ser Phe His Asp Val Tyr
                435                 440                 445

Lys Phe Ile Arg Leu Leu Thr Ser Ile Leu Asp Ser Ser Glu Arg Ser
450                 455                 460
```

<210> SEQ ID NO 10
<211> LENGTH: 466
<212> TYPE: PRT
<213> ORGANISM: Pongo abelii

<400> SEQUENCE: 10

```
Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Glu Asp Lys Leu Arg His Phe Arg Glu Tyr Phe Tyr Ile
        35                  40                  45

Pro Lys Ile Arg Asp Leu Pro Pro Val Asp Phe Ile Ile Ser Glu Ser
    50                  55                  60

Lys Asp Glu Asn Ala Ile Tyr Phe Leu Gly Asn Ser Leu Gly Leu Gln
65                  70                  75                  80

Pro Lys Met Val Lys Thr Tyr Leu Glu Glu Glu Leu Asp Lys Trp Ala
                85                  90                  95

Lys Ile Ala Ala Tyr Gly His Glu Val Gly Lys Arg Pro Trp Ile Thr
            100                 105                 110

Gly Asp Glu Ser Ile Val Gly Leu Met Lys Asp Ile Val Gly Ala Asn
        115                 120                 125

Glu Lys Glu Ile Ala Leu Met Asn Ala Leu Thr Val Asn Leu His Leu
    130                 135                 140

Leu Met Leu Ser Phe Phe Lys Pro Thr Pro Lys Arg Tyr Lys Ile Leu
145                 150                 155                 160

Leu Glu Ala Lys Ala Phe Pro Ser Asp His Tyr Ala Ile Glu Ser Gln
                165                 170                 175

Leu Gln Leu His Gly Leu Asn Ile Glu Glu Ser Met Arg Met Val Lys
            180                 185                 190

Pro Arg Glu Gly Glu Glu Thr Leu Arg Thr Glu Asp Ile Leu Glu Val
        195                 200                 205

Ile Glu Lys Glu Gly Asp Ser Ile Ala Val Ile Leu Phe Ser Gly Val
    210                 215                 220

His Phe Tyr Thr Gly Gln His Phe Asn Ile Pro Ala Ile Thr Lys Ala
225                 230                 235                 240

Gly Gln Ala Lys Gly Cys Tyr Val Gly Phe Asp Leu Ala His Ala Val
```

```
                    245                 250                 255
Gly Asn Val Glu Leu Tyr Leu His Asp Trp Gly Val Asp Phe Ala Cys
            260                 265                 270

Trp Cys Ser Tyr Lys Tyr Leu Asn Ala Gly Ala Gly Gly Ile Ala Gly
            275                 280                 285

Ala Phe Val His Glu Lys His Ala His Thr Ile Lys Pro Ala Leu Val
            290                 295                 300

Gly Trp Phe Gly His Glu Leu Ser Thr Arg Phe Lys Met Asp Asn Lys
305                 310                 315                 320

Leu Gln Leu Ile Pro Gly Val Cys Gly Phe Arg Ile Ser Asn Pro Pro
                325                 330                 335

Ile Leu Leu Val Cys Ser Leu His Ala Ser Leu Glu Ile Phe Lys Gln
                340                 345                 350

Ala Thr Met Lys Ala Leu Arg Lys Lys Ser Ile Leu Leu Thr Gly Tyr
                355                 360                 365

Leu Glu Tyr Leu Ile Lys His Ser Tyr Gly Lys Asp Lys Ala Ala Thr
370                 375                 380

Lys Lys Pro Val Val Asn Ile Ile Thr Pro Ser His Ile Glu Glu Arg
385                 390                 395                 400

Gly Cys Gln Leu Thr Ile Thr Phe Ser Val Pro Asn Lys Asp Val Phe
                405                 410                 415

Gln Glu Leu Glu Lys Arg Gly Val Val Cys Asp Lys Arg Asn Pro Asn
                420                 425                 430

Gly Ile Arg Val Ala Pro Val Pro Leu Tyr Asn Ser Phe His Asp Val
                435                 440                 445

Tyr Lys Phe Thr Asn Leu Leu Thr Ser Ile Leu Asp Ser Ala Glu Thr
            450                 455                 460

Thr Asn
465

<210> SEQ ID NO 11
<211> LENGTH: 465
<212> TYPE: PRT
<213> ORGANISM: Macaca fascicularis

<400> SEQUENCE: 11

Met Glu Pro Ser Pro Leu Glu Leu Pro Ala Asp Thr Val Gln Arg Ile
1               5                   10                  15

Ala Thr Glu Leu Lys Cys His Pro Thr Asp Glu Arg Val Ala Leu His
            20                  25                  30

Leu Asp Glu Val Asp Lys Leu Arg His Phe Arg Glu Cys Phe Tyr Ile
            35                  40                  45

Pro Lys Ile Gln Asp Leu Pro Pro Val Asp Leu Ser Leu Val Asn Lys
        50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
            100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
        130                 135                 140
```

```
Leu Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Ser Met Arg Met Ile Lys Pro
            180                 185                 190

Arg Glu Gly Glu Thr Leu Arg Ile Glu Asp Ile Leu Glu Val Ile
            195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
                260                 265                 270

Cys Ser Tyr Lys Tyr Leu Asn Ala Gly Ala Gly Gly Ile Ala Gly Ala
            275                 280                 285

Phe Ile His Glu Lys His Ala His Thr Ile Lys Pro Ala Leu Val Gly
290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
                340                 345                 350

Thr Met Lys Ala Leu Arg Lys Lys Ser Ile Leu Leu Thr Gly Tyr Leu
            355                 360                 365

Glu Tyr Leu Ile Lys His Lys Tyr Gly Lys Asp Lys Ala Ala Thr Glu
    370                 375                 380

Lys Pro Ile Val Asn Ile Ile Thr Pro Ser His Ile Glu Glu Arg Gly
385                 390                 395                 400

Cys Gln Leu Thr Ile Thr Phe Ser Val Pro Asn Lys Asp Val Phe Gln
                405                 410                 415

Glu Leu Glu Lys Arg Gly Val Val Cys Asp Lys Arg Asn Pro Asn Gly
            420                 425                 430

Ile Arg Val Ala Pro Val Pro Leu Tyr Asn Ser Phe His Asp Val Tyr
            435                 440                 445

Lys Phe Thr Asn Leu Leu Thr Ser Ile Leu Asp Ser Ala Glu Thr Thr
450                 455                 460

Asn
465

<210> SEQ ID NO 12
<211> LENGTH: 465
<212> TYPE: PRT
<213> ORGANISM: Pan troglodytes

<400> SEQUENCE: 12

Met Glu Pro Ser Ser Val Glu Leu Pro Ala Asp Thr Val Gln Arg Ile
1               5                   10                  15

Ala Ala Glu Leu Lys Cys His Pro Thr Asp Glu Arg Val Ala Leu His
                20                  25                  30

Leu Asp Glu Glu Asp Lys Leu Arg His Phe Arg Glu Cys Phe Tyr Ile
            35                  40                  45
```

-continued

```
Pro Lys Ile Gln Asp Leu Pro Pro Val Asp Leu Ser Leu Val Asn Lys
 50                  55                  60

Asp Glu Asn Ala Ile Tyr Phe Leu Gly Asn Ser Leu Gly Leu Gln Pro
 65                  70                  75                  80

Lys Met Val Lys Thr Tyr Leu Glu Glu Leu Asp Lys Trp Ala Lys
                 85                  90                  95

Ile Ala Ala Tyr Gly His Glu Val Gly Lys Arg Pro Trp Ile Thr Gly
                    100                 105                 110

Asp Glu Ser Ile Val Gly Leu Met Lys Asp Ile Val Gly Ala Asn Glu
                115                 120                 125

Lys Glu Ile Ala Leu Met Asn Ala Leu Thr Val Asn Leu His Leu Leu
130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
                180                 185                 190

Arg Glu Gly Glu Thr Leu Arg Ile Glu Asp Ile Leu Glu Val Ile
                195                 200                 205

Glu Lys Glu Gly Asp Ser Ile Ala Val Ile Leu Phe Ser Gly Val His
210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
                260                 265                 270

Cys Ser Tyr Lys Tyr Leu Asn Ala Gly Ala Gly Gly Ile Ala Gly Ala
                275                 280                 285

Phe Ile His Glu Lys His Ala His Thr Ile Lys Pro Ala Leu Val Gly
290                 295                 300

Trp Phe Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Ala
                340                 345                 350

Thr Met Lys Ala Leu Arg Lys Lys Ser Val Leu Leu Thr Gly Tyr Leu
                355                 360                 365

Glu Tyr Leu Ile Lys His Asn Tyr Gly Lys Asp Lys Ala Ala Thr Lys
                370                 375                 380

Lys Pro Val Val Asn Ile Ile Thr Pro Ser His Val Glu Glu Arg Gly
385                 390                 395                 400

Cys Gln Leu Thr Ile Thr Phe Ser Val Pro Asn Lys Asp Val Phe Gln
                405                 410                 415

Glu Leu Glu Lys Arg Gly Val Val Cys Asp Lys Arg Asn Pro Asn Gly
                420                 425                 430

Ile Arg Val Ala Pro Val Pro Leu Tyr Asn Ser Phe His Asp Val Tyr
                435                 440                 445

Lys Phe Thr Asn Leu Leu Thr Ser Ile Leu Asp Ser Ala Glu Thr Thr
450                 455                 460
```

Asn
465

<210> SEQ ID NO 13
<211> LENGTH: 431
<212> TYPE: PRT
<213> ORGANISM: Arenitalea lutea

<400> SEQUENCE: 13

Met Leu Glu Thr Glu Asn Ile Arg Thr Leu Ser Asp Tyr Lys Leu Gly
1               5                   10                  15

Leu Asp Tyr Ala Leu Asp Gln Asp Arg Lys Asp Glu Leu Lys Ser Tyr
            20                  25                  30

Arg Asn Gln Phe His Ile Pro Lys Asp Lys Gln Gly Asp Ala Trp Ile
        35                  40                  45

Tyr Met Thr Gly Asn Ser Leu Gly Leu Gln Pro Lys Gln Thr Lys Ala
    50                  55                  60

Tyr Val Asn Gln Glu Leu Asn Asp Trp Ala Asn Leu Gly Val Glu Gly
65                  70                  75                  80

His Phe Glu Ala Lys Asn Pro Trp Leu Ala Tyr His Glu Phe Leu Thr
                85                  90                  95

Glu Ser Met Ala Lys Val Val Gly Ala Lys Pro Ile Glu Val Val Val
            100                 105                 110

Met Asn Thr Leu Thr Ala Asn Leu His Phe Met Met Val Ser Phe Tyr
        115                 120                 125

Lys Pro Thr Lys Thr Arg Tyr Lys Ile Leu Ile Glu Ser Asp Ala Phe
    130                 135                 140

Pro Ser Asp Lys Tyr Ala Val Glu Ser Gln Leu Arg His His Gly Phe
145                 150                 155                 160

Asp Asp Lys Glu Gly Val Val Leu Trp Lys Pro Arg Pro Gly Glu Glu
                165                 170                 175

Leu Leu Asn Tyr Asp Asp Leu Glu Thr Ile Leu Glu Thr Gln Gly Asp
            180                 185                 190

Glu Ile Ala Leu Ile Met Ile Gly Gly Val Asn Tyr Tyr Thr Gly Gln
        195                 200                 205

Tyr Phe Asp Leu Lys Arg Ile Thr Gln Leu Gly His Lys Gln Gly Cys
    210                 215                 220

Asn Val Gly Phe Asp Cys Ala His Gly Ala Gly Asn Val Ala Leu Asn
225                 230                 235                 240

Leu His Asp Ser Gly Ala Asp Phe Ala Val Trp Cys Thr Tyr Lys Tyr
                245                 250                 255

Leu Asn Ser Gly Pro Gly Ser Leu Ala Gly Cys Phe Val His Glu Arg
            260                 265                 270

His Ala Tyr Arg Lys Asp Leu Asn Arg Phe Thr Gly Trp Trp Ser His
        275                 280                 285

Asn Lys Gln Thr Arg Phe Asn Met Arg Gly Glu Phe Asp Gln Leu Pro
    290                 295                 300

Gly Ala Glu Gly Trp Gln Leu Ser Asn Pro Pro Ile Leu Ser Met Ala
305                 310                 315                 320

Ala Ile Lys Ala Ser Leu Asp Leu Phe Asn Glu Val Gly Met Asp Lys
                325                 330                 335

Leu Ile Asn Lys Ser Lys Lys Leu Thr Gly Tyr Phe Glu Tyr Leu Leu
            340                 345                 350

Lys Gln Leu Gly Glu Asp Thr Ile Arg Ile Thr Pro Lys Arg Ser
        355                 360                 365

```
Glu Arg Gly Cys Gln Leu Ser Ile Gln Val Lys Asn Ala Asp Lys
    370                 375                 380

Ser Leu His Asn Lys Leu Thr Glu Val Gly Ile Ile Ser Asp Trp Arg
385                 390                 395                 400

Glu Pro Asp Val Ile Arg Cys Ala Pro Val Pro Leu Tyr Asn Ser Phe
                405                 410                 415

Glu Asp Val Tyr Arg Leu Val Glu Lys Leu Lys Gly Ile Leu Lys
            420                 425                 430
```

<210> SEQ ID NO 14
<211> LENGTH: 429
<212> TYPE: PRT
<213> ORGANISM: Belliella Baltica DSM 15883

<400> SEQUENCE: 14

```
Met Ser Asn Gln Ile Asn Phe Glu Tyr Ser Leu Asp Phe Ala Gln Lys
1               5                   10                  15

Met Asp Glu Lys Asp Pro Leu Lys Ser Phe Arg Ser Lys Phe Phe
            20                  25                  30

Pro Lys Val Glu Asp Lys Glu Ala Ile Tyr Phe Cys Gly Asn Ser Leu
            35                  40                  45

Gly Leu Gln Pro Lys Thr Thr Gln Asn Tyr Ile Gln Lys Glu Leu Ser
        50                  55                  60

Asn Trp Ala Glu Met Ala Val Asp Gly His Phe His Gly Glu Asp Ala
65                  70                  75                  80

Trp Tyr His Ile Arg Lys Lys Ser Lys Pro Ala Leu Ala Glu Ile Val
                85                  90                  95

Gly Ala His Glu His Glu Val Val Ala Met Asn Asn Leu Thr Ser Asn
                100                 105                 110

Leu His Phe Leu Met Val Ser Phe Tyr Arg Pro Asn Ala Lys Arg Phe
            115                 120                 125

Lys Ile Ile Thr Glu Ala Gly Ala Phe Pro Ser Asp Met Tyr Met Leu
        130                 135                 140

Glu Thr Gln Val Lys Phe His Gly Leu Asp Pro Asn Lys Ala Ile Val
145                 150                 155                 160

Glu Leu Ala Pro Arg Asp Gly Glu His Thr Leu Arg Thr Glu Asp Ile
                165                 170                 175

Leu Gln Ser Ile Lys Glu Gln Gly Glu Leu Ala Leu Val Met Met
            180                 185                 190

Ala Gly Leu Gln Tyr Tyr Thr Gly Gln Val Phe Asp Met Lys Ala Ile
        195                 200                 205

Ala Gln Ala Val Lys Asp Glu Gly Ala Phe Val Gly Phe Asp Leu Ala
210                 215                 220

His Ala Ala Gly Asn Val Pro Leu Ala Leu His Asp Trp Gly Val Asp
225                 230                 235                 240

Phe Ala Thr Trp Cys Ser Tyr Lys Tyr Met Asn Ser Gly Pro Gly Asn
                245                 250                 255

Val Ser Gly Ile Phe Val His Glu Asn His Ala Glu Lys Pro Asp Met
            260                 265                 270

Ile Arg Phe Ala Gly Trp Trp Gly His Asp Glu Gly Arg Phe Lys
        275                 280                 285

Met Glu Lys Gly Phe Lys Pro Met Phe Gly Ala Asp Gly Trp Gln Leu
290                 295                 300

Ala Asn Ser Asn Val Leu Ala Leu Ala Ala His Gln Ala Ser Leu Asp
```

```
                305                 310                 315                 320
Ile Phe Gln Gln Ala Gly Ile Lys Thr Leu Arg Glu Lys Ser Glu Thr
                    325                 330                 335

Leu Thr Ser Tyr Leu Glu Phe Leu Ile Gln Lys Ile Ser Gly Asn Ser
                    340                 345                 350

Gly Val Leu Glu Ile Ile Thr Pro Lys Asn Ile Asn Glu Arg Gly Cys
                    355                 360                 365

Gln Leu Ser Leu Leu Val His Lys Gly Lys Ala Val Phe Asp Glu
                    370                 375                 380

Phe Tyr Lys Asn Gly Ile Val Gly Asp Trp Arg Asn Pro Asn Val Ile
385                 390                 395                 400

Arg Ile Ala Pro Thr Pro Leu Tyr Asn Ser Tyr Glu Asp Val Phe Arg
                    405                 410                 415

Phe Ala Lys Ile Leu Glu Gln Ser Leu Gln Lys Phe Ala
                    420                 425

<210> SEQ ID NO 15
<211> LENGTH: 422
<212> TYPE: PRT
<213> ORGANISM: Bizionia argentinensis

<400> SEQUENCE: 15

Met Ser Asn Phe Lys Thr Gly Ile Asp Phe Ala Lys Glu Gln Asp Glu
1               5                   10                  15

Asn Asp Thr Leu Ser Cys Tyr Arg Asn Gln Phe His Ile Pro Lys Asp
                20                  25                  30

Lys Gln Gly Asn Asp Met Ile Tyr Leu Cys Gly Asn Ser Leu Gly Leu
            35                  40                  45

Gln Pro Lys Ala Thr Lys Asp Tyr Ile Asn Gln Glu Leu Glu Asp Trp
        50                  55                  60

Ala Asn Leu Gly Val Glu Gly His Thr His Ala Lys Asn Pro Trp Leu
65                  70                  75                  80

Gly Tyr His Glu Phe Leu Thr Asp Ser Met Ala Lys Val Val Gly Ala
                85                  90                  95

Lys Pro Ile Glu Val Val Met Asn Thr Leu Thr Ala Asn Leu His
            100                 105                 110

Phe Met Met Val Ser Phe Tyr Lys Pro Thr Ile Glu Arg Tyr Lys Ile
        115                 120                 125

Ile Ile Glu Ala Asp Ala Phe Pro Ser Asp Lys Tyr Ala Val Glu Ser
130                 135                 140

Gln Leu Arg His His Gly Tyr Asp Asp Lys Glu Gly Leu Leu Leu Trp
145                 150                 155                 160

Lys Ala Arg Glu Gly Glu Glu Leu Leu Arg Tyr Glu Asp Leu Glu Ala
                165                 170                 175

Ile Leu Lys Glu His Gly Asp Asp Val Ala Leu Val Met Ile Gly Gly
            180                 185                 190

Val Asn Tyr Tyr Thr Gly Gln Phe Phe Asp Leu Lys Arg Ile Thr Glu
        195                 200                 205

Leu Gly His Lys His Gly Cys Met Val Gly Phe Asp Cys Ala His Gly
        210                 215                 220

Ala Gly Asn Val Glu Leu Asn Leu His Asp Ser Gly Ala Asp Phe Ala
225                 230                 235                 240

Val Trp Cys Thr Tyr Lys Tyr Leu Asn Ser Gly Pro Gly Ser Leu Gly
                245                 250                 255
```

-continued

Gly Cys Phe Val His Glu Arg His Ala His Asn Lys Arg Leu Asn Arg
            260                 265                 270

Phe Thr Gly Trp Trp Ser His Asn Lys Glu Thr Arg Phe Lys Met Arg
        275                 280                 285

Asp Glu Phe Asp Ala Ile Pro Gly Ala Glu Gly Trp Gln Leu Ser Asn
    290                 295                 300

Pro Pro Ile Leu Ser Met Ala Ala Ile Lys Ala Ser Leu Asp Ile Phe
305                 310                 315                 320

Glu Glu Ile Gly Met Lys Lys Leu Asn Glu Lys Ser Arg Ala Leu Thr
                325                 330                 335

Ala Tyr Phe Glu Phe Leu Leu Lys Gln Val Gly Asp Asp Ser Ile Arg
            340                 345                 350

Ile Ile Thr Pro Glu Asn Pro Asp Glu Arg Gly Cys Gln Leu Ser Ile
        355                 360                 365

Gln Val Lys Asn Ala Asp Arg Ser Leu His Asp Lys Leu Thr Asp Ala
    370                 375                 380

Gly Val Ile Ser Asp Trp Arg Glu Pro Asp Val Ile Arg Cys Ala Pro
385                 390                 395                 400

Ile Pro Leu Tyr Asn Ser Tyr Gln Asp Val Tyr His Met Val Glu Arg
                405                 410                 415

Leu Lys Asn Ile Leu Glu
            420

<210> SEQ ID NO 16
<211> LENGTH: 431
<212> TYPE: PRT
<213> ORGANISM: Candidatus Entotheonella sp. TSY2

<400> SEQUENCE: 16

Met Thr Ala Phe His Ala His Phe Gln Pro Thr Arg Glu Ala Ala Leu
1               5                   10                  15

Ala Leu Asp Ala Ser Asp Glu Leu Ala Pro Tyr Arg Asp Gln Phe Cys
            20                  25                  30

Leu Pro Gln Thr Gln Gly Gln Pro Val Val Tyr Leu Cys Gly His Ser
        35                  40                  45

Leu Gly Leu Gln Pro Lys Thr Val Arg Glu Tyr Ile Asp Glu Glu Leu
    50                  55                  60

Gln Asp Trp Ala Ala Leu Gly Val Glu Gly His Phe His Ala Arg Arg
65                  70                  75                  80

Pro Trp Leu Ser Tyr His Glu Ile Leu Thr Ala Gln Thr Ala Arg Leu
                85                  90                  95

Ala Gly Ala Lys Pro Ala Glu Val Val Val Met Asn Ser Leu Thr Val
            100                 105                 110

Asn Met His Leu Met Leu Val Ser Phe Tyr Arg Pro Thr Pro Glu Arg
        115                 120                 125

Phe Lys Ile Leu Ile Glu Ala Asp Ala Phe Pro Ser Asp Arg Tyr Ala
    130                 135                 140

Ala Glu Ser His Leu Arg Trp His Gly Tyr Asp Pro Gln Asp Ala Leu
145                 150                 155                 160

Leu Thr Leu Gln Pro Arg Pro Gly Glu Ala Ala Val Arg Gln Glu Asp
                165                 170                 175

Ile Ala Ala Phe Leu His Arg Glu Gly Glu Thr Ile Ala Leu Val Trp
            180                 185                 190

Leu Gly Gly Val Asn Tyr Tyr Thr Gly Gln Val Phe Asp Met Ala Glu
        195                 200                 205

Ile Thr Ala Ile Gly His Ala Gln Gly Cys Val Val Gly Phe Asp Leu
210                 215                 220

Ala His Ala Ala Gly Asn Ile Ile Leu Gln Leu His Asp Trp Asp Val
225                 230                 235                 240

Asp Cys Ala Val Trp Cys Ser Tyr Lys Tyr Leu Asn Ala Gly Pro Gly
                245                 250                 255

Ala Ala Ala Gly Cys Phe Val His Glu Arg Tyr Ala Gln Arg Pro Asp
            260                 265                 270

Leu Pro Arg Leu Ala Gly Trp Trp Gly His Asn Lys Asp Thr Arg Phe
        275                 280                 285

Gln Met Pro Ala Gly Phe Asp Pro Ile Pro Gly Ala Glu Gly Trp Gln
290                 295                 300

Ile Ser Asn Pro Pro Ile Phe Gln Leu Ala Ala Leu Lys Ala Ser Met
305                 310                 315                 320

Asp Ile Phe Asp Arg Ala Gly Met Met Arg Leu Arg Ala Lys Ser Glu
                325                 330                 335

Arg Leu Thr Gly Tyr Leu Glu Tyr Leu Leu Arg Asp Arg Ala Leu Pro
            340                 345                 350

Gly Val Ser Leu Ile Thr Pro Asp Asp Pro Ala Gln Arg Gly Ala Gln
        355                 360                 365

Leu Ser Leu Gln Ile Lys Gln His Gly Cys Ala Leu His Gln Arg Leu
370                 375                 380

Ala Glu Ala His Ile Ile Cys Asp Trp Arg Glu Pro Asp Val Ile Arg
385                 390                 395                 400

Val Ala Pro Val Pro Leu Tyr Asn Thr Phe Leu Asp Val Leu Thr Phe
                405                 410                 415

Val Asn Ala Leu Asp Thr Ala His Arg Glu Val Leu Val Ser Ser
            420                 425                 430

<210> SEQ ID NO 17
<211> LENGTH: 424
<212> TYPE: PRT
<213> ORGANISM: Candidatus Koribacter versatilis Ellin345

<400> SEQUENCE: 17

Met Ala Ala Ala Phe Asp Thr Thr Glu Asn Phe Ala Ile Glu Met
1               5                   10                  15

Asp Ala Arg Asp Pro Met Ser Arg Phe Arg Gly Arg Phe His Ile Pro
                20                  25                  30

Pro Ala Pro Asp Gly Ser Ala Ser Val Tyr Leu Val Gly His Ser Leu
            35                  40                  45

Gly Leu Gln Pro Lys Thr Val Arg Ala Tyr Leu Glu Gln Glu Leu Lys
        50                  55                  60

Asp Trp Glu Thr Leu Gly Val Glu Gly His Phe Arg Gly Lys His Pro
65                  70                  75                  80

Trp Met Pro Tyr His Arg Leu Thr Glu Gln Thr Ala Arg Leu Val
                85                  90                  95

Cys Ala Gln Pro Ser Glu Val Val Met Asn Ser Leu Thr Val Asn
            100                 105                 110

Leu His Leu Met Met Val Ser Phe Tyr Arg Pro Thr Arg Glu Arg His
        115                 120                 125

Asn Ile Leu Ile Glu Gly Ser Ala Phe Pro Ser Asp Gln Tyr Ala Val
130                 135                 140

Gln Ser Gln Ile Lys Phe His Gly Phe Asp Pro Ala Ser Ser Leu Leu

-continued

```
            145                 150                 155                 160
        Glu Leu Cys Pro Arg Val Gly Glu Ala Thr Met Arg Asp Glu Asp Ile
                        165                 170                 175

Leu Glu Leu Ile Glu Arg Glu Gly Gln Ser Ile Ala Leu Ile Leu Leu
                    180                 185                 190

Gly Gly Val Asn Tyr Ala Thr Gly Gln Ala Phe Asp Met Ala Glu Ile
                    195                 200                 205

Thr Lys Ala Gly His Ala Gln Gly Cys Val Val Ala Phe Asp Cys Ala
                    210                 215                 220

His Ala Ala Gly Asn Leu Glu Leu Lys Leu His Glu Trp Asp Val Asp
        225                 230                 235                 240

Trp Ala Ala Trp Cys Ser Tyr Lys Tyr Leu Asn Gly Pro Gly Gly Cys
                        245                 250                 255

Ile Gly Gly Cys Phe Val His Glu Arg Tyr Ala Arg Asp Phe Glu Leu
                        260                 265                 270

Pro Arg Phe Ala Gly Trp Trp Gly His Asp Gln Glu Thr Arg Phe Lys
                    275                 280                 285

Met Gly Pro Glu Phe His Pro Met Ala Gly Ala Glu Gly Trp Gln Leu
                    290                 295                 300

Ser Asn Pro Ser Ile Leu Thr Met Ala Ala Leu Arg Ala Ser Met Glu
        305                 310                 315                 320

Ile Phe Asp Glu Ala Gly Ile Gly Lys Leu Arg Gln Arg Ser Ile Ala
                        325                 330                 335

Leu Thr Gly Tyr Leu Glu Phe Leu Leu Asp Gln Gln Lys Ser Ala Arg
                    340                 345                 350

Phe Glu Ile Ile Thr Pro Arg Glu Pro Glu Arg Arg Gly Ala Gln Leu
                    355                 360                 365

Ser Ile Arg Val Ala Ala Gly Asn Arg Ser Val Cys Asp Arg Leu Val
                370                 375                 380

Glu Glu Gly Ala Leu Cys Asp Trp Arg Glu Pro Asp Ile Leu Arg Val
        385                 390                 395                 400

Ala Pro Val Pro Leu Tyr Cys Ser Tyr Arg Asp Cys Tyr Arg Phe Val
                        405                 410                 415

Gln Arg Phe Val Ala Asn Leu Asn
                        420

<210> SEQ ID NO 18
<211> LENGTH: 428
<212> TYPE: PRT
<213> ORGANISM: Cecembia lonarensis

<400> SEQUENCE: 18

Met Ser Asn Asn Gln Tyr Glu Phe Ser Glu Ser Phe Ala Arg Gln Met
        1               5                   10                  15

Asp Val Gln Asp Thr Leu Ser Gly Phe Arg Asp Arg Phe Tyr Phe Pro
                    20                  25                  30

Gln Ile Asn Gly Lys Glu Ala Ile Tyr Phe Cys Gly Asn Ser Leu Gly
                35                  40                  45

Leu Gln Pro Lys Thr Val Ala Thr Tyr Ile Asn Lys Glu Leu Asp Asn
            50                  55                  60

Trp Ala Lys Leu Gly Val Asp Gly His Phe Tyr Gly Glu Asp Ala Trp
        65                  70                  75                  80

Tyr His Val Arg Lys Lys Ser Lys Pro Ala Leu Ser Ala Ile Val Gly
                        85                  90                  95
```

```
Ala His Glu His Glu Val Val Ala Met Asn Asn Leu Thr Ser Asn Leu
            100                 105                 110

His Phe Leu Met Val Ser Phe Tyr Cys Pro Asp Gln Thr Arg Tyr Lys
        115                 120                 125

Ile Ile Thr Glu Ala Gly Ala Phe Pro Ser Asp Met Tyr Met Leu Glu
    130                 135                 140

Thr Gln Val Lys Phe His Gly Leu Asp Pro Glu Lys Cys Ile Val Glu
145                 150                 155                 160

Leu Ser Pro Arg Ala Gly Glu Tyr Thr Leu Arg Thr Glu Asp Ile Leu
                165                 170                 175

Met Ala Ile Glu Ala Asn Lys Glu Asn Leu Ala Leu Val Met Met Ala
            180                 185                 190

Gly Leu Gln Tyr Tyr Thr Gly Gln Val Phe Asp Met Lys Ala Ile Thr
        195                 200                 205

Ala Ala Ala His Gln Val Gly Ala Arg Ala Gly Phe Asp Leu Ala His
    210                 215                 220

Ala Val Gly Asn Ala Lys Leu Glu Leu His Asp Trp Gly Val Asp Phe
225                 230                 235                 240

Ala Thr Trp Cys Ser Tyr Lys Tyr Leu Asn Ser Gly Pro Gly Asn Ile
                245                 250                 255

Ser Gly Ile Phe Val His Glu Arg His Ala Glu Asn Gln Glu Leu Pro
            260                 265                 270

Arg Phe Ala Gly Trp Trp Gly His Asp Glu Gly Arg Phe Arg Met
        275                 280                 285

Glu Lys Gly Phe Lys Pro Met Tyr Gly Ala Asp Gly Trp Gln Leu Ala
    290                 295                 300

Asn Ser Asn Val Leu Ala Leu Ala Ala His Gln Ala Ser Leu Asp Ile
305                 310                 315                 320

Phe Glu Glu Ala Gly Met Asp Arg Leu Arg Ala Lys Ser Glu Leu Leu
                325                 330                 335

Thr Gly Tyr Leu Glu Phe Leu Ile Glu Lys Ile Ser Gly Asp Ser Gly
            340                 345                 350

Val Leu Glu Ile Ile Thr Pro Lys Ile Pro Asn Glu Arg Gly Cys Gln
        355                 360                 365

Leu Ser Leu Leu Ile His Lys Gly Lys Ser Val Phe Asp Glu Phe
    370                 375                 380

Tyr Lys His Gly Val Val Gly Asp Trp Arg Asn Pro Asn Val Ile Arg
385                 390                 395                 400

Leu Ala Pro Thr Pro Leu Tyr Asn Ser Phe Ile Asp Ile Tyr Gln Phe
                405                 410                 415

Ala Lys Ile Leu Glu Gln Ser Leu Gln Lys Phe Ala
            420                 425

<210> SEQ ID NO 19
<211> LENGTH: 421
<212> TYPE: PRT
<213> ORGANISM: Chlamydia pecorum PV3056/3

<400> SEQUENCE: 19

Met Ile Glu Lys Leu Lys Gln Tyr His Asp Glu Ala Ile Ser Leu Asp
1               5                   10                  15

Ser Leu Asp Pro Leu Gln Lys Phe Lys Glu Cys Phe Thr Leu Pro Lys
            20                  25                  30

Glu Pro Gly Ala Leu Tyr Phe Cys Ser Asn Ser Leu Gly Leu Pro Ala
        35                  40                  45
```

```
Lys Ala Ala Ser Gln Lys Leu Glu Glu Gln Leu Gln Arg Trp Ser Glu
         50                  55                  60

Leu Gly Ala Arg Gly Trp Phe Glu Gly Glu Gly Asn Trp Tyr Asn Ser
 65                  70                  75                  80

Leu Glu Glu Ser Ile Val Arg Pro Leu Ser Lys Ile Leu Gly Ala Glu
                 85                  90                  95

Ser Asn Glu Val Thr Leu Met Asn Ser Leu Thr Val Asn Leu His Met
            100                 105                 110

Leu Leu Ile Ser Phe Tyr Arg Pro Thr Lys Thr Arg Tyr Lys Ile Leu
        115                 120                 125

Ile Asp Gly Pro Ala Phe Pro Ser Asp Leu Tyr Ala Ile Lys Ser His
    130                 135                 140

Leu Arg Phe His Lys Lys Glu Glu Gly Leu Ile Leu Ile Glu Pro Arg
145                 150                 155                 160

Pro Gly Glu His Leu Val Gln Glu Glu Asp Phe Leu Arg Val Ile Lys
                165                 170                 175

Ile Gln Gly Glu Glu Ile Ala Leu Val Phe Leu Asn Cys Val Asn Phe
            180                 185                 190

Leu Ser Gly Gln Val Leu Lys Val Asp Glu Ile Thr Arg Tyr Ala Lys
        195                 200                 205

Glu Ala Gly Cys Cys Val Gly Tyr Asp Leu Ala His Ala Ala Gly Asn
    210                 215                 220

Ile Pro Leu Ser Leu His Asp Leu Gly Gly Asp Phe Ala Val Gly Cys
225                 230                 235                 240

Ser Tyr Lys Tyr Leu Cys Gly Gly Pro Gly Pro Gly Ile Ala Tyr
                245                 250                 255

Val His Ala Ser His His His Gln Gln Phe Val Arg Phe Ser Gly Trp
            260                 265                 270

Trp Gly Asn Asp Pro Asn Thr Arg Phe Tyr Phe Pro Lys Glu Phe Val
        275                 280                 285

Pro Tyr Gly Gly Ala Ser Ser Trp Gln Val Ser Thr Pro Ser Ile Leu
    290                 295                 300

Ala Lys Leu Pro Leu Ile Ala Ala Leu Glu Val Phe Glu Glu Ala Gly
305                 310                 315                 320

Met Glu Asn Ile Arg Glu Lys Ser Lys Lys Gln Thr Ala Phe Leu Tyr
                325                 330                 335

Thr Leu Leu Glu Asn Ala Arg Gly Thr His Phe Asp Met Ile Thr Pro
            340                 345                 350

Lys Glu Pro Glu Leu Arg Gly Cys Gln Leu Ser Leu Arg Ile Lys Cys
        355                 360                 365

Ser Arg Ser Glu Glu Ile Leu Arg Lys Leu Glu Arg Leu Gly Ile Thr
    370                 375                 380

Cys Asp Phe Arg Ser Pro Asn Ile Leu Arg Val Thr Pro Ser Pro Leu
385                 390                 395                 400

Tyr Thr Ser Phe Tyr Glu Ile Tyr Arg Phe Ala Tyr Thr Phe Leu Glu
                405                 410                 415

Val Leu Lys Thr Ile
            420

<210> SEQ ID NO 20
<211> LENGTH: 425
<212> TYPE: PRT
<213> ORGANISM: Chlamydophila caviae GPIC
```

```
<400> SEQUENCE: 20

Met Asn Glu Ile Leu Lys His Tyr Gln Lys Lys Ala Ala Gln Leu Asp
1               5                   10                  15

Glu Gln Asp Ser Leu Lys His Leu Arg Ala Arg Phe Ala Leu Pro Lys
            20                  25                  30

Asp Pro Asn Ala Ile Tyr Phe Cys Asn Asn Ser Leu Gly Leu Pro Ala
        35                  40                  45

Val Gly Ala Phe Thr Lys Ile Glu Glu Leu Leu Gln Arg Trp Ser Asp
    50                  55                  60

Val Gly Val Asn Gly Trp Phe Glu Gly Val Gly Asn Trp Tyr Arg Ser
65                  70                  75                  80

Phe Asp Asn Pro Leu Arg Gln Pro Leu Ser Lys Ile Leu Gly Ala Glu
                85                  90                  95

Tyr Glu Glu Val Val Val Met Asn Ser Leu Thr Met Asn Leu His Leu
                100                 105                 110

Leu Leu Val Ser Phe Tyr Arg Pro Thr Asp Thr Arg Tyr Lys Ile Leu
            115                 120                 125

Ile Glu Gly Pro Thr Phe Pro Ser Asp Leu Tyr Ala Ile Lys Ser Gln
130                 135                 140

Leu Ser Phe His Gly Lys Asn Pro Asp Asp Ala Leu Ile Ile Leu Glu
145                 150                 155                 160

Pro Arg Ala Gly Glu Asp Leu Leu Arg Tyr Glu Asp Phe Gln Gln Thr
                165                 170                 175

Leu Glu Glu Gln Gly Glu Ser Ile Ala Leu Val Phe Met Asn Cys Val
            180                 185                 190

Asn Phe Leu Thr Gly Gln Val Leu Glu Val Glu Ala Ile Thr Asn Leu
        195                 200                 205

Ala Lys Glu Lys Gly Cys Val Val Gly Cys Asp Leu Ala His Ala Ala
    210                 215                 220

Gly Asn Ile Pro Leu Lys Leu His Glu Trp Gly Val Asp Phe Ala Leu
225                 230                 235                 240

Gly Cys Ser Tyr Lys Tyr Leu Cys Gly Gly Pro Gly Gly Pro Gly Ile
                245                 250                 255

Ala Phe Val His Lys Ser His His Asn Glu Gln Leu Pro Arg Phe Ser
            260                 265                 270

Gly Trp Trp Gly Asn Asp Pro Glu Thr Arg Phe Gln Met Gln Leu Gln
        275                 280                 285

Pro Glu Phe Ile Pro Tyr Ser Gly Ala Tyr Ser Trp Gln Val Ser Thr
    290                 295                 300

Pro Ser Ile Val Ser Leu Met Pro Leu Leu Ala Thr Leu Glu Val Phe
305                 310                 315                 320

Glu Glu Ala Gly Met Glu Arg Val Arg His Lys Ser Lys Gln Met Thr
                325                 330                 335

Ala Phe Leu Leu Glu Leu Leu Glu Leu Ala Pro Pro Ser Cys Phe Glu
            340                 345                 350

Ile Ile Thr Pro Arg Asp Pro Glu Leu Arg Gly Ser Gln Leu Ser Ile
        355                 360                 365

Arg Ile Gln Gln His Ser Glu Glu Val Leu Gln Lys Leu Glu Ala Gln
370                 375                 380

Arg Ile Thr Cys Asp Ser Arg Pro Asp Ile Ile Arg Val Thr Ala
385                 390                 395                 400

Thr Pro Leu Tyr Asn Thr Phe Ser Glu Ile Tyr Lys Phe Thr Cys Lys
                405                 410                 415
```

```
Leu Phe Glu Val Leu Glu Ile Lys Ser
            420                 425

<210> SEQ ID NO 21
<211> LENGTH: 425
<212> TYPE: PRT
<213> ORGANISM: Corallococcus coralloides DSM 2259

<400> SEQUENCE: 21

Met Thr Ala Pro Val Tyr Glu Asn Thr Asp Val Phe Ala Tyr Gly Leu
1               5                   10                  15

Asp Ala Ala Asp Pro Leu Arg Pro Leu Arg Asp Glu Phe Leu Phe Pro
            20                  25                  30

Pro Ala Pro Ser Gly Ala Pro Ala Ile Tyr Leu Ala Gly Asn Ser Leu
        35                  40                  45

Gly Leu Gln Pro Arg Lys Ala Arg Lys Tyr Val Gln Met Glu Met Glu
    50                  55                  60

Asp Trp Glu Arg Leu Gly Val Glu Gly His Val His Gly Arg His Pro
65                  70                  75                  80

Trp Leu Pro Tyr His Glu Gln Leu Thr Asp Met Val Ala Arg Val Val
                85                  90                  95

Gly Ala Gln Pro Ile Glu Val Val Met Asn Thr Leu Ser Val Asn
            100                 105                 110

Leu His Leu Met Met Val Ser Phe Tyr Arg Pro Thr Arg Glu Arg Phe
        115                 120                 125

Lys Ile Leu Ile Glu Gly Gly Ala Phe Pro Ser Asp Gln Tyr Ala Val
130                 135                 140

Ala Ser Gln Ala Arg Phe His Gly Tyr Asp Pro Lys Glu Ala Ile Val
145                 150                 155                 160

Arg Leu Met Pro Arg Glu Gly Glu Asp Thr Leu Arg Ser Glu Asp Ile
                165                 170                 175

Leu Glu Ala Ile Glu Arg His Gly Lys Glu Leu Ala Leu Val Met Leu
            180                 185                 190

Gly Ser Val Asn Tyr Leu Thr Gly Gln Ala Phe Asp Leu Arg Glu Ile
        195                 200                 205

Thr Arg Val Ala His Ala Gln Gly Cys Lys Val Gly Phe Asp Leu Ala
    210                 215                 220

His Ala Ala Gly Asn Leu Lys Leu Ser Leu His Asp Asp Gly Pro Asp
225                 230                 235                 240

Phe Ala Val Trp Cys Ser Tyr Lys Tyr Leu Asn Gly Gly Pro Gly Ser
                245                 250                 255

Leu Gly Gly Val Phe Val His Glu Arg His Ala His Ser Pro Gln Leu
            260                 265                 270

Pro Arg Phe Glu Gly Trp Trp Gly His Asn Lys Ala Thr Arg Phe Glu
        275                 280                 285

Met Gly Pro Thr Phe Asp Pro Leu Pro Gly Ala Glu Gly Trp Gln Leu
    290                 295                 300

Ser Asn Pro Pro Ile Phe Gln Leu Ala Ala Leu Arg Ser Ser Leu Glu
305                 310                 315                 320

Leu Phe Asp Lys Ala Thr Met Ala Ala Leu Arg Thr Lys Ser Asp Gln
                325                 330                 335

Leu Thr Gly Tyr Leu Glu Phe Leu Leu Asp Arg Leu Pro Ala Gly Tyr
            340                 345                 350

Val Ser Ile Thr Thr Pro Arg Asp Leu Lys Gln Arg Gly Ala Gln Leu
```

```
                355                 360                 365
Ser Leu Arg Phe Lys Gly Glu Pro Lys Arg Leu Leu Gln Arg Leu Ser
        370                 375                 380

Ala Ala Gly Ile Ile Cys Asp Phe Arg Glu Pro Asp Ile Ile Arg Ala
385                 390                 395                 400

Ala Pro Thr Pro Leu Tyr Asn Thr Tyr Leu Asp Val Phe Arg Phe Val
                405                 410                 415

Lys Ala Leu Glu Ala His Ala Leu Glu
                420                 425

<210> SEQ ID NO 22
<211> LENGTH: 426
<212> TYPE: PRT
<213> ORGANISM: Cyclobacterium marinum DSM 745

<400> SEQUENCE: 22

Met Asp Gln Ile Ala Phe Glu Leu Thr Pro Glu Phe Ala Arg Lys Met
1               5                   10                  15

Asp Leu Ala Asp Pro Leu Ser Thr Tyr Arg Glu Lys Phe Tyr Ile Pro
                20                  25                  30

Glu Lys Asn Gly Gln Pro Leu Ile Tyr Phe Cys Gly Asn Ser Leu Gly
            35                  40                  45

Leu Gln Pro Arg Ser Val Asn Ala Tyr Leu Lys Gln Glu Leu Glu Lys
        50                  55                  60

Trp Ala Asp Lys Gly Val Asp Gly His Phe Glu Gly Lys Val Pro Trp
65              70                  75                  80

Ile Asp Ala Arg Lys Pro Ser Lys Arg Leu Ile Ala Pro Leu Val Gly
                85                  90                  95

Ala Asn Glu Gln Glu Val Val Ala Met Asn Ser Leu Ser Val Asn Leu
            100                 105                 110

His Leu Leu Met Val Ser Phe Tyr Gln Pro Lys Gly Lys Lys Phe Lys
        115                 120                 125

Ile Leu Thr Glu Ala Gly Ala Phe Pro Ser Asp Gln Tyr Ile Leu Glu
130                 135                 140

Ser Gln Val Lys Phe His Gly Leu Leu Pro Asp Glu Ala Ile Leu Glu
145                 150                 155                 160

Met Ala Pro Arg Pro Asn Glu His Leu Leu Arg Thr Glu Asp Ile Leu
                165                 170                 175

Gln Lys Ile Glu Asp His Lys Asp Glu Leu Ala Leu Ile Met Leu Ser
            180                 185                 190

Gly Leu Gln Tyr Tyr Thr Gly Gln Leu Phe Asp Leu Glu Ala Ile Ser
        195                 200                 205

Ser Ala Ala Asn Lys Gln Gly Ile Thr Ile Gly Phe Asp Leu Ala His
210                 215                 220

Ala Ile Gly Asn Val Pro Leu Arg Leu His Asp Trp Gly Val Asp Phe
225                 230                 235                 240

Ala Thr Trp Cys Ser Tyr Lys Tyr Leu Asn Ser Gly Pro Gly Asn Val
                245                 250                 255

Ser Gly Ile Phe Val His Glu Lys His Ser Asp Asn Ala Leu Leu Pro
            260                 265                 270

Arg Phe Ala Gly Trp Trp Gly His Asp Glu Lys Glu Arg Phe Lys Met
        275                 280                 285

Lys Lys Gly Phe Lys His Met Pro Gly Ala Asp Gly Trp Leu Leu Ser
            290                 295                 300
```

```
Asn Asp Asn Val Leu Gly Leu Ala Ala His Gln Ala Ser Leu Glu Leu
305                 310                 315                 320

Phe Ala Glu Ala Gly Leu Asp Lys Leu Arg Lys Lys Ser Ile Gln Leu
                325                 330                 335

Thr Asn Tyr Leu Glu Phe Ala Ile His Glu Thr Ile Lys Asp Ser Glu
                340                 345                 350

Leu Leu Glu Ile Ile Thr Pro Leu Lys Pro Thr Glu Arg Gly Cys Gln
                355                 360                 365

Leu Ser Leu Leu Ile His Lys Lys Gly Lys Glu Val Phe Asp Tyr Trp
        370                 375                 380

Ile Asp Asn Gly Val Val Ala Asp Trp Arg Asn Pro Asn Val Ile Arg
385                 390                 395                 400

Leu Ala Pro Thr Pro Met Tyr Asn Thr Phe Gln Asp Val Phe Glu Phe
                405                 410                 415

Ser Arg Ile Leu Lys Asn Ser Leu Glu Ala
                420                 425
```

<210> SEQ ID NO 23
<211> LENGTH: 426
<212> TYPE: PRT
<213> ORGANISM: Cystobacter fuscus

<400> SEQUENCE: 23

```
Met Ser Gly Glu Ala Val Arg Phe Glu Pro Gly Glu Ala Phe Ala Arg
1               5                   10                  15

Arg Met Asp Ala Glu Asp Pro Leu Arg Ser Phe Arg Glu Glu Phe Leu
                20                  25                  30

Phe Pro Val His Gly Asp Gly His Glu Leu Tyr Leu Leu Gly Asn Ser
                35                  40                  45

Leu Gly Leu Gln Pro Arg Lys Ala Lys Glu Tyr Val Leu Ala Ala Met
        50                  55                  60

Glu Asp Trp Ala Arg Leu Gly Val Asp Gly His Phe Lys Gly Ser Pro
65                  70                  75                  80

Pro Trp Met Glu Phe His Val Gly Leu Gly Glu Gln Met Ala Arg Val
                85                  90                  95

Val Gly Ala Arg Pro Glu Glu Val Val Val Met Asn Thr Leu Thr Val
                100                 105                 110

Asn Leu His Leu Met Met Val Ser Phe Tyr Arg Pro Thr Pro Glu Arg
                115                 120                 125

Ser Lys Ile Leu Met Glu Ala Ser Ala Phe Pro Ser Asp Gln Tyr Ala
                130                 135                 140

Val Ala Ala Gln Val Arg His His Gly Tyr Ser Pro Glu Gln Thr Val
145                 150                 155                 160

Ile Pro Leu Ala Pro Arg Pro Gly Glu His Thr Leu Arg His Glu Asp
                165                 170                 175

Ile Leu Asp Thr Leu Glu Arg His Gly Lys Glu Ile Ala Leu Val Leu
                180                 185                 190

Leu Gly Asn Val Asn Tyr Leu Thr Gly Gln Ala Phe Asp Met Ala Ala
        195                 200                 205

Ile Thr Arg Ala Ala His Gln Arg Gly Cys Arg Val Gly Phe Asp Leu
                210                 215                 220

Ala His Ala Ala Gly Asn Leu Arg Leu Ser Leu His Glu Asp Gly Pro
225                 230                 235                 240

Asp Phe Ala Val Trp Cys Thr Tyr Lys Tyr Leu Asn Gly Gly Pro Gly
                245                 250                 255
```

```
Ala Leu Gly Gly Val Phe Ile His Glu Arg His Leu Arg Asp Ala Ser
            260                 265                 270

Leu His Arg Leu Pro Gly Trp Trp Gly Asn Asp Arg Gly Thr Arg Phe
        275                 280                 285

Gln Met Lys Pro Asp Phe Glu Pro Ala Pro Gly Ala Glu Gly Trp Val
    290                 295                 300

Leu Ser Asn Pro Pro Ile Ile Gln Met Ala Ala Leu Arg Ala Ser Leu
305                 310                 315                 320

Glu Leu Phe Asp Arg Ala Thr Met Pro Ala Leu Arg Ala Lys Ser Glu
                325                 330                 335

Lys Leu Thr Gly Tyr Leu Glu Phe Leu Ile Asp Arg Leu Pro Glu Gly
            340                 345                 350

Phe Val His Ser Leu Thr Pro Arg Asp Pro Gly Gln Arg Gly Ala His
        355                 360                 365

Leu Ser Leu Arg Phe Thr Lys Asp Pro Gln Arg Met Leu Glu Thr Leu
    370                 375                 380

Arg Ala Glu Gly Ile His Cys Asp Phe Arg Tyr Pro Asp Ile Ile Arg
385                 390                 395                 400

Ala Ala Pro Val Pro Leu Tyr Asn Ser Phe Leu Asp Val His Arg Phe
                405                 410                 415

Val Ser Val Leu Glu Arg Tyr Ala Arg Gly
            420                 425

<210> SEQ ID NO 24
<211> LENGTH: 426
<212> TYPE: PRT
<213> ORGANISM: Echinicola vietnamensis DSM 17526

<400> SEQUENCE: 24

Met Ser Ser Tyr Arg Tyr Ser Leu Ala Phe Ala Gln Glu Arg Asp Arg
1               5                   10                  15

Glu Asp Pro Leu Arg Lys Phe Gln Ser Arg Phe His Phe Pro Lys Val
            20                  25                  30

Asn Gly Glu Ala Ala Ile Tyr Phe Cys Gly Asn Ser Leu Gly Leu Gln
        35                  40                  45

Pro Lys Ala Val Arg Glu His Leu Asp Arg Asp Leu Glu Ser Trp Ala
    50                  55                  60

Ser Lys Ala Val Asp Gly His Phe Glu Gly Asp Ala Pro Trp Phe Ser
65                  70                  75                  80

Val His Glu Arg Ser Lys Ala Ala Leu Ala Glu Ile Val Gly Ala Lys
                85                  90                  95

Lys His Glu Val Val Ala Met Gly Ser Leu Thr Thr Asn Leu His Ala
            100                 105                 110

Leu Leu Val Ser Phe Tyr Gln Pro Asn Gly Lys Arg Asn Lys Ile Leu
        115                 120                 125

Thr Glu Ala Gly Ala Phe Pro Ser Asp Met Tyr Ala Leu Glu Ser Gln
    130                 135                 140

Val Lys Tyr His Gly Leu Asp Pro Asp Glu Ala Ile Val Glu Val Gly
145                 150                 155                 160

Pro Arg Pro Gly Glu His Thr Ile Arg Thr Glu Asp Ile Leu Gln Ala
                165                 170                 175

Ile Ser Lys His Gln Asp Glu Leu Ala Cys Val Met Met Ala Gly Leu
            180                 185                 190

Gln Tyr Tyr Thr Gly Gln Val Phe Asp Met Lys Ala Ile Ala Ser Ala
```

```
            195                 200                 205
Ala His Ala Val Gly Ala Thr Val Gly Phe Asp Leu Ala His Ala Ala
    210                 215                 220

Gly Asn Ala Pro Leu His Leu His Asp Trp Gly Val Asp Phe Ala Ala
225                 230                 235                 240

Trp Cys Ser Tyr Lys Tyr Leu Asn Ser Gly Pro Gly Asn Val Ala Gly
                245                 250                 255

Ile Phe Val His Glu Arg His Gly Asn Asn Pro Ala Leu Asn Arg Phe
                260                 265                 270

Ala Gly Trp Trp Gly His Asp Glu Lys Val Arg Phe Lys Met Glu Lys
            275                 280                 285

Gly Phe Val Pro Met Tyr Gly Ala Asp Gly Trp Gln Asn Ser Asn Gly
290                 295                 300

Asn Val Leu Gly Met Ala Ala His Gln Ala Ser Leu Asp Ile Phe Gln
305                 310                 315                 320

Glu Ala Gly Met Val His Leu Arg Lys Lys Ser Val Gln Leu Thr Gly
                325                 330                 335

Phe Leu Ala Phe Leu Ile Arg Glu Ile Ser Gly Glu Ser Gly Val Leu
                340                 345                 350

Glu Val Ile Thr Pro Asn Ala Glu Ala Glu Arg Gly Cys Gln Leu Ser
                355                 360                 365

Leu Leu Ile His Lys Gly Gly Lys Ala Val Phe Asp Glu Phe Tyr Gln
370                 375                 380

Asn Gly Ile Val Gly Asp Trp Arg Asn Pro Asn Val Ile Arg Ile Ala
385                 390                 395                 400

Pro Thr Pro Leu Tyr Asn Ser Phe Glu Asp Val Phe Arg Phe Ala Lys
                405                 410                 415

Ile Leu Glu Gln Ser Leu Ser Lys Phe Ala
                420                 425

<210> SEQ ID NO 25
<211> LENGTH: 420
<212> TYPE: PRT
<213> ORGANISM: Flavobacteria bacterium BBFL7

<400> SEQUENCE: 25

Met Glu Phe Asn Thr Thr Arg Asp Tyr Ala Leu Gln Leu Asp Gln Glu
1               5                   10                  15

Asp Ser Leu Ser Arg Phe Arg Glu Ser Phe His Ile Pro Lys His Thr
            20                  25                  30

Asp Gly Thr Asp Ser Ile Tyr Leu Cys Gly Asn Ser Leu Gly Leu Gln
        35                  40                  45

Pro Arg Gln Thr Lys Thr Phe Leu Asn Gln Glu Leu Asp Asp Trp Ala
    50                  55                  60

Lys Leu Gly Val Glu Gly His Phe His Ala Glu Asn Pro Trp Met Pro
65                  70                  75                  80

Tyr His Glu Phe Leu Thr Glu Thr Thr Ala Gln Val Val Gly Ala Lys
                85                  90                  95

Pro His Glu Val Val Ile Met Asn Thr Leu Thr Thr Asn Leu His Leu
            100                 105                 110

Met Met Val Ser Phe Tyr Gln Pro Lys Gly Lys Arg Thr Lys Ile Ile
        115                 120                 125

Ile Glu Ala Asp Ala Phe Pro Ser Asp Arg Tyr Ala Val Ala Ser Gln
    130                 135                 140
```

```
Val Gln Phe His Gly His Asp Asp Lys Glu Asn Ile Ile Glu Trp Ala
145                 150                 155                 160

Pro Arg Thr Gly Glu His Thr Pro Arg Leu Glu Asp Leu Glu Thr Ile
                165                 170                 175

Leu Lys Glu Gln Gly Asp Glu Ile Ala Leu Ile Met Val Gly Ala Val
            180                 185                 190

Asn Tyr Tyr Thr Gly Gln Phe Phe Asp Leu Lys Lys Ile Thr Glu Leu
        195                 200                 205

Gly His Ala Ala Gly Ala Met Val Gly Phe Asp Cys Ala His Gly Ala
    210                 215                 220

Gly Asn Val Asp Leu Gln Leu His Asp Ser Gly Ala Asp Phe Ala Val
225                 230                 235                 240

Trp Cys Thr Tyr Lys Tyr Met Asn Ser Gly Pro Gly Ser Leu Gly Gly
                245                 250                 255

Cys Phe Val His Glu Arg His Ala Asn Asn Ser Glu Leu Pro Arg Phe
                260                 265                 270

Thr Gly Trp Trp Gly His Asn Lys Asp Thr Arg Phe Lys Met Arg Asp
            275                 280                 285

Asp Phe Glu Pro Met His Gly Ala Glu Gly Trp Gln Leu Ser Asn Pro
290                 295                 300

Pro Ile Leu Ser Met Val Ala Ile Arg Ala Ser Leu Asp Leu Phe Ala
305                 310                 315                 320

Gln Ala Gly Phe Glu Asn Leu Arg Lys Lys Ser Ile Gln Leu Thr Asn
                325                 330                 335

Tyr Leu Glu Tyr Leu Val Gly Glu Leu Asp Gly Asp Arg Ile Ser Ile
            340                 345                 350

Ile Thr Pro Arg Asp Pro Lys Asp Arg Gly Cys Gln Leu Ser Leu Ala
        355                 360                 365

Val Lys Asn Ala Asp Lys Ser Leu Phe Asp Ala Ile Thr Ala Lys Gly
    370                 375                 380

Val Ile Ala Asp Trp Arg Glu Pro Asp Val Ile Arg Ile Ala Pro Val
385                 390                 395                 400

Pro Leu Tyr Asn Asn Tyr Glu Asp Cys Trp Arg Phe Val Asp Val Leu
                405                 410                 415

Lys Ser Glu Leu
            420

<210> SEQ ID NO 26
<211> LENGTH: 442
<212> TYPE: PRT
<213> ORGANISM: Flexibacter litoralis DSM 6794

<400> SEQUENCE: 26

Met Asn Phe Glu Thr Thr Lys Asn Phe Ala Ser Gln Leu Asp Asn Asn
1               5                   10                  15

Asp Ser Leu Ala His Phe Arg Asp Lys Phe Trp Ile Pro Thr Leu Asn
            20                  25                  30

Ser Ile Ser Lys Asn Thr Asn Ser Ser Asn Glu Lys Gly Lys Glu Lys
        35                  40                  45

Val Val Tyr Phe Cys Gly Asn Ser Leu Gly Leu Gln Pro Lys Thr Thr
    50                  55                  60

Lys Ala Tyr Ile Glu Gln Glu Leu Glu Asp Trp Lys Asn Leu Gly Val
65                  70                  75                  80

Glu Gly His Phe His Gly Lys Asn Pro Trp Leu Ser Tyr His Lys Leu
                85                  90                  95
```

```
Leu Thr Asn Gln Thr Ala Lys Ile Val Gly Ala Lys Pro Ile Glu Val
            100                 105                 110

Val Val Met Asn Asn Leu Thr Val Asn Leu His Leu Met Val Ser
            115                 120                 125

Phe Tyr Arg Pro Asn Gln Lys Arg Phe Lys Ile Leu Met Glu Gly Gly
130                 135                 140

Ala Phe Pro Ser Asp Gln Tyr Ala Ile Glu Ser Gln Val Lys Phe His
145                 150                 155                 160

Gly Phe Ser Pro Asp Asp Ala Ile Val Glu Met Met Pro Arg Lys Asn
                165                 170                 175

Glu Asn Ser Glu Gly Glu Glu Thr Leu Arg Thr Glu Asp Ile Leu Lys
            180                 185                 190

Lys Ile Glu Glu Leu Gly Asp Glu Leu Ala Leu Val Met Phe Gly Gly
            195                 200                 205

Val Asn Tyr Tyr Thr Gly Gln Phe Phe Asp Leu Glu Lys Ile Thr Gln
            210                 215                 220

Ala Ala His Lys Val Gly Ala Thr Ala Gly Phe Asp Leu Ala His Ala
225                 230                 235                 240

Ala Gly Asn Val Pro Leu Lys Leu His Asp Trp Lys Val Asp Phe Ala
                245                 250                 255

Thr Trp Cys Ser Tyr Lys Tyr Leu Asn Ser Gly Ala Gly Thr Ser
            260                 265                 270

Gly Val Phe Ile Asn Glu Lys Tyr Ala Asp Asp Ser Leu Pro Arg
            275                 280                 285

Phe Ala Gly Trp Trp Gly His Asp Glu Lys Asp Arg Phe Lys Met Lys
290                 295                 300

Lys Gly Phe Ile Pro Met Arg Gly Ala Glu Gly Trp Gln Leu Ser Asn
305                 310                 315                 320

Ala Gln Ile Leu Pro Met Ala Val His Lys Ala Ser Leu Asp Ile Phe
                325                 330                 335

Glu Glu Ala Gly Phe Glu Asn Leu Arg Gln Lys Ser Glu Gln Leu Thr
            340                 345                 350

Val Tyr Met Glu Phe Leu Ile Glu Asn Phe Asn Lys Gln Ser Lys
            355                 360                 365

Ile Lys Ile Lys Ile Ile Thr Pro Lys Asn Lys Leu Glu Arg Gly Cys
370                 375                 380

Gln Leu Ser Leu Val Phe Asp Lys Glu Gly Lys Lys Tyr His Glu Thr
385                 390                 395                 400

Leu Thr Lys Arg Gly Val Ile Ser Asp Trp Arg Glu Pro Asn Val Ile
                405                 410                 415

Arg Ile Ala Pro Ile Pro Leu Tyr Asn Ser Phe Met Asp Cys Tyr Arg
            420                 425                 430

Phe Tyr Glu Ile Leu Lys Glu Ile Ala Val
            435                 440

<210> SEQ ID NO 27
<211> LENGTH: 423
<212> TYPE: PRT
<213> ORGANISM: Formosa sp. AK20

<400> SEQUENCE: 27

Met Ser Asn Tyr Lys Pro Gly Leu Asp Tyr Ala Lys Glu Gln Asp Gln
1               5                   10                  15

Asn Asp Ala Leu Ser His Tyr Arg Ser Gln Phe His Ile Pro Lys Asp
```

```
            20                  25                  30
Asn Gln Gly Asn Asn Trp Leu Tyr Phe Thr Gly Asn Ser Leu Gly Leu
             35                  40                  45

Gln Pro Lys Ser Thr Gln Lys Tyr Ile Gln Gln Glu Leu Asp Asp Trp
 50                  55                  60

Ala Asn Leu Gly Val Glu Gly His Phe Glu Ala Lys Asn Pro Trp Met
 65                  70                  75                  80

Pro Tyr His Glu Phe Leu Thr Asp Ser Met Ala Lys Ile Val Gly Ala
                 85                  90                  95

Lys Pro Ile Glu Val Val Thr Met Asn Thr Leu Thr Thr Asn Leu His
                100                 105                 110

Leu Leu Met Val Ser Phe Tyr Gln Pro Thr Lys Thr Lys Tyr Lys Ile
             115                 120                 125

Val Ile Glu Ser Asp Ala Phe Pro Ser Asp Arg Tyr Ala Val Gln Thr
         130                 135                 140

Gln Leu Glu Phe His Gly Phe Asp Ala Asn Glu Gly Leu Ile Glu Trp
145                 150                 155                 160

Lys Pro Arg Gln Gly Glu Glu Leu Leu Asn Leu Asp Asp Leu Glu Thr
                165                 170                 175

Ile Leu Glu Glu Gln Gly Asp Glu Ile Ala Leu Leu Leu Ile Gly Gly
            180                 185                 190

Val Asn Tyr Tyr Thr Gly Gln Tyr Leu Asp Leu Lys Lys Ile Ala Glu
        195                 200                 205

Leu Gly His Ala Lys Asn Cys Met Val Gly Ile Asp Leu Ala His Gly
    210                 215                 220

Ala Gly Asn Ile Lys Pro Glu Leu His Asp Ser Gly Val Asp Phe Ala
225                 230                 235                 240

Ala Trp Cys Thr Tyr Lys Tyr Leu Asn Ser Gly Pro Gly Ser Leu Gly
                245                 250                 255

Gly Leu Phe Val His Glu Lys His Ala His Asn Lys Lys Leu Lys Arg
            260                 265                 270

Phe Ala Gly Trp Trp Ser His Asn Lys Ala Thr Arg Phe Asn Met Arg
        275                 280                 285

Gln Pro Leu Asp Val Ile Pro Gly Ala Glu Gly Trp Gln Leu Ser Asn
    290                 295                 300

Pro Pro Ile Leu Ser Met Ala Ile Lys Ala Ser Leu Asp Met Phe
305                 310                 315                 320

Asn Glu Val Gly Met Asp Ala Leu Arg Glu Lys Ser Glu Lys Leu Thr
                325                 330                 335

Gly Tyr Phe Glu Phe Leu Leu Asn Glu Leu Asn Asn Asp Lys Val Lys
            340                 345                 350

Ile Ile Thr Pro Ser Asn Pro Lys Glu Arg Gly Cys Gln Leu Ser Ile
        355                 360                 365

Gln Val Arg Asp Ala Asp Lys Ser Leu His Lys Lys Leu Thr Lys Ala
    370                 375                 380

His Ile Ile Thr Asp Trp Arg Glu Pro Asp Val Ile Arg Cys Ala Pro
385                 390                 395                 400

Val Pro Leu Tyr Asn Ser Phe Glu Asp Val Tyr Arg Met Val Asp Lys
                405                 410                 415

Leu Lys Gln Ile Leu Asn Thr
            420

<210> SEQ ID NO 28
```

<211> LENGTH: 429
<212> TYPE: PRT
<213> ORGANISM: Fulvivirga imtechensis

<400> SEQUENCE: 28

| Met<br>1 | Ala | Lys | Asp | Ile<br>5 | Leu | His | Met | Thr | Tyr<br>10 | Glu | Asn | Ser | Leu | Thr<br>15 | Phe |

Ala Gln Asp Leu Asp Arg Asp Pro Leu Arg His Phe Arg Asn Lys
                20                  25                  30

Phe His Ile Pro Gln Leu Asn Asp Lys Asp Val Ile Tyr Phe Thr Gly
            35                  40                  45

Asn Ser Leu Gly Leu Gln Pro Lys Asn Thr Arg Val Tyr Ile Glu Glu
 50                  55                  60

Glu Leu Glu Gly Trp Ala Thr Leu Gly Val Asp Gly His Phe His Ser
65                  70                  75                  80

Gln Lys Arg Pro Trp Phe Tyr His Lys Phe Ser Lys Glu Ala Leu
                85                  90                  95

Ala Lys Ile Val Gly Ala Lys Pro Ser Glu Val Val Ser Met Asn Asn
            100                 105                 110

Leu Thr Val Asn Leu His Leu Met Met Val Ser Phe Tyr Arg Pro Thr
        115                 120                 125

Ser Ser Arg Phe Lys Ile Met Ile Glu Ala Gly Ala Phe Pro Ser Asp
130                 135                 140

Gln Tyr Ala Val Glu Ser Gln Ile Lys Phe His Gly Tyr Asn Tyr Glu
145                 150                 155                 160

Asp Ala Leu Ile Glu Ile Ser Pro Arg Glu Gly Glu Tyr His Leu Arg
                165                 170                 175

Thr Glu Asp Ile Leu Ser Lys Ile Glu Glu Asn Lys Asp Ser Leu Ala
            180                 185                 190

Leu Val Leu Phe Gly Gly Val Gln Tyr Tyr Thr Gly Gln Leu Phe Asp
        195                 200                 205

Ile Gly Ser Ile Thr Ala Ala Gly His Trp Ala Gly Ala Ile Val Gly
210                 215                 220

Phe Asp Leu Ala His Ala Ala Gly Asn Val Pro Leu Asn Leu His Asn
225                 230                 235                 240

Asp Gln Val Asp Phe Ala Ala Trp Cys Ser Tyr Lys Tyr Leu Asn Ser
                245                 250                 255

Gly Pro Gly Gly Val Ser Gly Ile Phe Val His Glu Lys His Gly Asp
            260                 265                 270

Ala Glu Leu Pro Arg Phe Ala Gly Trp Trp Gly His Asn Glu Ser Glu
        275                 280                 285

Arg Phe Lys Met Lys Lys Gly Phe Ile Pro Met Ser Gly Ala Asp Gly
290                 295                 300

Trp Gln Leu Ser Asn Val Asn Ile Leu Ser Ser Ala Ala His Leu Ala
305                 310                 315                 320

Ala Leu Glu Ile Tyr Asp Glu Ala Gly Met Glu Ala Leu Arg Gln Lys
                325                 330                 335

Ser Ile Arg Leu Thr Gly Phe Met Glu Tyr Leu Leu Asn Gly Phe Asn
            340                 345                 350

Leu Gly Asp Asp Val Leu Lys Ile Ile Thr Pro Thr Asp Pro Ala Ala
        355                 360                 365

Arg Gly Cys Gln Leu Ser Leu Leu Val Ser Lys Asn Gly Lys Ala Ile
370                 375                 380

Phe Glu His Leu Thr Arg Ser Gly Val Val Ala Asp Trp Arg Glu Pro

```
                385                 390                 395                 400
Asp Val Ile Arg Val Ala Pro Val Pro Leu Tyr Asn Thr Phe Glu Asp
                    405                 410                 415

Val Tyr Asn Phe Cys Glu Ile Leu Lys Lys Val Ile Phe
                420                 425

<210> SEQ ID NO 29
<211> LENGTH: 425
<212> TYPE: PRT
<213> ORGANISM: Kangiella aquimarina

<400> SEQUENCE: 29

Met Thr Asp Ile Phe Ser Ile Asp Tyr Ala Arg Gln Leu Asp Gln Gln
1               5                   10                  15

Asp Pro Ile Ser Arg Met Arg Glu Gln Phe His Ile Pro Lys Gln Asp
            20                  25                  30

Asn Gly Asp Asp Glu Ile Tyr Leu Cys Gly Asn Ser Leu Gly Leu Gln
        35                  40                  45

Pro Lys Arg Thr Gln Glu Tyr Leu Asn Tyr Glu Leu Ser Gln Trp Gln
    50                  55                  60

Lys Leu Gly Val Lys Gly His Phe Ser Gly Asp Phe Pro Trp Met Pro
65                  70                  75                  80

Tyr His Glu Phe Leu Thr Glu Glu Ser Ala Lys Leu Val Gly Ala Lys
                85                  90                  95

Asn Ser Glu Val Val Cys Met Asn Ser Leu Thr Ala Asn Leu His Phe
            100                 105                 110

Met Met Val Ser Phe Tyr Arg Pro Thr Ala Thr Arg Asn Lys Ile Leu
        115                 120                 125

Ile Glu Asp His Ala Phe Pro Ser Asp His Tyr Ala Val Glu Ser Gln
130                 135                 140

Val Arg Tyr His Gly Phe Asp Pro Asp Gln Ala Met Leu Leu Ala Lys
145                 150                 155                 160

Pro Arg Glu Gly Glu Glu Thr Leu Arg Thr Glu Asp Leu Leu Asn Leu
                165                 170                 175

Ile Glu Leu His Gly Glu Glu Ile Ala Leu Ile Met Leu Pro Gly Val
            180                 185                 190

Gln Tyr Tyr Thr Gly Gln Val Leu Asp Met Lys Ala Ile Thr Gln Ala
        195                 200                 205

Gly His Ala Lys Gly Cys Lys Val Gly Phe Asp Leu Ala His Ala Thr
210                 215                 220

Gly Asn Ile Pro Met His Leu His Asp Trp Asp Val Asp Phe Ala Ala
225                 230                 235                 240

Trp Cys Ser Tyr Lys Tyr Leu Asn Ser Gly Pro Gly Ser Val Ala Gly
                245                 250                 255

Cys Phe Val His Glu Lys His His Thr Asn Met Glu Leu Pro Arg Phe
            260                 265                 270

Ala Gly Trp Trp Gly His Asp Lys Asp Ser Arg Phe Lys Met Glu Asn
        275                 280                 285

His Phe Ile Pro Met Lys Ser Ala Glu Ala Trp Gln Leu Ser Asn Pro
290                 295                 300

Pro Ile Leu Ser Leu Ala Ala Ile Arg Ala Ser Leu Asp Thr Ile Lys
305                 310                 315                 320

Asp Ala Gly Gly Ile Gln Ala Leu Arg Asp Lys Ser Leu Lys Leu Ser
                325                 330                 335
```

Arg Tyr Leu Arg Asp Leu Leu Glu Gln Glu Leu Ala Asp Glu Ile Asn
            340                 345                 350

Ile Leu Thr Pro Ala Asp Glu Lys Ala Ser Gly Cys Gln Leu Ser Leu
        355                 360                 365

Thr Val Asn Leu His Gly Leu Asp Gly Lys Thr Val Phe Asp Arg Ile
    370                 375                 380

Glu Ala Ala Gly Val Thr Cys Asp Phe Arg His Pro Asn Val Ile Arg
385                 390                 395                 400

Val Ala Pro Val Pro Leu Tyr Asn Ser Phe Glu Asp Ala Tyr Arg Phe
                405                 410                 415

Val Thr Ile Leu Lys Asp Ser Leu Lys
            420                 425

<210> SEQ ID NO 30
<211> LENGTH: 425
<212> TYPE: PRT
<213> ORGANISM: Kangiella koreensis DSM 16069

<400> SEQUENCE: 30

Met Asn Asn Leu Phe Ser Leu Glu His Ala Gln Gln Leu Asp Gln Gln
1               5                   10                  15

Asp Pro Leu His His Met Arg Asp Gln Phe His Ile Pro Lys Gln Asp
            20                  25                  30

Asn Gly Asp Asp Glu Ile Tyr Leu Cys Gly Asn Ser Leu Gly Leu Gln
        35                  40                  45

Pro Lys Arg Thr Gln Glu Tyr Leu Asn Tyr Glu Leu Asn Gln Trp Gln
    50                  55                  60

Lys Leu Gly Val Lys Gly His Phe Ser Gly Asp Phe Pro Trp Met Pro
65                  70                  75                  80

Tyr His Glu Phe Leu Thr Glu Glu Ser Ala Lys Leu Val Gly Ala Lys
                85                  90                  95

Asn Thr Glu Val Val Cys Met Asn Ser Leu Thr Ala Asn Leu His Phe
            100                 105                 110

Met Met Val Ser Phe Tyr Arg Pro Ser Lys Thr Arg Asn Lys Ile Leu
        115                 120                 125

Ile Glu Asp His Ala Phe Pro Ser Asp His Tyr Ala Val Glu Ser Gln
    130                 135                 140

Ile Arg Phe His Gly Phe Asp Pro Asp Gln Ala Met Leu Leu Ala Lys
145                 150                 155                 160

Pro Arg Glu Gly Glu Glu Thr Leu Arg Thr Glu Asp Leu Leu Asn Leu
                165                 170                 175

Ile Glu Met His Gly Asp Glu Ile Ala Leu Ile Met Leu Pro Gly Val
            180                 185                 190

Gln Tyr Tyr Thr Gly Gln Val Leu Asp Met Lys Thr Ile Thr Glu Ala
        195                 200                 205

Gly His Ala Lys Gly Cys Met Val Gly Phe Asp Leu Ala His Ala Thr
    210                 215                 220

Gly Asn Ile Pro Met Asn Leu His Asp Trp Asn Val Asp Phe Ala Ala
225                 230                 235                 240

Trp Cys Thr Tyr Lys Tyr Leu Asn Ser Gly Pro Gly Ser Val Ala Gly
                245                 250                 255

Cys Phe Val His Glu Lys His His Ser Asn Leu Glu Leu Pro Arg Phe
            260                 265                 270

Ala Gly Trp Trp Gly His Asp Lys Glu Ser Arg Phe Arg Met Glu Asn
        275                 280                 285

-continued

Arg Phe Val Pro Met Gln Ser Ala Glu Ala Trp Gln Val Ser Asn Pro
          290                 295                 300

Pro Ile Leu Ser Leu Ala Ala Ile Arg Ala Ser Leu Asp Thr Val Lys
305                 310                 315                 320

Glu Ala Gly Gly Ile Asp Ala Leu Arg Glu Lys Ser Leu Lys Leu Thr
                325                 330                 335

Arg Tyr Leu Arg Asp Leu Leu Glu Gln Glu Leu Ser Glu Glu Ile Asn
            340                 345                 350

Ile Leu Thr Pro Ala Asp Asn Ser Ala Ser Gly Cys Gln Leu Ser Leu
        355                 360                 365

Thr Val Asn Leu His Val Leu Asp Gly Lys Thr Val Phe Asp Arg Ile
370                 375                 380

Glu Ala Ala Gly Val Thr Cys Asp Phe Arg His Pro Asn Val Ile Arg
385                 390                 395                 400

Val Ala Pro Val Pro Leu Tyr Asn Ser Phe Glu Asp Ala Tyr Arg Phe
                405                 410                 415

Val Ser Ile Leu Lys Asp Ser Leu Gln
            420                 425

<210> SEQ ID NO 31
<211> LENGTH: 421
<212> TYPE: PRT
<213> ORGANISM: Lacinutrix sp. 5H-3-7-4

<400> SEQUENCE: 31

Met Ser Asn Tyr Thr Leu Gly Arg Asp Phe Ala Gln Gln Leu Asp Lys
1               5                   10                  15

Glu Asp Gln Leu Ala His Tyr Arg Asn Gln Phe His Ile Pro Lys Asp
            20                  25                  30

Lys Asn Gly Asp Asp Leu Ile Tyr Leu Cys Gly Asn Ser Leu Gly Leu
        35                  40                  45

Gln Pro Lys Val Thr Lys Asp Tyr Ile Asn Gln Glu Leu Glu Asp Trp
    50                  55                  60

Ala Asn Leu Gly Val Glu Gly His Thr Glu Gly Lys Asn Pro Trp Leu
65                  70                  75                  80

Pro Tyr His Glu Phe Leu Thr Glu Ser Met Ala Lys Val Val Gly Ala
                85                  90                  95

Lys Pro Ile Glu Val Val Met Asn Thr Leu Thr Ala Asn Leu His
            100                 105                 110

Phe Met Met Val Ser Phe Tyr Lys Pro Thr Lys Lys Arg Tyr Lys Ile
        115                 120                 125

Leu Ile Glu Ala Asp Ala Phe Pro Ser Asp Lys Tyr Ala Val Glu Ser
130                 135                 140

Gln Leu Arg His His Gly Phe Asp Asp Lys Glu Gly Leu Val Leu Trp
145                 150                 155                 160

Lys Ala Arg Glu Gly Glu Glu Leu Ala Asn Tyr Glu Asp Leu Glu Ala
                165                 170                 175

Ile Leu Glu Ala Gln Gly Asp Glu Ile Ala Leu Ile Met Ile Gly Gly
            180                 185                 190

Val Asn Tyr Tyr Thr Gly Gln Phe Phe Asp Phe Lys Arg Ile Ala Ala
        195                 200                 205

Leu Gly His Lys Asn Gly Cys Met Val Gly Phe Asp Cys Ala His Gly
    210                 215                 220

Ala Gly Asn Val Asn Leu Asp Leu His Asn Ser Gly Ala Asp Phe Ala

```
                225                 230                 235                 240
        Val Trp Cys Thr Tyr Lys Tyr Met Asn Ala Gly Pro Gly Ser Leu Ser
                        245                 250                 255

Gly Cys Phe Val His Glu Arg His Ala His Asn Lys Asp Leu Asn Arg
                        260                 265                 270

Phe Thr Gly Trp Trp Ser His Asn Lys Glu Thr Arg Phe Asn Met Arg
                        275                 280                 285

Gly Glu Phe Asp Gln Leu Pro Gly Ala Glu Gly Trp Gln Leu Ser Asn
                        290                 295                 300

Pro Pro Ile Leu Ser Met Ala Ala Ile Lys Ala Ser Ala Asp Ile Phe
        305                 310                 315                 320

Ala Glu Val Gly Met Glu Lys Leu Thr Gln Lys Ser Lys Lys Leu Thr
                        325                 330                 335

Gly Tyr Phe Glu Phe Leu Leu Asn Glu Leu Asn Asn Ser Asp Ile Lys
                        340                 345                 350

Ile Ile Thr Pro Ser Asn Pro Asn Glu Arg Gly Cys Gln Leu Ser Ile
                        355                 360                 365

Gln Val Lys Asn Ala Asp Lys Ala Leu His His Lys Leu Thr Glu Ser
                        370                 375                 380

Gly Val Ile Ser Asp Trp Arg Glu Pro Asp Val Ile Arg Cys Ala Pro
        385                 390                 395                 400

Val Pro Leu Tyr Asn Ser Phe Glu Asp Val Tyr Asn Met Val Glu Arg
                        405                 410                 415

Leu Lys Ala Cys Leu
                        420

<210> SEQ ID NO 32
<211> LENGTH: 428
<212> TYPE: PRT
<213> ORGANISM: Cecembia lonarensis

<400> SEQUENCE: 32

Met Thr Thr Thr Asp Phe Glu Tyr Thr Glu Asp Phe Ala Lys Arg Met
1               5                   10                  15

Asp Asp Leu Asp Pro Phe Arg His Phe Arg Ser Met Phe His Phe Pro
                20                  25                  30

Tyr Val Asn Gly Lys Glu Ala Ile Tyr Phe Cys Gly Asn Ser Leu Gly
                35                  40                  45

Leu Gln Pro Lys Ser Val Arg Glu Tyr Leu Asp Arg Glu Leu Lys Asn
        50                  55                  60

Trp Glu Leu Met Ala Val Asp Gly His Phe His Gly Glu Asp Ala Trp
65                  70                  75                  80

Tyr His Val Arg Lys Lys Ser Lys Pro Ala Leu Ala Glu Ile Val Gly
                85                  90                  95

Ala His Glu His Glu Val Val Ala Met Asn Asn Leu Ser Ser Asn Leu
                100                 105                 110

His Phe Leu Met Val Ser Phe Tyr Arg Pro Thr Lys Glu Arg Tyr Lys
                115                 120                 125

Ile Ile Thr Glu Ala Gly Ala Phe Pro Ser Asp Met Tyr Met Leu Glu
                130                 135                 140

Thr Gln Val Lys Phe His Gly Phe Asp Pro Ala Asp Ala Ile Ile Glu
145                 150                 155                 160

Val Ala Pro Arg Pro Gly Glu Tyr Thr Ile Arg Thr Glu Asp Ile Leu
                165                 170                 175
```

```
Ala Ala Ile Glu Asp Asn Gln Asp Glu Leu Ala Leu Val Met Met Ala
            180                 185                 190

Gly Leu Gln Tyr Tyr Thr Gly Gln Val Phe Asp Met Glu Ala Ile Thr
        195                 200                 205

Lys Ala Gly His Gly Ile Gly Val Pro Val Gly Phe Asp Leu Ala His
    210                 215                 220

Ala Ala Gly Asn Ile Pro Leu Arg Leu His Asp Trp Gly Val Asp Phe
225                 230                 235                 240

Ala Ala Trp Cys Ser Tyr Lys Tyr Leu Asn Ser Gly Pro Gly Asn Ile
                245                 250                 255

Ser Gly Ile Phe Val His Glu Arg His Ala Asp Asn Thr Glu Leu Pro
            260                 265                 270

Arg Phe Gly Gly Trp Trp Gly His Asp Glu Ala Ile Arg Phe Lys Met
        275                 280                 285

Glu Lys Gly Phe Glu Pro Met Tyr Gly Ala Asp Gly Trp Gln Leu Ala
    290                 295                 300

Asn Ser Asn Val Leu Ala Leu Ala Val His Gln Ala Ser Leu Asp Ile
305                 310                 315                 320

Phe Gln Glu Ala Gly Met Glu Arg Leu Arg Thr Lys Ser Glu Leu Leu
                325                 330                 335

Thr Gly Tyr Leu Glu Phe Leu Ile Arg Lys Val Gly Phe Ala Asn Gly
            340                 345                 350

Val Leu Glu Ile Ile Thr Pro Asn Asn Pro Lys Glu Arg Gly Cys Gln
        355                 360                 365

Leu Ser Leu Leu Val His Lys Gly Gly Lys Leu Val Phe Asp His Leu
    370                 375                 380

Tyr Ala Asn Gly Val Val Gly Asp Trp Arg His Pro Asn Val Ile Arg
385                 390                 395                 400

Val Ala Pro Thr Pro Leu Tyr Asn Ser Phe Thr Asp Val Phe Arg Phe
                405                 410                 415

Ala Lys Ile Leu Glu His Ser Leu Gln Lys Phe Ala
            420                 425

<210> SEQ ID NO 33
<211> LENGTH: 429
<212> TYPE: PRT
<213> ORGANISM: Mucilaginibacter paludis

<400> SEQUENCE: 33

Met Asn Tyr Gln Asn Thr Leu Ala Phe Ala Arg Glu Leu Asp Glu Gln
1               5                   10                  15

Asp Asn Leu Ala Gly Phe Arg Asn Glu Phe Ile Ile Pro Gln His His
                20                  25                  30

Gly Arg Asp Met Ile Tyr Leu Cys Gly Asn Ser Leu Gly Leu Gln Pro
            35                  40                  45

Lys Ala Thr Ala Gly Val Ile Ala Glu Gln Leu Ser Asn Trp Gly Ser
    50                  55                  60

Leu Ala Val Glu Gly Trp Phe Glu Gly Asp Ser Pro Trp Met His Tyr
65                  70                  75                  80

His Lys Lys Leu Thr Glu Pro Leu Ala Ala Ile Val Gly Ala Leu Asn
                85                  90                  95

Thr Glu Val Val Ala Met Asn Thr Leu Thr Val Asn Leu His Phe Leu
            100                 105                 110

Leu Val Ser Phe Tyr Arg Pro Thr Ala Lys Lys Tyr Lys Ile Leu Met
        115                 120                 125
```

-continued

Glu Gly Gly Ala Phe Pro Ser Asp Gln Tyr Ala Ile Glu Ser Gln Val
         130                 135                 140

His Phe His Gly Tyr Gln Pro Asp Asp Ala Ile Ile Glu Val Phe Pro
145                 150                 155                 160

Arg Ala Gly Glu Asp Thr Leu Arg Thr Glu Asp Ile Ile Arg Thr Ile
                165                 170                 175

His Asp His Ala Asp Asp Leu Ala Leu Val Leu Phe Gly Gly Ile Asn
         180                 185                 190

Tyr Tyr Thr Gly Gln Phe Tyr Asp Leu Glu Gln Ile Thr Gln Ala Ala
         195                 200                 205

His Gln Val Gly Ala Tyr Ala Gly Phe Asp Leu Ala His Ala Ala Gly
         210                 215                 220

Asn Val Pro Leu Gln Leu His His Trp Gln Val Asp Phe Ala Cys Trp
225                 230                 235                 240

Cys Ser Tyr Lys Tyr Met Asn Ser Ser Pro Gly Gly Ile Ser Gly Ala
                245                 250                 255

Phe Ile His Glu Lys His Phe Gly Asn Lys Glu Leu Asn Arg Phe Ala
         260                 265                 270

Gly Trp Trp Gly Tyr Arg Glu Asp Lys Arg Phe Glu Met Lys Pro Gly
         275                 280                 285

Phe Lys Pro Gln Glu Gly Ala Glu Gly Trp Gln Val Ser Cys Ser Pro
290                 295                 300

Leu Leu Leu Met Ala Ala His Lys Ala Ser Leu Asn Val Phe Glu Lys
305                 310                 315                 320

Ala Gly Tyr Ile Glu Pro Leu Arg Lys Ser Lys Leu Leu Thr Gly
                325                 330                 335

Tyr Leu Glu Tyr Leu Ile Glu Gly Ile Asn Thr Ala His Gln Lys Gln
                340                 345                 350

Leu Phe Lys Ile Ile Thr Pro Lys Asn Glu Asn Glu Arg Gly Cys Gln
         355                 360                 365

Leu Ser Ile Val Cys Asp Asn Gly Lys Ala Ile Phe Asp Gln Leu Val
370                 375                 380

Glu Gly Gly Val Leu Gly Asp Trp Arg Glu Pro Asp Val Ile Arg Leu
385                 390                 395                 400

Ser Pro Ile Pro Leu Tyr Asn Ser Phe Glu Asp Val Tyr Leu Ala Gly
                405                 410                 415

Lys Leu Leu Ala Gly Ser Val Thr Gln Phe Phe Ala Glu
         420                 425

<210> SEQ ID NO 34
<211> LENGTH: 425
<212> TYPE: PRT
<213> ORGANISM: Myroides odoratimimus

<400> SEQUENCE: 34

Met Ser Phe Glu Asn Thr Leu Ala Tyr Ala Lys Ser Leu Asp Glu Lys
1               5                   10                  15

Asp Pro Leu Ala Lys Tyr Arg Asp Glu Phe Asn Phe Pro Glu Val Asn
                20                  25                  30

Gly Lys Gln Val Ile Tyr Phe Thr Gly Asn Ser Leu Gly Leu Gln Pro
         35                  40                  45

Lys Arg Ala Val Glu Tyr Val Asn Glu Val Met Asn Asp Trp Gly Ala
50                  55                  60

Leu Ala Val Glu Gly His Phe Tyr Ala Glu Lys Pro Trp Trp Asp Tyr

```
            65                  70                  75                  80
His Glu Arg Leu Ser Glu Pro Leu Ser Arg Ile Val Gly Ala Lys Ser
                85                  90                  95

Ser Glu Ile Thr Val Met Asn Thr Leu Thr Val Asn Leu His Leu Leu
            100                 105                 110

Met Thr Thr Phe Tyr Arg Pro Thr Ala Ser Lys Tyr Lys Ile Ile Cys
            115                 120                 125

Glu Glu Lys Ala Phe Pro Ser Asp Gln Tyr Leu Ile Gln Ser Gln Val
    130                 135                 140

Arg Leu His Gly Leu Asp Pro Lys Glu Ala Ile Ile Glu Leu Lys Lys
145                 150                 155                 160

Arg Pro Gly Glu His Asn Phe Arg Leu Glu Asp Ile Leu Glu Lys Ile
                165                 170                 175

Asp Glu Val Gly Glu Val Ala Leu Val Leu Ile Gly Gly Leu Asn
            180                 185                 190

Tyr Tyr Thr Gly Gln Val Phe Asp Ile Gln Thr Ile Thr Ala His Ala
            195                 200                 205

His Gln Tyr Gly Ala Lys Val Gly Trp Asp Leu Ala His Ala Ala Gly
    210                 215                 220

Asn Ile Glu Leu Lys Leu His Glu Trp Asn Val Asp Phe Ala Ala Trp
225                 230                 235                 240

Cys Ser Tyr Lys Tyr Met Asn Ala Gly Pro Gly Ser Ala Ser Gly Cys
                245                 250                 255

Phe Ile His Glu Arg Tyr His Thr Asp Lys Asp Leu Val Arg Leu Ala
            260                 265                 270

Gly Trp Trp Gly His Asn Lys Glu Arg Arg Phe Leu Met Glu Lys Lys
            275                 280                 285

Phe Asp Ala Val Glu Ser Ala His Gly Trp Gln Ile Ser Asn Pro Ser
    290                 295                 300

Ile Leu Ser Leu Ala Pro Tyr Leu Ala Ser Ile Glu Met Phe Asp Glu
305                 310                 315                 320

Val Gly Met Glu Ala Leu Ile Thr Lys Gln Arg Lys Ile Thr Ala Tyr
                325                 330                 335

Leu Glu Phe Val Met Glu Asp Val Ala Lys Ala Val Asn Ala Asn Tyr
            340                 345                 350

Glu Leu Ile Thr Pro Lys Glu Ser Glu Arg Gly Ser Gln Leu Ser
            355                 360                 365

Val Phe Leu His Gly Lys Gly Lys Asp Leu Phe Ser Tyr Leu Met Asn
370                 375                 380

Glu Gly Val Ile Val Asp Trp Arg Glu Pro Asn Val Val Arg Leu Ala
385                 390                 395                 400

Pro Val Pro Phe Tyr Thr Ser Tyr Glu Asp Ile Tyr Arg Phe Gly Glu
                405                 410                 415

Ile Leu Lys Lys Ala Asp Ser Leu Phe
                420                 425

<210> SEQ ID NO 35
<211> LENGTH: 426
<212> TYPE: PRT
<213> ORGANISM: Myxococcus fulvus HW-1

<400> SEQUENCE: 35

Met Thr Thr Pro His Ala Phe Glu Asp Thr Glu Ala Phe Ala His Thr
1               5                   10                  15
```

```
Leu Asp Ala Glu Asp Ala Leu Arg Gly Tyr Arg Asp Ala Phe His Phe
             20                  25                  30

Pro Pro Gly Pro Asp Gly Lys Pro Val Val Tyr Leu Ala Gly Asn Ser
         35                  40                  45

Leu Gly Leu Gln Pro Arg Asn Ala Ala Arg Tyr Ile Gln Glu Glu Leu
     50                  55                  60

Glu Asp Trp Ala Arg Leu Gly Val Glu Gly His His Gly Arg His
65                  70                  75                  80

Pro Trp Leu His Tyr His Glu Leu Val Thr Glu Gln Ala Ala Arg Leu
                 85                  90                  95

Val Gly Ala Lys Pro Leu Glu Val Val Met Asn Thr Leu Ser Val
             100                 105                 110

Asn Leu His Leu Met Met Val Ser Phe Tyr Arg Pro Thr Lys Gln Arg
         115                 120                 125

Phe Lys Ile Leu Val Glu Ala Gly Ala Phe Pro Ser Asp Gln Tyr Ala
130                 135                 140

Val Ala Ser Gln Val Arg Phe His Gly His Asp Ala Arg Glu Ala Val
145                 150                 155                 160

Leu Glu Leu Lys Pro Arg Glu Gly Glu Thr Leu Arg Thr Glu Asp
                 165                 170                 175

Ile Leu Asp Thr Leu Glu Arg His Gly His Glu Val Ala Leu Val Met
             180                 185                 190

Leu Gly Ser Val Asn Tyr Leu Thr Gly Gln Ala Phe Asp Leu Ala Ala
         195                 200                 205

Ile Thr Lys Ala Ala His Ala Lys Gly Cys Leu Val Gly Phe Asp Leu
     210                 215                 220

Ala His Gly Ala Gly Asn Leu Lys Leu Ser Leu His Asp Asp Gly Pro
225                 230                 235                 240

Asp Phe Ala Val Trp Cys Ser Tyr Lys Tyr Leu Asn Ala Gly Pro Gly
                 245                 250                 255

Ala Leu Gly Gly Val Phe Val His Glu Arg His Ala His Thr Lys Asp
             260                 265                 270

Leu Pro Arg Phe Glu Gly Trp Trp Gly His Asp Lys Gln Thr Arg Phe
         275                 280                 285

Gln Met Gly Pro Thr Phe His Ala Leu Pro Gly Ala Glu Gly Trp Gln
290                 295                 300

Leu Ser Asn Pro Pro Ile Phe Gln Leu Ala Ala Leu Arg Ala Ser Leu
305                 310                 315                 320

Glu Leu Phe Asp Gln Ala Gly Met Ala Ala Leu Arg Ala Lys Ser Glu
                 325                 330                 335

Arg Leu Thr Gly Tyr Leu Glu Phe Leu Leu Asp Lys Leu Pro Gln Gly
             340                 345                 350

Phe Val Arg Ile Thr Thr Pro Arg Asp Val Lys Gln Arg Gly Ala Gln
         355                 360                 365

Leu Ser Leu Arg Phe Arg Gly Glu Pro Gln Gly Leu Leu Lys Arg Met
370                 375                 380

Gly Asp Ala Gly Ile Val Cys Asp Phe Arg Lys Pro Asp Ile Ile Arg
385                 390                 395                 400

Ala Ala Pro Ala Pro Leu Tyr Asn Ser Phe Thr Asp Val Tyr Arg Phe
                 405                 410                 415

Val Lys Ala Leu Glu Gly Tyr Ala Arg Glu
             420                 425
```

<210> SEQ ID NO 36
<211> LENGTH: 425
<212> TYPE: PRT
<213> ORGANISM: Myxococcus stipitatus DSM 14675

<400> SEQUENCE: 36

```
Met Thr Thr His Ser Phe Glu Asp Thr Glu Asp Phe Ala Arg Arg Ala
1               5                   10                  15

Asp Glu Ala Asp Ala Leu Arg Ser Phe Arg Asp Ala Phe His Phe Pro
            20                  25                  30

Pro Gly Thr Asp Gly Lys Pro Leu Val Tyr Leu Ala Gly Asn Ser Leu
        35                  40                  45

Gly Leu Gln Pro Lys Asn Ala Ala Arg Tyr Val Gln Glu Glu Leu Glu
    50                  55                  60

Asp Trp Ala Arg Phe Gly Val Glu Gly His His Gly Arg His Pro
65                  70                  75                  80

Trp Leu His Tyr His Glu Leu Val Thr Glu Gln Ala Ala Arg Leu Val
                85                  90                  95

Gly Ala Lys Pro Gln Glu Val Val Met Asn Thr Leu Thr Val Asn
                100                 105                 110

Leu His Leu Met Met Val Ser Phe Tyr Arg Pro Thr Lys Thr Arg Phe
            115                 120                 125

Lys Ile Leu Val Glu Gly Gly Ala Phe Pro Ser Asp Gln Tyr Ala Val
    130                 135                 140

Ala Ser Gln Ala Arg Phe His Gly Tyr Asp Pro Arg Glu Ala Ile Leu
145                 150                 155                 160

Glu Leu Lys Pro Arg Pro Gly Glu Glu Thr Leu Arg Thr Glu Asp Ile
                165                 170                 175

Leu Ala Thr Leu Asp Gln His Gly His Glu Val Ala Leu Val Met Leu
            180                 185                 190

Gly Ser Val Asn Tyr Leu Thr Gly Gln Ala Phe Asp Ile Pro Ala Ile
        195                 200                 205

Thr Lys Thr Ala His Ala Lys Gly Cys Phe Val Gly Phe Asp Leu Ala
210                 215                 220

His Gly Ala Gly Asn Leu Lys Leu Ala Leu His Asp Asp Gly Pro Asp
225                 230                 235                 240

Phe Ala Val Trp Cys Ser Tyr Lys Tyr Leu Asn Gly Gly Pro Gly Ala
                245                 250                 255

Leu Ala Gly Val Phe Val His Glu Arg His Ala Arg Ser Lys Asp Ile
            260                 265                 270

Pro Arg Phe Glu Gly Trp Trp Gly His Asp Lys Ala Thr Arg Phe Gln
        275                 280                 285

Met Gly Pro Thr Phe Asp Pro Leu Pro Gly Ala Glu Gly Trp Gln Leu
    290                 295                 300

Ser Asn Pro Pro Ile Leu Gln Leu Ala Ala Leu Arg Ala Ser Phe Glu
305                 310                 315                 320

Leu Phe Asp Gln Ala Gly Met Glu Ala Leu Arg Ala Lys Ser Glu Lys
                325                 330                 335

Leu Thr Gly Tyr Leu Glu Phe Leu Leu Glu Lys Leu Pro Pro Gly Phe
            340                 345                 350

Val Arg Ile Ile Thr Pro Arg Asp Val Lys Gln Arg Gly Ala Gln Leu
        355                 360                 365

Ser Leu Arg Phe Lys Gly Glu Ala Gln Gly Met Leu Lys Arg Leu Ser
    370                 375                 380
```

-continued

Asp Ala Gly Ile Ile Cys Asp Phe Arg Lys Pro Asp Ile Ile Arg Ala
385                 390                 395                 400

Ala Pro Ala Pro Leu Tyr Cys Ser Phe Thr Asp Val Tyr Arg Phe Val
            405                 410                 415

Arg Thr Leu Glu Ala His Ala Arg Asp
            420                 425

<210> SEQ ID NO 37
<211> LENGTH: 426
<212> TYPE: PRT
<213> ORGANISM: Myxococcus xanthus DK 1622

<400> SEQUENCE: 37

Met Thr Thr Pro Tyr Leu Phe Glu Asp Ser Glu Ser Phe Ala Arg Lys
1               5                   10                  15

Leu Asp Ala Glu Asp Ala Leu Arg Gly Tyr Arg Asp Ala Phe His Phe
            20                  25                  30

Pro Pro Gly Pro Asp Gly Lys Pro Val Val Tyr Leu Ala Gly Asn Ser
            35                  40                  45

Leu Gly Leu Gln Pro Arg Asn Ala Ala Arg Tyr Ile Gln Glu Glu Leu
50                  55                  60

Glu Asp Trp Ala Arg Leu Gly Val Glu Gly His His Gly Arg His
65                  70                  75                  80

Pro Trp Leu His Tyr His Glu Leu Val Thr Glu His Ala Ala Arg Leu
            85                  90                  95

Val Gly Ala Lys Pro Leu Glu Val Val Met Asn Thr Leu Ser Val
            100                 105                 110

Asn Leu His Leu Met Met Val Ser Phe Tyr Arg Pro Thr Lys Gln Arg
            115                 120                 125

Phe Lys Ile Leu Val Glu Ala Gly Ala Phe Pro Ser Asp Gln Tyr Ala
130                 135                 140

Val Ala Ser Gln Val Arg Phe His Gly Tyr Asp Ala Arg Glu Ala Val
145                 150                 155                 160

Leu Glu Leu Lys Pro Arg Glu Gly Glu Thr Leu Arg Thr Glu Asp
                165                 170                 175

Ile Leu Glu Thr Ile Glu Arg His Gly His Glu Val Ala Leu Val Met
            180                 185                 190

Leu Gly Ser Val Asn Tyr Leu Thr Gly Gln Ala Phe Asp Leu Ala Ala
            195                 200                 205

Ile Thr Lys Ala Ala His Ala Lys Gly Cys Phe Val Gly Phe Asp Leu
210                 215                 220

Ala His Gly Ala Gly Asn Leu Arg Leu Ser Leu His Asp Asp Gly Pro
225                 230                 235                 240

Asp Phe Ala Val Trp Cys Ser Tyr Lys Tyr Leu Asn Ala Gly Pro Gly
                245                 250                 255

Ala Leu Gly Gly Val Phe Val His Glu Arg His Ala His Thr Lys Asp
            260                 265                 270

Leu Pro Arg Phe Glu Gly Trp Trp Gly His Asp Lys Gln Thr Arg Phe
            275                 280                 285

Gln Met Gly Pro Thr Phe Ser Ala Leu Pro Gly Ala Glu Gly Trp Gln
290                 295                 300

Leu Ser Asn Pro Pro Ile Phe Gln Leu Ala Ala Leu Arg Ala Ser Leu
305                 310                 315                 320

Glu Leu Phe Asp Gln Ala Gly Met Ala Ala Leu Arg Ala Lys Ser Glu
            325                 330                 335

```
Arg Leu Thr Gly Tyr Leu Glu Phe Leu Leu Asp Arg Leu Pro Glu Gly
            340                 345                 350

Phe Val Arg Ile Thr Thr Pro Arg Asp Val Lys Gln Arg Gly Ala Gln
            355                 360                 365

Leu Ser Leu Arg Phe Arg Gly Glu Pro Gln Gly Leu Leu Lys Arg Leu
370                 375                 380

Gly Asp Ala Gly Ile Ile Cys Asp Phe Arg Lys Pro Asp Ile Arg
385                 390                 395                 400

Ala Ala Pro Ala Pro Leu Tyr Asn Ser Phe Thr Asp Val Tyr Arg Phe
                405                 410                 415

Val Lys Thr Leu Glu Gly His Ala Arg Glu
            420                 425

<210> SEQ ID NO 38
<211> LENGTH: 428
<212> TYPE: PRT
<213> ORGANISM: Nafulsella turpanensis

<400> SEQUENCE: 38

Met Ile Asn Gln Tyr Gln Ser Asn Gln Ala Tyr Ala Arg Glu Gln Asp
1               5                   10                  15

Ala Arg Asp Pro Leu Arg Gln Phe Arg Glu Gln Phe Ile Ile Pro Pro
            20                  25                  30

Ala Lys Ser Gly Gly Glu Ala Ile Tyr Phe Cys Gly Asn Ser Leu Gly
        35                  40                  45

Leu Gln Pro Lys Asn Thr Arg Ser Tyr Leu Asp Arg Glu Leu Glu Lys
50                  55                  60

Trp Ala Thr Tyr Ala Val Asp Gly His Phe His Ala Pro Glu Pro Trp
65                  70                  75                  80

Leu His Tyr His Arg Leu Leu Lys Glu Pro Leu Ala Arg Ile Val Gly
                85                  90                  95

Ala Lys Pro Glu Glu Val Val Met Asn Asn Leu Ser Ser Asn Leu
            100                 105                 110

His Phe Leu Met Val Ser Phe Tyr Gln Pro Thr Thr Lys Arg Tyr Lys
        115                 120                 125

Val Leu Met Glu Gly Gly Ala Phe Pro Ser Asp Gln Tyr Ala Val Glu
130                 135                 140

Ser Gln Val Lys Phe Arg Gly Tyr Thr Pro Glu Ala Ile Val Glu
145                 150                 155                 160

Val Phe Pro Arg Glu Gly Glu Gln Thr Leu Arg Thr Glu Asp Ile Leu
                165                 170                 175

Ala Ala Ile Glu Gln His Gln Asp Glu Leu Ala Leu Val Leu Phe Ala
            180                 185                 190

Gly Leu Gln Tyr Tyr Thr Gly Gln Val Phe Asp Met Ala Ala Ile Thr
        195                 200                 205

Lys Ala Gly Gln Ala Ala Gly Ala Lys Val Gly Phe Asp Leu Ala His
210                 215                 220

Ala Ala Gly Asn Val Pro Leu Gln Leu His Asp Trp Gly Val Asp Phe
225                 230                 235                 240

Ala Ala Trp Cys Ser Tyr Lys Tyr Leu Asn Ser Gly Pro Gly Ser Asn
                245                 250                 255

Ser Gly Ile Phe Val His Glu Arg Tyr Ala Asn Gln Ala Glu Leu Pro
            260                 265                 270

Arg Phe Ala Gly Trp Trp Gly His Asp Glu Lys Glu Arg Phe Leu Met
```

```
            275                 280                 285
Gln Lys Gly Phe Lys Pro Met Tyr Gly Ala Asp Gly Trp Gln Leu Ser
        290                 295                 300
Asn Gly Asn Ile Leu Pro Leu Ala Ala Gln Arg Ala Ser Leu Glu Ile
305                 310                 315                 320
Phe Glu Gln Ala Gly Met Asp Asn Leu Arg Gln Lys Ser Ile Gln Leu
                325                 330                 335
Thr Gly Tyr Leu Glu Tyr Leu Ile Arg Glu Val Ser Ser Lys Ala
            340                 345                 350
Asn Arg Leu Gln Ile Ile Thr Pro Ser Gln Pro Glu Glu Arg Gly Cys
                355                 360                 365
Gln Leu Ser Leu Phe Val Glu Lys Asn Gly Lys Gln Leu Phe Glu Gln
            370                 375                 380
Ile Ser Gln Ala Gly Val Val Gly Asp Trp Arg Glu Pro Asn Val Ile
385                 390                 395                 400
Arg Val Ala Pro Thr Pro Leu Tyr Asn Thr Phe Thr Asp Val Phe Gln
                405                 410                 415
Phe Ala Gln Leu Leu Lys Lys Ala Ile Lys Glu Gln
            420                 425

<210> SEQ ID NO 39
<211> LENGTH: 428
<212> TYPE: PRT
<213> ORGANISM: Niastella koreensis GR20-10

<400> SEQUENCE: 39

Met Ile Phe Glu Asn Ser His Ser Phe Ala Tyr Val Leu Asp Glu Gln
1               5                   10                  15
Asp Glu Leu Arg Ser Phe Arg Glu Gln Phe Ile Met Pro Val Ile Asp
            20                  25                  30
Gly Lys Gln Gln Ile Tyr Phe Leu Gly Asn Ser Leu Gly Leu Gln Pro
        35                  40                  45
Lys Arg Thr Asn Asp Tyr Leu Gln Gln Val Leu Asn Lys Trp Ala Asn
50                  55                  60
Tyr Gly Val Glu Gly Phe Phe Met Gly Glu Gln Pro Trp Leu Gln Tyr
65                  70                  75                  80
His Asp His Leu Thr Lys Pro Leu Ser Thr Ile Val Gly Ala Leu Pro
                85                  90                  95
His Glu Val Val Ala Met Asn Gln Leu Thr Val Asn Leu His Leu Leu
            100                 105                 110
Leu Val Ser Phe Tyr Asn Pro His Gly Lys Arg Asn Lys Ile Ile Cys
        115                 120                 125
Glu Ala Lys Ala Phe Pro Ser Asp Gln Tyr Met Leu Glu Thr His Val
130                 135                 140
Lys Tyr Cys Gly Phe Asn Pro Asp Asp Val Ile Val Glu Val Gly Pro
145                 150                 155                 160
Arg Lys Gly Glu His Thr Ile Arg His Glu Asp Ile Leu Gln Ala Ile
                165                 170                 175
Gln Gln His Lys Asp Glu Leu Ala Leu Val Leu Trp Gly Gly Met Asn
            180                 185                 190
Tyr Tyr Thr Gly Gln Leu Phe Asp Met Ala Ala Ile Thr Lys Ala Ala
        195                 200                 205
Gln Ala Val Gly Ala Lys Val Gly Phe Asp Leu Ala His Ala Ala Gly
    210                 215                 220
```

Asn Val Pro Leu Gln Leu His Asn Trp Asn Val Asp Phe Ala Ala Trp
225                 230                 235                 240

Cys Ser Tyr Lys Tyr Met Asn Ser Gly Pro Gly Gly Ile Gly Gly Ala
            245                 250                 255

Tyr Ile His Glu Arg Tyr His Asn Asp Thr Ser Leu Pro Arg Phe Ala
        260                 265                 270

Gly Trp Trp Gly Tyr Asp Lys Ala Thr Arg Phe Leu Met Gln Lys Gly
            275                 280                 285

Phe Asn Ala Thr Arg Ser Ala Glu Gly Trp Gln Leu Ser Thr Pro Ser
290                 295                 300

Pro Leu Leu Tyr Ala Ala His Arg Ala Ala Leu Asp Leu Phe Met Glu
305                 310                 315                 320

Ala Gly Phe Asn Arg Leu Gln Asn Lys Arg Gln Leu Leu Asn Lys Trp
            325                 330                 335

Leu Trp Phe Leu Leu Asp Asp Leu Asn Asn Ala Gln Thr Glu Pro Val
            340                 345                 350

Val Glu Phe Ile Thr Pro Arg Asn Glu Ala Glu Arg Gly Cys Gln Val
            355                 360                 365

Ser Met Leu Met Leu Gln Gln Gly Lys Gln Val Phe Asp Glu Leu Ala
370                 375                 380

Arg Ala Gly Val Ile Val Asp Trp Arg Glu Pro Asn Val Ile Arg Leu
385                 390                 395                 400

Ala Pro Val Pro Leu Tyr Asn Ser Phe Glu Val Trp Gln Phe Thr
                405                 410                 415

Asn Ile Leu Arg Gln Ile Leu Gln Leu Gln His Ala
            420                 425

<210> SEQ ID NO 40
<211> LENGTH: 420
<212> TYPE: PRT
<213> ORGANISM: Nonlabens dokdonensis DSW-6

<400> SEQUENCE: 40

Met Asn Phe Lys Thr Asp His Asn Phe Ala Ile Glu Leu Asn Lys Ser
1               5                   10                  15

Asp Ser Leu Ser Arg Phe Arg Glu Ser Phe His Ile Pro Lys His Thr
            20                  25                  30

Asp Gly Thr Asp Ser Ile Tyr Leu Cys Gly Asn Ser Leu Gly Leu Gln
        35                  40                  45

Pro Arg Gln Thr Lys Thr Phe Leu Asn Gln Glu Leu Asp Asp Trp Ala
    50                  55                  60

Arg Leu Gly Val Glu Gly His Phe His Ala Ala His Pro Trp Met Pro
65                  70                  75                  80

Tyr His Glu Phe Leu Thr Glu Thr Thr Ala Gln Ile Val Gly Ala Lys
                85                  90                  95

Pro His Glu Val Val Ile Met Asn Thr Leu Thr Thr Asn Leu His Leu
            100                 105                 110

Met Met Val Ser Phe Tyr Gln Pro Lys Gly Lys Arg Thr Lys Ile Ile
        115                 120                 125

Ile Glu Ala Asp Ala Phe Pro Ser Asp Arg Tyr Ala Val Ala Ser Gln
    130                 135                 140

Val Lys Phe His Gly His Asp Asp Lys Glu Asn Ile Ile Glu Trp Ser
145                 150                 155                 160

Pro Arg Ala Gly Glu His Thr Pro Arg Ile Glu Asp Leu Glu Asn Leu
                165                 170                 175

Leu Lys Glu Gln Gly Asp Glu Ile Ala Leu Ile Met Val Gly Ala Val
            180                 185                 190

Asn Tyr Tyr Thr Gly Gln Phe Phe Asp Leu Lys Lys Ile Thr Glu Leu
            195                 200                 205

Gly His Ala Ala Gly Ala Met Val Gly Phe Asp Cys Ala His Gly Ala
            210                 215                 220

Gly Asn Val Asp Leu Gln Leu His Asn Ser Gly Ala Asp Phe Ala Val
225                 230                 235                 240

Trp Cys Thr Tyr Lys Tyr Met Asn Ser Gly Pro Gly Ser Leu Gly Gly
                245                 250                 255

Cys Phe Val His Glu Arg His Ala Ser Asn Ser Asp Leu Pro Arg Phe
            260                 265                 270

Thr Gly Trp Trp Gly His Asn Lys Asp Thr Arg Phe Lys Met Arg Asp
            275                 280                 285

Asp Phe Glu Pro Met His Gly Ala Glu Gly Trp Gln Leu Ser Asn Pro
            290                 295                 300

Pro Ile Leu Ser Met Val Ala Ile Arg Ala Ser Leu Asp Leu Phe Ala
305                 310                 315                 320

Gln Ala Gly Phe Glu Asn Leu Arg Gln Lys Ser Ile Gln Leu Thr Asn
                325                 330                 335

Tyr Leu Glu Tyr Leu Leu Ser Asn Leu Glu Gly Asp Arg Ile Ser Ile
            340                 345                 350

Ile Thr Pro Glu Asn Pro Lys Asp Arg Gly Cys Gln Leu Ser Leu Ala
            355                 360                 365

Val Lys Asn Ala Asp Lys Ser Leu Phe Asp Ala Ile Thr Glu Lys Gly
            370                 375                 380

Val Ile Ala Asp Trp Arg Glu Pro Asp Val Ile Arg Ile Ala Pro Val
385                 390                 395                 400

Pro Leu Tyr Asn Asn Tyr Glu Asp Cys Trp Arg Phe Val Asp Val Leu
                405                 410                 415

Lys Ser Glu Leu
            420

<210> SEQ ID NO 41
<211> LENGTH: 431
<212> TYPE: PRT
<213> ORGANISM: Pedobacter agri

<400> SEQUENCE: 41

Met Lys Leu Glu Asn Thr Leu Ala Phe Ala Lys Glu Gln Asp Glu Lys
1               5                   10                  15

Asp Glu Leu Lys His Phe Arg Asp Gln Phe Leu Phe Pro Lys Tyr Gln
            20                  25                  30

Asp Lys Phe Phe Ile Tyr Leu Cys Gly Asn Ser Leu Gly Leu Gln Pro
        35                  40                  45

Lys Val Ala Lys Glu Val Ile Asn Ser Gln Leu Asp Asn Trp Ala Asn
    50                  55                  60

Leu Ala Val Glu Gly Trp Phe Asp Gly Glu Pro Trp Met Tyr Tyr
65                  70                  75                  80

His Lys Glu Leu Lys Lys Leu Met Ala Pro Ile Val Gly Ala Leu Pro
                85                  90                  95

Ser Glu Val Cys Pro Met Asn Thr Leu Thr Val Asn Leu His Leu Leu
            100                 105                 110

Met Ile Ser Phe Tyr Gln Pro Gln Gly Lys Arg Phe Lys Ile Ile Met

-continued

```
                115                 120                 125
Glu Gly Gly Ala Phe Pro Ser Asp Gln Tyr Ala Ile Glu Ser Gln Val
        130                 135                 140

Arg Phe His Gly Phe Asp Pro Ser Asp Ala Ile Ile Glu Val Phe Pro
145                 150                 155                 160

Arg Glu Gly Glu Glu Ile Leu Arg Thr Glu Asp Ile Val Ala Lys Ile
                165                 170                 175

Lys Glu His Gly Asp Glu Ile Ala Leu Leu Phe Gly Gly Ile Asn
        180                 185                 190

Tyr Tyr Thr Gly Gln Trp Tyr Asp Met Glu Asn Ile Thr Lys Ala Gly
                195                 200                 205

His Ser Ile Gly Ala Met Val Gly Trp Asp Leu Ala His Ala Ala Gly
        210                 215                 220

Asn Val Pro Val Lys Leu His Asp Trp Asn Val Asp Phe Ala Cys Trp
225                 230                 235                 240

Cys Ser Tyr Lys Tyr Gln Asn Ala Gly Pro Gly Gly Ile Ser Gly Ile
                245                 250                 255

Phe Val His Glu Lys His Phe Glu Asn Lys Ala Leu Asn Arg Phe Ala
        260                 265                 270

Gly Trp Trp Gly Tyr Gln Glu Asn Lys Arg Phe Lys Met Glu Lys Gly
                275                 280                 285

Phe Val Pro Glu Ala Gly Ala Asp Gly Trp Gln Val Ser Cys Thr Gln
        290                 295                 300

Val Met Pro Met Ala Leu Tyr His Ala Ser Leu Gln Ile Phe Lys Glu
305                 310                 315                 320

Ala Gly Phe Leu Asn Thr Leu Arg Asn Lys Ser Ile Ser Leu Thr Ser
                325                 330                 335

Tyr Leu Glu Phe Val Val Asn Glu Leu Asn Ile Glu Leu Glu Lys Glu
        340                 345                 350

Gln Tyr Lys Ile Ile Thr Pro Lys Asn Ser Ala Glu Arg Gly Ala Gln
        355                 360                 365

Leu Ser Ile Ile Ala Ala Arg Asn Gly Lys Glu Ile Phe Asp Gly Leu
370                 375                 380

Leu Ala His Gly Ile Leu Gly Asp Trp Arg Glu Pro Asn Val Ile Arg
385                 390                 395                 400

Leu Ser Pro Val Pro Leu Tyr Asn Ser Phe Glu Asp Ile Tyr Gln Thr
                405                 410                 415

Gly Lys Ala Leu Ser Glu Val Thr Arg Lys Ile Leu Thr Thr Ala
        420                 425                 430

<210> SEQ ID NO 42
<211> LENGTH: 449
<212> TYPE: PRT
<213> ORGANISM: Pedobacter sp. BAL39

<400> SEQUENCE: 42

Met Lys Val Val Asp Asn Lys Lys Thr Gly Leu Phe Asn Tyr Ile Pro
1               5                   10                  15

Phe Leu Trp Ile Phe Gly Thr Met Asn Phe Glu Asn Thr Leu Ala Phe
                20                  25                  30

Ala Gln Gly Leu Asp Gln Ala Asp Pro Leu Arg Asp Leu Arg Asn Glu
        35                  40                  45

Phe Leu Phe Pro Gln Gln Asn Gly Lys Pro Phe Ile Tyr Leu Cys Gly
50                  55                  60
```

```
Asn Ser Leu Gly Leu Gln Pro Lys Val Ala Arg Glu Val Leu Asp Arg
 65                  70                  75                  80

Gln Leu Asn Asn Trp Gln Asn Leu Ala Val Glu Gly Trp Phe Glu Gly
                 85                  90                  95

Glu Thr Pro Trp Met Tyr Tyr His Lys Ala Leu Lys Glu Leu Met Ala
            100                 105                 110

Pro Ile Val Gly Ala Arg Pro Ala Glu Val Cys Pro Met Asn Thr Leu
        115                 120                 125

Thr Val Asn Leu His Leu Leu Met Val Ser Phe Tyr Lys Pro Lys Ala
    130                 135                 140

Lys Arg Phe Lys Ile Met Met Glu Ala Gly Ala Phe Pro Ser Asp Gln
145                 150                 155                 160

Tyr Ala Ile Glu Ser Gln Val Arg Phe His Gly Tyr Asp Pro Lys Asp
                165                 170                 175

Ala Ile Ile Glu Val Ser Pro Arg Pro Gly Glu Tyr Thr Leu Arg Thr
            180                 185                 190

Glu Asp Ile Leu Glu Gln Ile Ser Leu Gln Gly Asp Gln Ile Ala Leu
        195                 200                 205

Val Leu Phe Gly Gly Ile Asn Tyr Phe Thr Gly Gln Trp Phe Asp Met
    210                 215                 220

Glu Ala Ile Thr Arg Ala Gly His Gln Ala Gly Ala Val Val Gly Phe
225                 230                 235                 240

Asp Leu Ala His Ala Ala Gly Asn Val Pro Val Gln Leu His Asp Trp
                245                 250                 255

Asp Val Asp Phe Ala Cys Trp Cys Ser Tyr Lys Tyr Gln Asn Ser Gly
            260                 265                 270

Pro Gly Gly Ile Ser Gly Ile Phe Val His Glu Arg His Phe Gly Asp
        275                 280                 285

Gln Thr Leu Ser Arg Phe Ala Gly Trp Trp Gly Tyr Gln Glu Ser Gln
    290                 295                 300

Arg Phe Lys Met Glu Lys Gly Phe Val Pro Glu Ala Gly Ala Asp Gly
305                 310                 315                 320

Trp Gln Val Ser Cys Thr Gln Val Met Pro Met Ala Leu Tyr His Ala
                325                 330                 335

Ala Leu Gln Ile Phe Glu Lys Ala Gly Phe Ile Gly Pro Leu Arg Lys
            340                 345                 350

Lys Ser Lys Ala Leu Thr Ala Tyr Leu Phe Tyr Leu Ile Asn Glu Val
        355                 360                 365

Asn Asn Glu Leu Cys Glu Met Gln Tyr Gln Val Ile Thr Pro Ser Ser
    370                 375                 380

Ala Glu Asp Arg Gly Ala Gln Val Ser Ile Ile Ala Lys Ala Asn Gly
385                 390                 395                 400

Lys Tyr Ile Phe Glu Gln Leu Val Ala Asn Asn Val Leu Gly Asp Trp
                405                 410                 415

Arg Glu Pro Asn Val Ile Arg Leu Ser Pro Val Pro Ser Tyr Asn Ser
            420                 425                 430

Phe Glu Asp Val Phe Arg Thr Ala Glu Leu Leu Leu Gln Ile Gly Arg
        435                 440                 445

Lys

<210> SEQ ID NO 43
<211> LENGTH: 428
<212> TYPE: PRT
<213> ORGANISM: Pedobacter sp. V48
```

<400> SEQUENCE: 43

```
Met Asn Phe Glu Asn Asn Leu Ala Phe Ala Gln Ser Leu Asp Gln Ala
1               5                   10                  15

Asp Pro Leu Ser Ser Phe Arg His Asp Phe Leu Phe Pro Gln Gln Asn
            20                  25                  30

Gly Asn Pro Phe Ile Tyr Leu Cys Gly Asn Ser Leu Gly Leu Gln Pro
        35                  40                  45

Lys Ala Val Arg Lys Val Val Asp Glu Gln Leu Asn Asn Trp Arg Asn
50                  55                  60

Leu Ala Val Glu Gly Trp Phe Glu Gly Asp Asn Pro Trp Met Phe Tyr
65                  70                  75                  80

His Lys Glu Leu Lys Lys Leu Met Gly Pro Leu Val Gly Ala Ser Thr
                85                  90                  95

Asp Glu Val Cys Pro Met Asn Thr Leu Thr Val Asn Leu His Leu Leu
            100                 105                 110

Met Val Ser Phe Tyr Lys Pro Val Arg Gly Arg Phe Lys Ile Ile Met
        115                 120                 125

Glu Ala Gly Ala Phe Pro Ser Asp Gln Tyr Ala Val Glu Ser Gln Val
130                 135                 140

Arg Phe His Gly Tyr Asp Ala Lys Glu Ala Ile Val Glu Val Ala Pro
145                 150                 155                 160

Arg Ile Gly Glu Tyr Ile Leu Arg Thr Glu Asp Ile Leu Ala Gln Ile
                165                 170                 175

Ala Lys His Gly Asp Glu Val Ala Leu Val Leu Phe Ser Gly Val Asn
            180                 185                 190

Tyr Phe Thr Gly Gln Trp Phe Asp Met Glu Ala Ile Thr Met Ala Gly
        195                 200                 205

His Ala Glu Gly Ala Val Val Gly Phe Asp Leu Ala His Ala Ala Gly
210                 215                 220

Asn Val Pro Leu Lys Leu His Asp Trp Asp Ile Asp Phe Ala Cys Trp
225                 230                 235                 240

Cys Ser Tyr Lys Tyr Gln Asn Ser Gly Pro Gly Gly Ile Ser Gly Ile
                245                 250                 255

Phe Val His Glu Lys His Phe Thr Asp Thr Thr Leu Asn Arg Phe Ala
            260                 265                 270

Gly Trp Trp Gly Tyr Gln Gln Ala His Arg Phe Lys Met Glu Lys Gly
        275                 280                 285

Phe Leu Pro Glu Pro Gly Ala Asp Gly Trp Gln Val Ser Cys Thr Gln
290                 295                 300

Val Met Pro Met Ala Leu Tyr Phe Ala Ser Leu Gln Ile Phe Glu Lys
305                 310                 315                 320

Ala Gly Phe Ile Glu Pro Leu Arg Leu Lys Ser Lys Thr Leu Thr Ser
                325                 330                 335

Tyr Leu Phe His Ile Val Asn Gln Val Asn Lys Leu Leu Ser Cys Glu
            340                 345                 350

Gln Phe Glu Ile Ile Thr Pro Asp Asn Glu Asn Glu Arg Gly Ala Gln
        355                 360                 365

Val Ser Ile Ile Ala Lys Gln Lys Gly Lys Glu Ile Phe Glu Lys Leu
370                 375                 380

Ile Ala Asn Asn Val Leu Gly Asp Trp Arg Glu Pro Asn Val Ile Arg
385                 390                 395                 400

Leu Ser Pro Val Pro Leu Tyr Asn Ser Phe Glu Asp Val Phe Arg Thr
```

```
                      405                 410                 415
Gly Glu Leu Leu Leu Gln Ile Thr Lys Gly Val Ile
            420                 425

<210> SEQ ID NO 44
<211> LENGTH: 428
<212> TYPE: PRT
<213> ORGANISM: Rhodonellum psychrophilum

<400> SEQUENCE: 44

Met Lys Asp Ile Lys Tyr Glu Tyr Ser Glu Phe Phe Ala Arg Gln Leu
1               5                   10                  15

Asp Asn Glu Asp Pro Leu Lys Asp Phe Arg Asn Glu Phe Tyr Phe Pro
            20                  25                  30

Lys Ile Glu Gly Lys Glu Ala Ile Tyr Phe Cys Gly Asn Ser Leu Gly
        35                  40                  45

Leu Gln Pro Arg Ser Thr Lys Glu Tyr Ile Gln Arg Glu Leu Asp Asn
    50                  55                  60

Trp Ala Glu Leu Ala Val Asp Gly His Phe Lys Gly Glu Asp Ala Trp
65                  70                  75                  80

Tyr His Val Arg Lys Ser Lys Pro Ala Leu Ser Glu Ile Val Gly
                85                  90                  95

Ala His Glu His Glu Val Val Ala Met Asn Asn Leu Ser Ser Asn Leu
            100                 105                 110

His Phe Leu Met Val Ser Phe Tyr Arg Pro Ser Lys Thr Arg Phe Lys
        115                 120                 125

Ile Ile Thr Glu Ala Gly Ala Phe Pro Ser Asp Met Tyr Met Leu Glu
    130                 135                 140

Thr Gln Val Lys Phe His Gly Leu Asp Pro Glu Lys Thr Ile Ile Glu
145                 150                 155                 160

Val Ala Pro Arg Pro Gly Glu His Thr Leu Arg Thr Glu Asp Ile Leu
                165                 170                 175

Leu Ala Ile Glu Glu Gln Gly Glu Glu Leu Ala Leu Val Met Met Ala
            180                 185                 190

Gly Leu Gln Tyr Tyr Thr Gly Gln Val Phe Asp Met Glu Ser Ile Thr
        195                 200                 205

Arg Ala Gly His Ser Val Gly Ala Asn Val Gly Phe Asp Leu Ala His
    210                 215                 220

Ala Ala Gly Asn Val Pro Met Ser Leu His Asp Trp Gly Val Asp Phe
225                 230                 235                 240

Ala Thr Trp Cys Ser Tyr Lys Tyr Met Asn Ser Gly Pro Gly Asn Val
                245                 250                 255

Ser Gly Val Phe Val His Glu Arg His Ala Gln Asn Pro Asp Leu Pro
            260                 265                 270

Arg Phe Ala Gly Trp Trp Gly His Asp Glu Glu Arg Phe Lys Met
        275                 280                 285

Glu Lys Gly Phe Lys Pro Met Tyr Gly Ala Asp Gly Trp Gln Val Ala
    290                 295                 300

Asn Ser Asn Val Leu Ala Leu Ala Ala His Gln Ser Ser Leu Asp Ile
305                 310                 315                 320

Phe Glu Arg Ala Gly Ile Lys Asn Leu Arg Glu Lys Ser Glu Leu Leu
                325                 330                 335

Thr Gly Tyr Leu Glu Phe Leu Ile Gln Gln Ile Ser Gly Asp Ser Gly
            340                 345                 350
```

-continued

```
Val Ile Glu Ile Ile Thr Pro Lys Asn Pro Gln Glu Arg Gly Cys Gln
            355                 360                 365

Leu Ser Leu Leu Val His Lys Gly Gly Lys Ala Val Phe Asp Glu Leu
        370                 375                 380

Tyr Leu Asn Gly Ile Ile Gly Asp Trp Arg His Pro Lys Val Met Arg
385                 390                 395                 400

Ile Ala Pro Thr Pro Leu His Asn Ser Phe Leu Asp Val Phe Arg Phe
                405                 410                 415

Ala Gln Ile Leu Glu Lys Ser Ile Leu Lys Phe Ala
            420                 425

<210> SEQ ID NO 45
<211> LENGTH: 430
<212> TYPE: PRT
<213> ORGANISM: Salinispora arenicola

<400> SEQUENCE: 45

Met Asn Lys Glu Glu Leu Asp Gln Gly Glu Lys Ala Ala Asn Arg Leu
1               5                   10                  15

Asp Thr Ala Asp Pro Gly His Arg His Leu Phe His Leu Pro Pro Ser
            20                  25                  30

Asp Gly Gly Arg Tyr Gln Gln Ala Ala Tyr Leu Ala Gly Asn Ser Leu
        35                  40                  45

Gly Leu Gln Pro Leu Ala Thr Arg Asp Glu Leu Leu Ala Asp Leu Asp
    50                  55                  60

Ala Trp Arg Arg Leu Gly Val Glu Gly His Leu Glu Ala Asp Arg Pro
65                  70                  75                  80

Trp Leu Pro Tyr His Glu Leu Leu Thr Ala Pro Thr Ala Arg Leu Val
                85                  90                  95

Gly Ala Arg Pro Ala Glu Val Val Val Met Asn Ser Leu Thr Val Asn
            100                 105                 110

Leu His Leu Leu Met Val Ser Phe Tyr Arg Pro Val Gly Ala Arg Thr
        115                 120                 125

Arg Ile Val Ile Glu Asp Asn Ala Phe Pro Ser Asp Ser Tyr Ala Val
    130                 135                 140

Arg Ser Gln Ala Arg Phe His Gly Leu Asp Pro Asp Thr Thr Val Val
145                 150                 155                 160

Arg Leu Ala Pro Arg Pro Gly Glu Asp Thr Leu Arg Thr Val Asp Val
                165                 170                 175

Leu Asp Leu Leu Ala Ala Glu Gly Asp Thr Ile Ala Leu Val Leu Leu
            180                 185                 190

Gly Gly Val Asn Tyr Leu Thr Gly Glu Leu Leu Asp Ile Pro Ala Ile
        195                 200                 205

Thr Ala Ala Gly Arg Ala Ala Gly Ala Ala Val Gly Trp Asp Leu Ala
    210                 215                 220

His Ala Ala Gly Asn Val Pro Leu Ser Leu His Asp Trp Asp Val Asp
225                 230                 235                 240

Phe Ala Ala Trp Cys Ser Tyr Lys Tyr Leu Asn Ser Gly Pro Gly Gly
                245                 250                 255

Leu Ser Ser Val Phe Val His Glu Arg His Leu Ala Asp Pro Thr Leu
            260                 265                 270

Pro Arg Phe Glu Gly Trp Trp Ser Thr Asp Ala Ala Val Arg Phe Glu
        275                 280                 285

Met Ser Pro Val Ala Arg Pro Ala Thr Ala Glu Ala Trp Gln Val
    290                 295                 300
```

```
Ser Asn Pro Pro Ile Phe Ala Met Gly Pro Val Arg Thr Ser Leu Glu
305                 310                 315                 320

Leu Phe Asp Ser Val Gly Met Thr Ala Leu Arg Glu Arg Ser Val Arg
            325                 330                 335

Leu Thr Gly Tyr Leu Glu Trp Leu Leu Asp Gln Ile Thr Pro Gly Arg
            340                 345                 350

Gln Leu Ala Val Val Thr Pro Arg Asp Pro Asp Arg Arg Gly Ala Gln
            355                 360                 365

Leu Ser Val Arg Val Gly Ser Gly Ala Ala Glu Leu Thr Lys Arg
370                 375                 380

Leu Arg Cys Glu Tyr Gly Val Ile Ala Asp Ala Arg Glu Pro Asp Ile
385                 390                 395                 400

Val Arg Phe Ala Pro Val Pro Leu Tyr Ser Thr Tyr His Asp Cys Trp
            405                 410                 415

Arg Val Ala Asp Ala Leu Ala Ala Thr Val Glu Val Arg Gly
            420                 425                 430

<210> SEQ ID NO 46
<211> LENGTH: 425
<212> TYPE: PRT
<213> ORGANISM: Saprospira grandis str. Lewin

<400> SEQUENCE: 46

Met Gln Glu Val Gln Phe Glu Asp Ala Leu Asp Tyr Ala Lys Ala Gln
1               5                   10                  15

Asp Val Ser Asp Pro Leu Ala His Phe Arg Pro Gln Phe His Phe Pro
            20                  25                  30

Lys Gln Ala Asp Gly Ser Pro Ile Ile Tyr Leu Cys Gly Asn Ser Leu
        35                  40                  45

Gly Leu Gln Pro Arg Leu Ala Gln Gln Leu Met Gln Asp Glu Met Asp
    50                  55                  60

Val Trp Lys Glu Leu Ala Val Glu Gly His Phe Lys Ala Glu Arg Pro
65                  70                  75                  80

Trp Met Thr Tyr His Glu Glu Phe Ser Arg Gln Leu Ser Pro Ile Val
                85                  90                  95

Gly Ala Leu Pro Lys Glu Ile Thr Val Met Asn Thr Leu Ser Val Asn
            100                 105                 110

Leu His Leu Met Met Val Ser Phe Tyr Arg Pro Thr Lys Ser Arg Tyr
        115                 120                 125

Lys Ile Val Ile Glu Gly Gly Ala Phe Pro Ser Asp Lys Tyr Ala Val
130                 135                 140

Asp Ser Gln Leu Arg Phe His Gly Ile Asp Pro Gln Asp Gly Leu Ile
145                 150                 155                 160

Gln Leu Arg Pro Arg Met Gly Glu Asp His Leu Arg Thr Glu Asp Ile
                165                 170                 175

Leu Gln Ala Leu Glu Arg Glu Lys Asp Ser Ile Ala Leu Val Met Leu
            180                 185                 190

Ser Gly Ile Asn Tyr Tyr Thr Gly Gln Cys Phe Asp Met Lys Ser Ile
        195                 200                 205

Thr Lys Lys Gly His Glu Ile Gly Ala Met Val Gly Phe Asp Leu Ala
    210                 215                 220

His Ala Ala Gly Asn Val Arg Leu Gln Leu His Asp Trp Gly Met Asp
225                 230                 235                 240

Phe Ala Val Trp Cys His Tyr Lys Tyr Leu Asn Ser Gly Pro Gly Cys
```

```
                245                 250                 255
Ile Ala Gly Ala Phe Val His Glu Arg His Leu Asn Arg Lys Asp Leu
            260                 265                 270

Pro Arg Phe Glu Gly Trp Trp Gly His His Lys Glu Ser Arg Phe Lys
        275                 280                 285

Met Pro Ala Thr Phe Glu Pro Ala Asn Ala Asp Ala Trp Gln Ile
    290                 295                 300

Ser Asn Ala Pro Ile Leu Ala Met Val Pro Met Arg Ala Ser Leu Ala
305                 310                 315                 320

Leu Phe Asn Glu Ala Gly Met Asp Arg Leu Leu Ala Lys Ser Lys Lys
            325                 330                 335

Leu Thr Ala Tyr Leu Glu Phe Leu Leu Asn Gln Leu Pro Thr Asp Arg
            340                 345                 350

Ile Arg Ile Leu Thr Pro Lys Asp Pro Lys Asp Arg Gly Ala Gln Leu
            355                 360                 365

Ser Ile Gln Val Lys Gly Ala Asp Arg Ser Leu Phe Asp Asp Leu Val
        370                 375                 380

Lys Asn Gly Val Ile Gly Asp Trp Arg Glu Pro Asp Val Ile Arg Ile
385                 390                 395                 400

Ser Pro Ala Pro Ile Tyr Asn Ser Phe Glu Asp Val Tyr Arg Met Val
                405                 410                 415

Gln Ile Leu Lys Lys Cys Leu Gln Leu
            420                 425

<210> SEQ ID NO 47
<211> LENGTH: 427
<212> TYPE: PRT
<213> ORGANISM: Stigmatella aurantiaca DW4/3-1

<400> SEQUENCE: 47

Met Thr Glu Ala Ser Met Arg Phe Glu Glu Gly Glu Gly Phe Ala Arg
1               5                   10                  15

Arg Met Asp Ala Glu Asp Pro Leu Arg Ser Phe Arg Glu Glu Phe Leu
            20                  25                  30

Phe Pro Gln Ser Pro Gln Gly Glu Pro Leu Val Tyr Leu Ala Gly Asn
        35                  40                  45

Ser Leu Gly Leu Gln Pro Arg Arg Ala Gln Gln Tyr Val Gln Glu Glu
    50                  55                  60

Met Glu Asp Trp Ala Arg Leu Gly Val Glu Gly His Phe His Ala Arg
65                  70                  75                  80

Arg Pro Trp Leu Pro Tyr His Glu Asn Leu Thr Gly Gln Thr Ala Arg
                85                  90                  95

Leu Val Gly Ala Leu Pro Leu Glu Val Val Val Met Asn Thr Leu Ser
            100                 105                 110

Val Asn Leu His Leu Met Met Val Ser Phe Tyr Arg Pro Thr Arg Glu
        115                 120                 125

Arg Phe Lys Ile Leu Ile Glu Gly Gly Ala Phe Pro Ser Asp Gln Tyr
    130                 135                 140

Ala Val Ala Ser Gln Ala Arg Phe His Gly Phe Asp Pro Lys Asp Ala
145                 150                 155                 160

Val Leu Lys Leu Glu Pro Arg Ala Gly Glu Asp Thr Leu Arg Thr Glu
                165                 170                 175

Asp Ile Leu Glu Thr Leu Glu Arg His Gly Ser Glu Ile Ala Leu Val
            180                 185                 190
```

```
Leu Leu Gly Asn Val Asn Tyr Leu Thr Gly Gln Ala Phe Asp Met Lys
            195                 200                 205

Ala Leu Thr Gln Ala Ala His Ala Arg Gly Cys Arg Val Gly Phe Asp
        210                 215                 220

Leu Ala His Gly Ala Gly Asn Leu Arg Leu Ser Leu His Asp Asp Gly
225                 230                 235                 240

Pro Asp Phe Ala Val Trp Cys Ser Tyr Lys Tyr Leu Asn Gly Gly Pro
                245                 250                 255

Gly Ala Leu Gly Gly Val Phe Ile His Glu Arg His Ala Arg Ala Glu
            260                 265                 270

Gly Leu Pro Arg Phe Glu Gly Trp Trp Gly Asn Asp Lys Ala Ile Arg
        275                 280                 285

Phe Gln Met Gly Pro Asp Phe Val Pro Leu Pro Gly Ala Glu Gly Trp
    290                 295                 300

Gln Leu Ser Asn Pro Pro Ile Phe Gln Leu Ala Ala Leu Arg Ala Ser
305                 310                 315                 320

Met Glu Leu Phe Asp Arg Ala Thr Met Pro Ser Leu Arg Gly Lys Gly
                325                 330                 335

Asp Arg Leu Thr Gly Tyr Leu Glu Phe Leu Asp Arg Leu Pro Ser
            340                 345                 350

Gly Phe Val Arg Ile Thr Thr Pro Arg Asp Val Lys Ala Arg Gly Ser
        355                 360                 365

Gln Leu Ser Leu Arg Phe Ser Lys Asp Pro Arg Arg Leu Leu Thr Arg
    370                 375                 380

Leu Ser Glu Ala Gly Val Cys Cys Asp Phe Arg Ser Pro Asp Ile Ile
385                 390                 395                 400

Arg Ala Ala Pro Ala Pro Leu Tyr Asn Ser Phe Gln Asp Val Tyr Arg
                405                 410                 415

Phe Val Lys Val Leu Glu Ser His Ala Arg Asp
            420                 425

<210> SEQ ID NO 48
<211> LENGTH: 423
<212> TYPE: PRT
<213> ORGANISM: Xanthomonas axonopodis

<400> SEQUENCE: 48

Met Thr Asp Pro Leu Ser Arg Ala His Ala Ala Leu Asp Ala Ala
1               5                   10                  15

Asp Pro Leu Arg Asn Leu Arg Asp Ala Phe Val Phe Pro Gln His Gly
                20                  25                  30

Asp Asp Asp Gln Thr Tyr Phe Val Gly Asn Ser Leu Gly Leu Gln Pro
            35                  40                  45

Arg Ala Ala Arg Ala Met Val Asp Glu Val Leu Asp Gln Trp Gly Ala
        50                  55                  60

Leu Ala Val Glu Gly His Phe Thr Gly Pro Thr Gln Trp Leu Thr Tyr
65                  70                  75                  80

His Gln Leu Val Arg Asp Ala Leu Ala Arg Val Gly Ala Gln Pro
                85                  90                  95

Gly Glu Val Val Ala Met Asn Thr Leu Ser Val Asn Leu His Leu Met
            100                 105                 110

Met Ala Ser Phe Tyr Arg Pro Thr Ala Glu Arg Gly Ala Ile Leu Ile
        115                 120                 125

Glu Ala Gly Ala Phe Pro Ser Asp Arg His Ala Val Glu Ser Gln Leu
    130                 135                 140
```

Arg Leu His Gly Leu Asp Pro Ala Thr His Leu Ile Glu Val Glu Ala
145                 150                 155                 160

Asp Glu Pro Asn Gly Thr Val Ser Met Ser Ala Ile Ala Glu Ala Ile
                165                 170                 175

Ala Gln His Gly Pro His Leu Ala Leu Val Leu Trp Pro Gly Ile Gln
            180                 185                 190

Tyr Arg Thr Gly Gln Ala Phe Asp Leu Ala Glu Ile Val Arg Leu Ala
        195                 200                 205

Arg Ala Gln Gly Ala Ala Val Gly Phe Asp Leu Ala His Ala Val Gly
    210                 215                 220

Asn Leu Pro Leu Thr Leu His Asp Asp Gly Val Asp Phe Ala Val Trp
225                 230                 235                 240

Cys His Tyr Lys Tyr Leu Asn Ala Gly Pro Gly Ala Val Gly Gly Cys
                245                 250                 255

Phe Val His Ala Arg His Ala Thr Ser Asp Leu Pro Arg Met Ala Gly
            260                 265                 270

Trp Trp Gly His Glu Gln Gln Thr Arg Phe Arg Met Asp Pro Gln Phe
        275                 280                 285

Val Pro Ser Pro Gly Ala Glu Gly Trp Gln Leu Ser Asn Pro Pro Val
    290                 295                 300

Leu Ala Leu Ala Pro Leu Arg Ala Ser Leu Ala Leu Phe Asp Gln Ala
305                 310                 315                 320

Gly Met Ala Ala Leu Arg Ala Lys Ser Glu Gln Leu Thr Gly His Leu
                325                 330                 335

Glu Gln Leu Ile His Ala Arg Ala Pro Gln Val Leu Gln Ile Val Thr
            340                 345                 350

Pro Val Glu Pro Ala Arg Arg Gly Cys Gln Leu Ser Leu Arg Val Ala
        355                 360                 365

Gly Gly Arg Ala Arg Gly Arg Ala Leu Phe Glu His Leu His Ala Ala
    370                 375                 380

Gly Val Leu Gly Asp Trp Arg Glu Pro Asp Val Ile Arg Ile Ala Pro
385                 390                 395                 400

Val Pro Leu Tyr Asn Arg Phe Ser Asp Leu His Thr Phe Val Glu Gln
                405                 410                 415

Val Glu Ala Trp Ala Ala Ala
            420

<210> SEQ ID NO 49
<211> LENGTH: 422
<212> TYPE: PRT
<213> ORGANISM: Psychroflexus gondwanensis

<400> SEQUENCE: 49

Met Lys Tyr Gln Asn Thr Lys Ser Phe Ala Glu Gln Leu Asp Glu Ala
1               5                   10                  15

Asp Pro Leu Lys Ala Tyr Arg Ser Glu Phe Leu Phe Pro Lys Ala Lys
                20                  25                  30

Asp Gly Ser Pro Lys Val Tyr Leu Cys Gly Asn Ser Leu Gly Leu Gln
            35                  40                  45

Pro Lys Gln Thr Ser Ala Phe Ile Gln Gln Glu Gln Leu Asp Trp Ala
        50                  55                  60

Asp Leu Gly Val Glu Gly His Ser His Ala Thr His Pro Trp Met Thr
65                  70                  75                  80

Ser Asn Glu Asp Leu Ala Asp Ser Met Ala Lys Ile Val Gly Ala Gln

```
                85                  90                  95
Pro Gln Glu Val Val Ile Met Asn Thr Leu Thr Val Asn Leu His Leu
            100                 105                 110

Met Met Val Ser Phe Tyr Lys Pro Thr Pro Lys Lys Phe Lys Ile Leu
            115                 120                 125

Ile Glu Ser Asp Ala Phe Pro Ser Asp Lys Tyr Ala Val Glu Ser Gln
            130                 135                 140

Leu Lys Phe His Asn Ile Asp Pro Lys Glu Gly Leu Leu Leu Trp Lys
145                 150                 155                 160

Pro Arg Pro Gly Glu His Leu Cys Arg Thr Glu Asp Phe Glu Gln Ile
                165                 170                 175

Ile Glu Glu His Gly Asp Glu Ile Ala Leu Val Met Ile Gly Ser Thr
            180                 185                 190

Asn Tyr Tyr Ser Gly Gln Ala Tyr Asp Leu Lys Arg Ile Thr Glu Val
            195                 200                 205

Ser Lys Thr Lys Asp Ile Thr Val Gly Phe Asp Leu Ala His Gly Ala
            210                 215                 220

Gly Asn Ile Gln Pro Asn Leu His Asp Ile Gly Ala Asp Phe Ala Val
225                 230                 235                 240

Trp Cys Thr Tyr Lys Tyr Leu Asn Ser Gly Pro Gly Ser Leu Gly Gly
                245                 250                 255

Cys Phe Ile His Glu Lys His Ile Ala Asp Glu His Ile Asn Arg Phe
            260                 265                 270

Val Gly Trp Trp Gly His Asn Lys Asp Ser Arg Phe Asn Met Arg Val
            275                 280                 285

Asp Phe Asp Pro Ile Pro Thr Ala Asp Gly Trp Gln Leu Ser Asn Pro
            290                 295                 300

Pro Ile Leu Ser Leu Ala Gly Thr Arg Ser Ser Leu Asp Leu Phe Asp
305                 310                 315                 320

Lys Ala Gly Phe Asp Asn Ile Arg Lys Lys Ser Val Leu Leu Thr Gly
                325                 330                 335

Phe Leu Glu Phe Leu Ile Asp Asp Leu Asp Met Glu Glu Ile Ser Ile
            340                 345                 350

Leu Thr Pro Arg Ser Pro Glu Glu Arg Gly Cys Gln Leu Ser Ile Gln
            355                 360                 365

Val Lys Asn Ala Asn Lys Ser Leu Phe His Gln Leu Met Asp Lys Gly
            370                 375                 380

Val Val Ala Asp Trp Arg Glu Pro Asp Val Ile Arg Ile Ala Pro Ala
385                 390                 395                 400

Pro Leu Tyr Asn Ser Tyr Thr Asp Val Phe Thr Phe Val Glu Ile Leu
                405                 410                 415

Lys His Cys Leu Asn Ala
            420

<210> SEQ ID NO 50
<211> LENGTH: 422
<212> TYPE: PRT
<213> ORGANISM: Lewinella cohaerens

<400> SEQUENCE: 50

Met Thr Tyr Gln Ala Thr Arg Glu Tyr Ala Gln Ser Gln Asp Asp Lys
1               5                   10                  15

Asp Pro Met Arg Gly Phe Arg Glu Arg Phe His Leu Pro Arg Gln Ala
            20                  25                  30
```

```
Asn Gly Glu Pro Phe Ile Tyr Leu Cys Gly Asn Ser Leu Gly Leu Gln
             35                  40                  45

Pro Lys Ser Thr Lys Ala Ala Ile Asp Gln Glu Leu Leu Asp Trp Gln
 50                  55                  60

Asn Leu Gly Val Glu Gly His Leu His Ala Lys Asn Pro Trp Leu Pro
 65                  70                  75                  80

Tyr His Glu Phe Leu Thr Glu Lys Met Ala Glu Ile Val Gly Ala Lys
                 85                  90                  95

Pro Ile Glu Val Val Met Met Asn Thr Leu Thr Val Asn Leu His Leu
            100                 105                 110

Met Met Val Ser Phe Tyr Arg Pro Glu Gly Lys Arg Thr Lys Ile Leu
            115                 120                 125

Met Glu Ala Asp Ala Phe Pro Ser Asp Arg Tyr Ala Ile Ser Ser Gln
130                 135                 140

Leu Lys Phe His Gly Tyr Asp Pro Ala Glu His Leu Val Glu Leu Lys
145                 150                 155                 160

Ala Arg Asp Gly Glu Val Leu Ile Arg Glu Asp Ile Ala His Ile
                165                 170                 175

Leu Glu Glu Gln Gly Ala Glu Ile Ala Leu Val Leu Leu Gly Asn Thr
            180                 185                 190

Asn Tyr Tyr Thr Gly Gln Phe Phe Asn Met Pro Glu Ile Thr Lys Leu
            195                 200                 205

Ala His Ala Gln Gly Cys Met Val Gly Phe Asp Cys Ala His Gly Ala
            210                 215                 220

Gly Asn Val Pro Leu Asp Leu His Asp Ser Gly Ala Asp Phe Ala Val
225                 230                 235                 240

Trp Cys Ser Tyr Lys Tyr Ile Asn Ser Gly Pro Gly Ser Val Ser Gly
                245                 250                 255

Cys Phe Val His Glu Arg His Ala His Asp Lys Glu Leu Pro Arg Phe
            260                 265                 270

Thr Gly Trp Trp Gly His Asn Lys Val Thr Arg Phe Gly Met Arg Asp
            275                 280                 285

Asp Phe Asp Pro Ile Pro Gly Val Glu Ala Trp Gln Leu Ser Asn Pro
290                 295                 300

Pro Ile Leu Ser Leu Ala Ala Ile Lys Ala Ser Leu Glu Val Phe Ala
305                 310                 315                 320

Glu Ala Gly Met Asn Asn Leu Arg Gln Lys Ser Leu Ala Leu Thr Gly
                325                 330                 335

Tyr Leu Glu Tyr Leu Val Asp Gln Leu Pro Gly Gly Lys Ile Ser Ile
            340                 345                 350

Ile Thr Pro Arg Asp Pro Glu Arg Arg Gly Cys Gln Leu Ser Ile Gln
            355                 360                 365

Val Gln Asp Ala Asp Lys Ser Leu Tyr Glu Ala Ile Ser Ala Ala Gly
370                 375                 380

Val Ile Ala Asp Trp Arg Glu Pro Asp Val Ile Arg Val Ala Pro Val
385                 390                 395                 400

Pro Leu Tyr Asn Thr Phe Thr Glu Val Tyr Asp Phe Val Lys Ile Leu
                405                 410                 415

Gly Glu Lys Met Glu Ala
            420

<210> SEQ ID NO 51
<211> LENGTH: 425
<212> TYPE: PRT
```

<213> ORGANISM: Lewinella persica

<400> SEQUENCE: 51

Met Val Glu Glu Phe Gln Asn Asp Leu Ala Phe Ala Arg Lys Met Asp
1               5                   10                  15

Glu Arg Asp Glu Leu Arg Ala Tyr Arg Ser Gln Tyr His Met Pro Val
            20                  25                  30

Gln Ala Asn Gly Gln Pro Tyr Val Tyr Leu Cys Gly Asn Ser Leu Gly
        35                  40                  45

Leu Gln Pro Lys Ala Thr Glu Gly Tyr Leu Leu Gln Glu Leu Glu Asp
    50                  55                  60

Trp Lys Asn Leu Gly Val Glu Gly His Phe His Ala Lys Asn Pro Trp
65                  70                  75                  80

Met Pro Tyr His Glu Phe Leu Thr Glu Ala Met Ala Arg Val Val Gly
                85                  90                  95

Ala Lys Pro Ser Glu Val Val Met Asn Thr Leu Thr Val Asn Leu
            100                 105                 110

His Leu Met Met Val Ser Phe Tyr Arg Pro Val Gly Arg Arg Lys Lys
            115                 120                 125

Ile Ile Ile Glu Ala Asp Ala Phe Pro Ser Asp Lys Tyr Ala Val Glu
            130                 135                 140

Ser Gln Ile Arg Phe His Gly Leu Ser Pro Glu Asp Cys Leu Ile Glu
145                 150                 155                 160

Leu Lys Ala Arg Asp Gly Glu Val Cys Leu Arg Gln Glu Asp Ile Leu
                165                 170                 175

Gly Val Ile Asp Ala His Ser Glu Asp Ile Ala Leu Ile Leu Leu Gly
            180                 185                 190

Asn Thr Asn Tyr Tyr Thr Gly Gln Phe Phe Asp Met Lys Thr Ile Ser
            195                 200                 205

Glu His Gly His Ala Lys Gly Cys Met Val Gly Phe Asp Cys Ala His
    210                 215                 220

Gly Ala Gly Asn Val Pro Leu Asn Leu His Asp Ser Gly Cys Asp Phe
225                 230                 235                 240

Ala Val Trp Cys Asn Tyr Lys Tyr Leu Asn Ser Gly Pro Gly Gly Met
                245                 250                 255

Gly Gly Ala Phe Ile His Glu Arg His Ala Asp Ser Lys Asp Ile Pro
            260                 265                 270

Arg Phe Glu Gly Trp Trp Gly His Asn Lys Glu Thr Arg Phe Lys Met
            275                 280                 285

Arg Asp Ala Phe Asp Pro Thr Pro Gly Thr Glu Ala Trp Gln Leu Ser
    290                 295                 300

Asn Pro Pro Ile Leu Ala Met Val Ala Val Trp Ser Ala Leu Lys Leu
305                 310                 315                 320

Phe Asp Glu Val Gly Met Thr Arg Leu Arg Lys Lys Ala Ile Ser Leu
                325                 330                 335

Thr Gly Tyr Leu Glu Tyr Leu Val Asn Thr Leu Gly Asp Asp Val Val
            340                 345                 350

Asn Ile Val Thr Pro Ala Asp Pro Ala Gln Arg Gly Ser Gln Leu Ser
            355                 360                 365

Ile Gln Val Lys Thr Ala Asp Lys Lys Leu Phe Asn Lys Ile Thr Glu
    370                 375                 380

Ala Gly Val Ile Ala Asp Trp Arg Glu Pro Asp Val Ile Arg Val Ala
385                 390                 395                 400

```
Pro Val Pro Met Tyr Asn Ser Tyr Glu Asp Val Tyr Asn Phe Tyr Thr
                405                 410                 415

Ile Leu Lys Ser Ala Ile Ala Gly Asn
        420                 425

<210> SEQ ID NO 52
<211> LENGTH: 424
<212> TYPE: PRT
<213> ORGANISM: Pontibacter roseus

<400> SEQUENCE: 52

Met Asn Tyr Gln Asn Thr Leu Ala Phe Ala Gln Glu Gln Asp Asn Leu
1               5                   10                  15

Asp Pro Leu Lys His Phe Lys Asp Arg Phe Tyr Phe Pro Gln Val Asn
            20                  25                  30

Gly Arg Asp Ala Ile Tyr Phe Cys Gly Asn Ser Leu Gly Leu Gln Pro
        35                  40                  45

Lys Ser Ala Gln Met Tyr Ile Asp Asn Glu Met Tyr Lys Trp Ala Asn
50                  55                  60

Tyr Ala Val Glu Gly His Phe Lys Val Glu Glu Pro Trp Phe Asn Tyr
65                  70                  75                  80

His Arg Leu Leu Thr Asp Gly Ala Ala Arg Val Gly Ala Arg Pro
                85                  90                  95

Gln Glu Val Val Ile Met Asn Gln Leu Thr Val Asn Leu His Leu Met
            100                 105                 110

Leu Val Ser Phe Tyr Arg Pro Glu Gly Arg Arg Ile Lys Ile Ile Met
        115                 120                 125

Glu Gly Gly Ala Phe Pro Ser Asp Gln Tyr Ala Leu Glu Thr Gln Val
130                 135                 140

Lys Phe His Gly Tyr Thr Pro Glu Glu Ala Ile Ile Glu Leu Phe Pro
145                 150                 155                 160

Arg Glu Gly Glu His Thr Leu Arg Thr Glu Asp Ile Leu Lys Ser Ile
                165                 170                 175

Glu Ala Ala Gly Asp Glu Leu Ala Leu Val Leu Met Gly Gly Ile Asn
            180                 185                 190

Tyr Tyr Thr Gly Gln Val Tyr Asp Met Ala Ala Ile Thr Gln Ala Gly
        195                 200                 205

His Gly Val Gly Ala Val Val Gly Phe Asp Leu Ala His Ala Ala Gly
210                 215                 220

Asn Val Pro Leu Gln Leu His Asp Trp Gly Val Asp Phe Ala Val Trp
225                 230                 235                 240

Cys Thr Tyr Lys Tyr Leu Asn Ser Gly Pro Gly Thr Ala Gly Val
                245                 250                 255

Phe Val His Glu Arg His Ala Asn Asn Pro Asp Leu Pro Arg Phe Ala
            260                 265                 270

Gly Trp Trp Gly His Asp Ala Ser Val Arg Phe Gln Met Lys Lys Gly
        275                 280                 285

Phe Ile Pro Met Thr Gly Ala Glu Gly Trp Gln Leu Ser Asn Ala Gln
290                 295                 300

Ile Leu Pro Met Ala Val His Arg Ala Leu Glu Leu Phe Asp Glu
305                 310                 315                 320

Ala Gly Met Asp Asn Leu Arg Ala Lys Ser Glu Lys Leu Thr Gly Tyr
                325                 330                 335

Leu Glu Tyr Leu Ile Asp Asp Val His Val Gly Lys Glu Leu Leu Glu
            340                 345                 350
```

Met Ile Thr Pro Arg Asp Pro Gln Ala Arg Gly Cys Gln Ile Ser Leu
            355                 360                 365

Leu Val Lys Gln Asn Ala Arg Glu Leu Phe Asn Arg Leu Met Glu Ala
        370                 375                 380

Gly Ile Ile Val Asp Phe Arg Glu Pro Ser Val Ile Arg Val Ala Pro
385                 390                 395                 400

Thr Pro Leu Tyr Asn Ser Phe Glu Glu Val Tyr Arg Phe Ser Glu Ile
            405                 410                 415

Leu His Asp Cys Leu Gln Ser His
            420

<210> SEQ ID NO 53
<211> LENGTH: 1304
<212> TYPE: DNA
<213> ORGANISM: Artificial Sequence
<220> FEATURE:
<223> OTHER INFORMATION: Synthetic polynucleotide

<400> SEQUENCE: 53
ccatgggcgg acaccatcat caccaccacg gcggcattga aaaactgaaa cagtatcacg     60
atgaagcgat cagcctggat agccttgatc ccttacagaa attcaaagaa tgctttacat    120
taccgaagga acctggagca ctgtatttct gcagcaatag tctgggcttg cccgcgaaag    180
cggcttccca gaaactggaa gaacagttac agcggtggag cgaattaggc gctcgtggat    240
ggtttgaagg cgagggtaat tggtataaca gcttggaaga gcctattgtg cgtccattga    300
gcaaaatctt aggagcggaa agcaatgaag tgaccctgat gaatagcttg accgtgaatc    360
tgcacatgtt gttgattagt ttctatcgtc cgaccaaaat gcgttataag atactgattg    420
atggcccagc ctttccgtcc gatctgtatg ccattaagtc gcatctgcgt tttcataaga    480
aagaagaagg tcttattctg atagaaccgc gtccgggcga acatctggtg caggaagaag    540
actttctgcg cgtgataaag aagcaaggag aggaaattgc gttggtgttt ctgaactgcg    600
tgaattttct gagcggccag gtgctgaaag tggatgaaat caccgttat gccaaggagg    660
ctggctgctg cgtcggttat gatctggcgc atgcagcagg caatattccc ttaagcttgc    720
atgatcttgg cggcgacttt gcggtgggct gctcctacaa atatctgtgc ggaggcccag    780
gaggtccagg catagcctac gttcacgcgt cacatcacca ccaacagttc gtgcgtttca    840
gcgggtggtg gggcaatgat ccgaataccc ggttttactt ccccaaagag tttgtgccgt    900
atggcggtgc gagctcctgg caggtgagca ccccgtcgat tctggcgaaa ctgccgttaa    960
ttgcggcact ggaggtgttt gaggaagcgg gcatggagaa tatacgtgaa aagagcaaga   1020
aacaaacagc gttcctgtat accctgttag aaaatgctcg cggcacccat tttgatatga   1080
taaccccgaa agaaccggag ctgcgtggct gtcagcttag cctgcgtatc aaatgcagcc   1140
gtagcgaaga gatcttacgg aagctggaac gtttaggcat tacatgcgat ttccgttcgc   1200
cgaacattct gcgtgtggcg ccgagcccgt tgtacaccag ctttttacgaa atctatcgtt   1260
ttgcgtacac ctttctggaa gtcctgaaaa ccatttgaga attc                    1304

<210> SEQ ID NO 54
<211> LENGTH: 431
<212> TYPE: PRT
<213> ORGANISM: Artificial Sequence
<220> FEATURE:
<223> OTHER INFORMATION: Synthetic polypeptide

<400> SEQUENCE: 54

```
Met Gly Gly His His His His His Gly Ile Glu Lys Leu Lys
1               5                   10              15

Gln Tyr His Asp Glu Ala Ile Ser Leu Asp Ser Leu Asp Pro Leu Gln
            20                  25                  30

Lys Phe Lys Glu Cys Phe Thr Leu Pro Lys Glu Pro Gly Ala Leu Tyr
        35                  40                  45

Phe Cys Ser Asn Ser Leu Gly Leu Pro Ala Lys Ala Ala Ser Gln Lys
    50                  55                  60

Leu Glu Glu Gln Leu Gln Arg Trp Ser Glu Leu Gly Ala Arg Gly Trp
65                  70                  75                  80

Phe Glu Gly Glu Gly Asn Trp Tyr Asn Ser Leu Glu Glu Pro Ile Val
                85                  90                  95

Arg Pro Leu Ser Lys Ile Leu Gly Ala Glu Ser Asn Glu Val Thr Leu
                100                 105                 110

Met Asn Ser Leu Thr Val Asn Leu His Met Leu Leu Ile Ser Phe Tyr
                115                 120                 125

Arg Pro Thr Lys Met Arg Tyr Lys Ile Leu Ile Asp Gly Pro Ala Phe
            130                 135                 140

Pro Ser Asp Leu Tyr Ala Ile Lys Ser His Leu Arg Phe His Lys Lys
145                 150                 155                 160

Glu Glu Gly Leu Ile Leu Ile Glu Pro Arg Pro Gly Glu His Leu Val
                165                 170                 175

Gln Glu Glu Asp Phe Leu Arg Val Ile Lys Lys Gln Gly Glu Glu Ile
            180                 185                 190

Ala Leu Val Phe Leu Asn Cys Val Asn Phe Leu Ser Gly Gln Val Leu
                195                 200                 205

Lys Val Asp Glu Ile Thr Arg Tyr Ala Lys Glu Ala Gly Cys Cys Val
                210                 215                 220

Gly Tyr Asp Leu Ala His Ala Ala Gly Asn Ile Pro Leu Ser Leu His
225                 230                 235                 240

Asp Leu Gly Gly Asp Phe Ala Val Gly Cys Ser Tyr Lys Tyr Leu Cys
                245                 250                 255

Gly Gly Pro Gly Gly Pro Gly Ile Ala Tyr Val His Ala Ser His His
                260                 265                 270

His Gln Gln Phe Val Arg Phe Ser Gly Trp Trp Gly Asn Asp Pro Asn
            275                 280                 285

Thr Arg Phe Tyr Phe Pro Lys Glu Phe Val Pro Tyr Gly Gly Ala Ser
            290                 295                 300

Ser Trp Gln Val Ser Thr Pro Ser Ile Leu Ala Lys Leu Pro Leu Ile
305                 310                 315                 320

Ala Ala Leu Glu Val Phe Glu Glu Ala Gly Met Glu Asn Ile Arg Glu
                325                 330                 335

Lys Ser Lys Lys Gln Thr Ala Phe Leu Tyr Thr Leu Leu Glu Asn Ala
            340                 345                 350

Arg Gly Thr His Phe Asp Met Ile Thr Pro Lys Glu Pro Glu Leu Arg
            355                 360                 365

Gly Cys Gln Leu Ser Leu Arg Ile Lys Cys Ser Arg Ser Glu Glu Ile
    370                 375                 380

Leu Arg Lys Leu Glu Arg Leu Gly Ile Thr Cys Asp Phe Arg Ser Pro
385                 390                 395                 400

Asn Ile Leu Arg Val Ala Pro Ser Pro Leu Tyr Thr Ser Phe Tyr Glu
                405                 410                 415
```

Ile Tyr Arg Phe Ala Tyr Thr Phe Leu Glu Val Leu Lys Thr Ile
            420                 425                 430

<210> SEQ ID NO 55
<211> LENGTH: 464
<212> TYPE: PRT
<213> ORGANISM: Artificial Sequence
<220> FEATURE:
<223> OTHER INFORMATION: Synthetic polypeptide

<400> SEQUENCE: 55

Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Leu Asp Lys Trp Ala Lys
            85                  90                  95

Ile Ala Ala Tyr Gly His Glu Val Gly Lys Arg Pro Trp Ile Thr Gly
                100                 105                 110

Asp Glu Ser Ile Val Gly Leu Met Lys Asp Ile Val Gly Ala Asn Glu
            115                 120                 125

Lys Glu Ile Ala Leu Met Asn Ala Leu Thr Val Asn Leu His Leu Leu
130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Thr Leu Arg Ile Glu Asp Ile Leu Glu Val Ile
            195                 200                 205

Glu Lys Glu Gly Asp Ser Ile Ala Val Ile Leu Phe Ser Gly Val His
210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255

Asn Val Glu Leu Tyr Leu His Asp Trp Gly Val Asp Phe Ala Cys Trp
            260                 265                 270

Cys Ser Tyr Lys Tyr Leu Asn Ala Gly Ala Gly Gly Ile Ala Gly Ala
        275                 280                 285

Phe Ile His Glu Lys His Ala His Thr Ile Lys Pro Ala Leu Val Gly
290                 295                 300

Trp Met Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Pro Ile
                325                 330                 335

Leu Leu Val Cys Ser Leu His Ala Ser Leu Glu Ile Phe Lys Gln Thr
            340                 345                 350

```
Met Lys Ala Leu Arg Lys Lys Ser Val Leu Leu Thr Gly Tyr Leu Glu
            355                 360                 365

Tyr Leu Ile Lys His Asn Tyr Gly Lys Asp Lys Ala Ala Thr Lys Lys
    370                 375                 380

Pro Val Val Asn Ile Ile Thr Pro Ser His Val Glu Glu Arg Gly Cys
385                 390                 395                 400

Gln Leu Thr Ile Thr Phe Ser Val Pro Asn Lys Asp Val Phe Gln Glu
                405                 410                 415

Leu Glu Lys Arg Gly Val Val Cys Asp Lys Arg Asn Pro Asn Gly Ile
            420                 425                 430

Arg Val Ala Pro Val Pro Leu Tyr Asn Ser Phe His Asp Val Tyr Lys
        435                 440                 445

Phe Thr Asn Leu Leu Thr Ser Ile Leu Asp Ser Ala Glu Thr Lys Asn
    450                 455                 460
```

<210> SEQ ID NO 56
<211> LENGTH: 464
<212> TYPE: PRT
<213> ORGANISM: Artificial Sequence
<220> FEATURE:
<223> OTHER INFORMATION: Synthetic polypeptide

<400> SEQUENCE: 56

```
Met Glu Pro Ser Ser Leu Glu Leu Pro Ala Asp Thr Val Gln Arg Ile
1               5                   10                  15

Ala Ala Glu Leu Lys Cys His Pro Thr Asp Glu Arg Val Ala Leu His
            20                  25                  30

Leu Asp Glu Asp Lys Leu Arg His Phe Arg Glu Cys Phe Tyr Ile
        35                  40                  45

Pro Lys Ile Gln Asp Leu Pro Pro Val Asp Leu Ser Leu Val Asn Lys
    50                  55                  60

Asp Glu Asn Ala Ile Tyr Phe Leu Gly Asn Ser Leu Gly Leu Gln Pro
65                  70                  75                  80

Lys Met Val Lys Thr Tyr Leu Glu Glu Glu Leu Asp Lys Trp Ala Lys
                85                  90                  95

Ile Ala Ala Tyr Gly His Glu Val Gly Lys Arg Pro Trp Ile Thr Gly
            100                 105                 110

Asp Glu Ser Ile Val Gly Leu Met Lys Asp Ile Val Gly Ala Asn Glu
        115                 120                 125

Lys Glu Ile Ala Leu Met Asn Ala Leu Thr Val Asn Leu His Leu Leu
    130                 135                 140

Met Leu Ser Phe Phe Lys Pro Thr Pro Lys Arg Tyr Lys Ile Leu Leu
145                 150                 155                 160

Glu Ala Lys Ala Phe Pro Ser Asp His Tyr Ala Ile Glu Ser Gln Leu
                165                 170                 175

Gln Leu His Gly Leu Asn Ile Glu Glu Ser Met Arg Met Ile Lys Pro
            180                 185                 190

Arg Glu Gly Glu Glu Thr Leu Arg Ile Glu Asp Ile Leu Glu Val Ile
        195                 200                 205

Glu Lys Glu Gly Asp Ser Ile Ala Val Ile Leu Phe Ser Gly Val His
    210                 215                 220

Phe Tyr Thr Gly Gln His Phe Asn Ile Pro Ala Ile Thr Lys Ala Gly
225                 230                 235                 240

Gln Ala Lys Gly Cys Tyr Val Gly Phe Asp Leu Ala His Ala Val Gly
                245                 250                 255
```

```
Asn Val Glu Leu Tyr Leu His Asp Trp Gly Val Asp Phe Ala Cys Trp
                260                 265                 270

Cys Ser Tyr Lys Tyr Leu Asn Ala Gly Ala Gly Ile Ala Gly Ala
        275                 280                 285

Phe Ile His Glu Lys His Ala His Thr Ile Lys Pro Ala Leu Val Gly
    290                 295                 300

Trp Leu Gly His Glu Leu Ser Thr Arg Phe Lys Met Asp Asn Lys Leu
305                 310                 315                 320

Gln Leu Ile Pro Gly Val Cys Gly Phe Arg Ile Ser Asn Pro Ile
                325                 330                 335

Leu Leu Val Cys Ser Leu His Ala Ser Leu Glu Ile Phe Lys Gln Thr
            340                 345                 350

Met Lys Ala Leu Arg Lys Lys Ser Val Leu Leu Thr Gly Tyr Leu Glu
        355                 360                 365

Tyr Leu Ile Lys His Asn Tyr Gly Lys Asp Lys Ala Ala Thr Lys Lys
    370                 375                 380

Pro Val Val Asn Ile Ile Thr Pro Ser His Val Glu Glu Arg Gly Cys
385                 390                 395                 400

Gln Leu Thr Ile Thr Phe Ser Val Pro Asn Lys Asp Val Phe Gln Glu
                405                 410                 415

Leu Glu Lys Arg Gly Val Val Cys Asp Lys Arg Asn Pro Asn Gly Ile
            420                 425                 430

Arg Val Ala Pro Val Pro Leu Tyr Asn Ser Phe His Asp Val Tyr Lys
        435                 440                 445

Phe Thr Asn Leu Leu Thr Ser Ile Leu Asp Ser Ala Glu Thr Lys Asn
    450                 455                 460

<210> SEQ ID NO 57
<211> LENGTH: 420
<212> TYPE: PRT
<213> ORGANISM: Chlamydophila pecorum

<400> SEQUENCE: 57

Ile Glu Lys Leu Lys Gln Tyr His Asp Glu Ala Ile Ser Leu Asp Ser
1               5                   10                  15

Leu Asp Pro Leu Gln Lys Phe Lys Glu Cys Phe Thr Leu Pro Lys Glu
            20                  25                  30

Pro Gly Ala Leu Tyr Phe Cys Ser Asn Ser Leu Gly Leu Pro Ala Lys
        35                  40                  45

Ala Ala Ser Gln Lys Leu Glu Glu Gln Leu Gln Arg Trp Ser Glu Leu
    50                  55                  60

Gly Ala Arg Gly Trp Phe Glu Gly Gly Asn Trp Tyr Asn Ser Leu
65                  70                  75                  80

Glu Glu Pro Ile Val Arg Pro Leu Ser Lys Ile Leu Gly Ala Glu Ser
                85                  90                  95

Asn Glu Val Thr Leu Met Asn Ser Leu Thr Val Asn Leu His Met Leu
            100                 105                 110

Leu Ile Ser Phe Tyr Arg Pro Thr Lys Met Arg Tyr Lys Ile Leu Ile
        115                 120                 125

Asp Gly Pro Ala Phe Pro Ser Asp Leu Tyr Ala Ile Lys Ser His Leu
    130                 135                 140

Arg Phe His Lys Lys Glu Glu Gly Leu Ile Leu Ile Glu Pro Arg Pro
145                 150                 155                 160

Gly Glu His Leu Val Gln Glu Glu Asp Phe Leu Arg Val Ile Lys Lys
                165                 170                 175
```

```
Gln Gly Glu Glu Ile Ala Leu Val Phe Leu Asn Cys Val Asn Phe Leu
            180             185             190

Ser Gly Gln Val Leu Lys Val Asp Glu Ile Thr Arg Tyr Ala Lys Glu
            195             200             205

Ala Gly Cys Cys Val Gly Tyr Asp Leu Ala His Ala Ala Gly Asn Ile
            210             215             220

Pro Leu Ser Leu His Asp Leu Gly Gly Asp Phe Ala Val Gly Cys Ser
225             230             235             240

Tyr Lys Tyr Leu Cys Gly Gly Pro Gly Pro Gly Ile Ala Tyr Val
                245             250             255

His Ala Ser His His His Gln Gln Phe Val Arg Phe Ser Gly Trp Trp
            260             265             270

Gly Asn Asp Pro Asn Thr Arg Phe Tyr Phe Pro Lys Glu Phe Val Pro
            275             280             285

Tyr Gly Gly Ala Ser Ser Trp Gln Val Ser Thr Pro Ser Ile Leu Ala
        290             295             300

Lys Leu Pro Leu Ile Ala Ala Leu Glu Val Phe Glu Glu Ala Gly Met
305             310             315             320

Glu Asn Ile Arg Glu Lys Ser Lys Lys Gln Thr Ala Phe Leu Tyr Thr
                325             330             335

Leu Leu Glu Asn Ala Arg Gly Thr His Phe Asp Met Ile Thr Pro Lys
            340             345             350

Glu Pro Glu Leu Arg Gly Cys Gln Leu Ser Leu Arg Ile Lys Cys Ser
            355             360             365

Arg Ser Glu Glu Ile Leu Arg Lys Leu Glu Arg Leu Gly Ile Thr Cys
    370             375             380

Asp Phe Arg Ser Pro Asn Ile Leu Arg Val Ala Pro Ser Pro Leu Tyr
385             390             395             400

Thr Ser Phe Tyr Glu Ile Tyr Arg Phe Ala Tyr Thr Phe Leu Glu Val
                405             410             415

Leu Lys Thr Ile
            420
```